(12) United States Patent
Lan et al.

(10) Patent No.: US 10,561,646 B2
(45) Date of Patent: Feb. 18, 2020

(54) EGFR INHIBITOR AND PHARMACEUTICALLY ACCEPTABLE SALT AND POLYMORPH THEREOF, AND USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Jiong Lan, Shanghai (CN); Taotao Jiang, Shanghai (CN); Daofei Li, Shanghai (CN); Xing Liu, Shanghai (CN)

(73) Assignees: SHANGHAI HAIYAN PHARMACEUTICAL TECHNOLOGY CO. LTD., Shanghai (CN); YANGTZE RIVER PHARMACEUTICAL GROUP CO., LTD., Jiangsu (CN)

( * ) Notice: Subject to any disclaimer, the term of this patent is extended or adjusted under 35 U.S.C. 154(b) by 0 days.

(21) Appl. No.: 15/746,966

(22) PCT Filed: Jul. 25, 2016

(86) PCT No.: PCT/CN2016/091591
§ 371 (c)(1),
(2) Date: Jan. 24, 2018

(87) PCT Pub. No.: WO2017/016463
PCT Pub. Date: Feb. 2, 2017

(65) Prior Publication Data
US 2018/0319770 A1 Nov. 8, 2018

(30) Foreign Application Priority Data
Jul. 24, 2015 (CN) .......................... 2015 1 0443673

(51) Int. Cl.
| | | |
|---|---|---|
| *C07D 401/14* | (2006.01) |
| *A61K 31/506* | (2006.01) |
| *A61P 35/00* | (2006.01) |
| *A61K 31/4468* | (2006.01) |

(52) U.S. Cl.
CPC ........ *A61K 31/4468* (2013.01); *A61K 31/506* (2013.01); *C07D 401/14* (2013.01)

(58) Field of Classification Search
CPC .................................................... C07D 401/14
See application file for complete search history.

(56) References Cited

U.S. PATENT DOCUMENTS

| | | |
|---|---|---|
| 8,309,718 B2 | 11/2012 | Li et al. |
| 2013/0053409 A1 | 2/2013 | Butterworth et al. |
| 2015/0344441 A1 | 12/2015 | Lai et al. |
| 2017/0008889 A1 | 1/2017 | Lan et al. |

FOREIGN PATENT DOCUMENTS

| | | |
|---|---|---|
| CN | 101910152 A | 12/2010 |
| CN | 103702990 A | 4/2014 |
| CN | 104284584 A | 1/2015 |
| WO | 2015/127872 A1 | 9/2015 |

OTHER PUBLICATIONS

Burger's Medicinal Chemistry, edited by Manfred E. Wolff, 5th Ed. Part 1, pp. 975-977 (1995). (Year: 1995).*
Banker et al. "Modern Pharmaceutics", 3rd Ed. p. 596(1996). (Year: 1996).*
Galvani et al. Current Pharmaceutical Design vol. 19, 818-832. (Year: 2013).*
Choo et al. Targeted Oncology (2018) 13:141-156 (Year: 2018).*
English Translation of the International Search Report corresponding to PCT/CN2016/091591 dated Oct. 26, 2016, 3 pages.

* cited by examiner

*Primary Examiner* — Emily A Bernhardt
(74) *Attorney, Agent, or Firm* — Mintz Levin Cohn Ferris Glovsky and Popeo PC

(57) ABSTRACT

Provided is an EGFR inhibitor and a pharmaceutically acceptable salt and a polymorph thereof, and a use thereof. In particular, provided is a polymorph, a pharmaceutically acceptable salt or a prodrug of N-(2-(4-(dimethylamino) piperid-1-yl)-5-(5-fluoro-4-(1-methyl-1H-pyrazol-4-yl) pyrimidin-2-ylamino)-4-methoxy phenyl) acrylamide. In addition, also provided is a pharmaceutical composition containing the inhibitor and a use thereof.

15 Claims, 20 Drawing Sheets

EGFR INHIBITOR AND PHARMACEUTICALLY ACCEPTABLE SALT AND POLYMORPH THEREOF, AND USE THEREOF

TECHNICAL FIELD

The present invention belongs to the technical field of medicine. In particular, the present invention relates to an EGFR inhibitor and pharmaceutically acceptable salts and polymorphs thereof and their applications, and the inhibitor is N-(2-(4-(dimethylamino)piperidin-1-yl)-5-(5-fluoro-4-(1-methyl-1H-pyrazol-4-yl)pyrimidin-2-yl-amino)-4-methoxyphenyl)acrylamide.

BACKGROUND

Lung cancer is of the highest incidence in the world. In China, the incidence of lung cancer ranks first among all cancers, and the incidence and mortality rates of the cancer are also the highest in China. In the lung cancer patients in China, 30% of patients have EGFR mutations, over 90% of which are L858R and exon 19 deletion-mutation, and these patients are more sensitive to EGFR inhibitors. The marketed first-generation of EGFR inhibitors, such as erlotinib, gefitinib have good effect for these patients, and the tumor in more than 60% of patients will shrink, significantly prolonging the progression-free survival of patients. However, most of patients acquire resistance in 6-12 months, the first generation of EGFR inhibitors will no longer take effect, and currently no drugs are available for these patients. EGFR T790M mutation is clinically detected in 50% of patients who are resistant to the first-generation of EGFR inhibitors. In T790M mutant cell line H1975, the activity of the first-generation of EGFR inhibitors, such as gefitinib and erlotinib, was greater than 3 uM, which means almost no activity.

The therapeutic effect of the second generation of irreversible pan-EGFR inhibitors (Afatinib (BIBW2992)) currently launched was significantly better than that of the first-generation of EGFR inhibitors for lung cancer patients with EGFR mutations. However, the second-generation of inhibitors also have strong inhibitory activity for wild-type EGFR, and the inhibitory activity for wild-type EGFR was significantly higher than that for resistant T790M mutation, and side effects, such as skin rashes, were severe in patients, and the effect of the second-generation of inhibitors on drug resistant patients was poor, only a small part of patients who are resistant to the first generation of EGFR inhibitors response to these drugs.

For improving the inhibitory activity for resistant T790M mutation while reducing the inhibitory activity for wild-type EGFR, it is of great significance to develop the third generation of selective inhibitors for EGFR mutants with higher activity, better selectivity, and lower toxicity. On the basis of the foregoing work, a variety of salts and polymorphs of inhibitors of EGFR mutants have been developed, which will facilitate further drug development.

SUMMARY OF INVENTION

The object of the present invention is to provide an inhibitor that effectively inhibits EGFR mutants, pharmaceutically acceptable salts and polymorphs, and uses thereof.

In the first aspect of the present invention, a compound of formula X, or a pharmaceutically acceptable salt, or a prodrug thereof is provided:

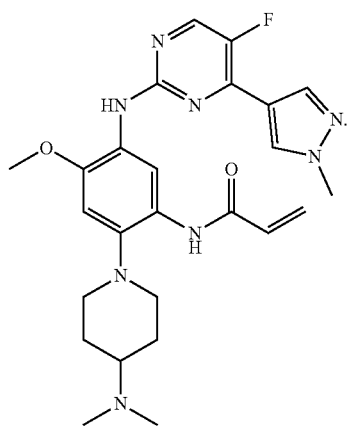

(X)

In another preferred embodiment, the pharmaceutically acceptable salt is selected from the group consisting of hydrochloride, sulfate, phosphate, acetate, L-lactate, maleate, fumarate, succinate, L-malate, adipate, L-tartrate, hippurate, citrate, mucate, glycolate, D-glucuronate, benzoate, gentisinate, nicotinate, ethanedisulfonate, oxalate, methanesulfonate, benzenesulfonate, 2-hydroxyethanesulfonate and hydrobromide.

In another preferred embodiment, the pharmaceutically acceptable salt is selected from the group consisting of hydrochloride, phosphate, maleate, L-malate, adipate, sulfate, fumarate, succinate, L-tartrate, citrate, methanesulfonate, benzoate and benzenesulfonate.

In another preferred embodiment, the compound of formula X, or its pharmaceutically acceptable salt is in an anhydrous form, hydrate form or solvate form.

In another preferred embodiment, the solvate includes a methanol solvate and an ethyl acetate solvate.

In another preferred embodiment, the compound of formula X, or its pharmaceutically acceptable salt is a crystal.

In another preferred embodiment, the pharmaceutically acceptable salt is selected from the group consisting of hydrochloride, phosphate, maleate, L-malate, adipate, sulfate, fumarate, succinate, L-tartrate, citrate, methanesulfonate, benzoate, and benzenesulfonate.

In another preferred embodiment, the pharmaceutically acceptable salt is a hydrochloride, wherein the molar ratio of hydrochloric acid to the compound of formula X is (0.8-2.1):1, preferably (0.9-1.1):1.

In another preferred embodiment, the pharmaceutically acceptable salt is phosphate, wherein the molar ratio of phosphoric acid to the compound of formula X is 1:(0.9-2.1), preferably 1:(1.1-2.1).

In another preferred embodiment, the pharmaceutically acceptable salt is a maleate, wherein the molar ratio of maleic acid to the compound of formula X is (0.8-1.2):1, preferably (0.9-1.1):1, more preferably 1:1.

In another preferred embodiment, the pharmaceutically acceptable salt is L-malate, wherein the molar ratio of L-maleic acid to the compound of formula X is (0.5-1.4):1, preferably (0.7-1.3):1.

In another preferred embodiment, the pharmaceutically acceptable salt is adipate, wherein the molar ratio of adipic acid to the compound of formula X is (0.8-1.2):1, preferably (0.9-1.1):1.

In another preferred embodiment, the pharmaceutically acceptable salt is fumarate, wherein the molar ratio of fumaric acid to the compound of formula X is (0.5-1.2):1, preferably (0.5-1):1.

In another preferred embodiment, the pharmaceutically acceptable salt is citrate, wherein the molar ratio of citric acid to the compound of formula X is (0.5-1.2):1, preferably (0.5-1):1.

In another preferred embodiment, the pharmaceutically acceptable salt is a mucate, wherein the molar ratio of mucic acid to the compound of formula X is (0.5-1.2):1, preferably (0.5-1):1.

In another preferred embodiment, the pharmaceutically acceptable salt is a succinate, wherein the molar ratio of succinic acid to the compound of formula X is (0.9-1.1):1, preferably 1:1.

In another preferred embodiment, the pharmaceutically acceptable salt is L-tartrate, wherein the molar ratio of L-tartaric acid to the compound of formula X is (0.9-1.1):1, preferably 1:1.

In another preferred embodiment, the pharmaceutically acceptable salt is nicotinate, wherein the molar ratio of nicotinic acid to the compound of formula X is (0.9-1.1):1, preferably 1:1.

In another preferred embodiment, the pharmaceutically acceptable salt is hippurate, wherein the molar ratio of hippuric acid to the compound of formula X is from (0.9-1.1):1, preferably from 1:1.

In another preferred embodiment, the pharmaceutically acceptable salt is glycolate, wherein the molar ratio of glycolic acid to the compound of formula X is (0.9-1.1):1, preferably 1:1.

In another preferred embodiment, the pharmaceutically acceptable salt is benzoate, wherein the molar ratio of benzoic acid to the compound of formula X is (0.9-1.1):1, preferably 1:1.

In another preferred embodiment, the pharmaceutically acceptable salt is gentisate, wherein the molar ratio of gentisic acid to the compound of formula X is (0.9-1.1):1, preferably 1:1.

In another preferred embodiment, the pharmaceutically acceptable salt is ethanedisulfonate, wherein the molar ratio of ethanedisulfonic acid to the compound of formula X is (0.9-1.1):1, preferably 1:1.

In another preferred embodiment, the pharmaceutically acceptable salt is oxalate, wherein the molar ratio of oxalic acid to the compound of formula X is (0.9-1.1):1, preferably 1:1.

In another preferred embodiment, the pharmaceutically acceptable salt is methanesulfonate, wherein the molar ratio of methanesulfonic acid to the compound of formula X is (0.9-1.1):1, preferably 1:1.

In another preferred embodiment, the pharmaceutically acceptable salt is benzenesulfonate, wherein the molar ratio of benzenesulfonic acid to the compound of formula X is (0.9-1.1):1, preferably 1:1.

In another preferred embodiment, the pharmaceutically acceptable salt is 2-hydroxyethanesulfonate, wherein the molar ratio of 2-hydroxyethanesulfonic acid to the compound of formula X is (0.9-1.1):1, preferably 1:1.

In another preferred embodiment, the pharmaceutically acceptable salt is D-glucuronate, wherein the molar ratio of D-glucuronic acid to the compound of formula X is (0.9-1.1):1, preferably 1:1.

In another preferred embodiment, the crystal is A crystalline form of the hydrochloride of compound of formula X, i.e. crystal form A, which has an X-ray powder diffraction pattern with diffraction angle 2θ(°) values of the following group A1: 8.47±0.10, 20.32±0.10, 23.31±0.10 (the highest peak) and 25.98±0.10.

In another preferred embodiment, the X-ray powder diffraction pattern of crystal form A further includes 2 or more diffraction angle 2θ(°) values selected from the following group A2: 15.54±0.10, 16.97±0.10, 17.66±0.10, 17.90±0.10, 21.54±0.10, 22.19±0.10, 23.37±0.10, 24.81±0.10.

In another preferred embodiment, the X-ray powder diffraction pattern of crystal form A further includes 2 or more diffraction angle 2θ(°) values selected from the following group A3: 9.44±0.10, 11.78±0.10, 13.29±0.10, 14.91±0.10, 15.23±0.10, 18.20±0.10, 18.68±0.10, 20.05±0.10, 21.07±0.10, 23.87±0.10, 24.19±0.10, 25.30±0.10, 25.61±0.10, 26.45±0.10, 27.42±0.10, 28.49±0.10, 29.96±0.10, 32.00±0.10, 34.01±0.10, 35.25±0.10.

In another preferred embodiment, the X-ray powder diffraction pattern of crystal form A includes six or more or all 2θ(°) values selected from the group A1, A2, and A3 (such as 6, 7, 8, 9, 11, 12, 13, 14, 15, etc.).

In another preferred embodiment, the X-ray powder diffraction pattern of crystal form A has the values shown in Table A2 below:

TABLE A2

| 2θ(°) | d value [Å] | relative intensity I/I₀ [%] | 2θ(°) | d value [Å] | relative intensity I/I₀ [%] |
|---|---|---|---|---|---|
| 8.47 | 10.43 | VS | 9.44 | 9.37 | M |
| 11.78 | 7.51 | M | 13.29 | 6.66 | M |
| 14.91 | 5.94 | M | 15.23 | 5.82 | M |
| 15.54 | 5.70 | S | 16.97 | 5.23 | S |
| 17.66 | 5.02 | S | 17.90 | 4.96 | S |
| 18.20 | 4.87 | M | 18.68 | 4.75 | M |
| 20.05 | 4.43 | M | 20.32 | 4.37 | S |
| 21.07 | 4.22 | M | 21.54 | 4.13 | S |
| 22.19 | 4.01 | S | 23.31 | 3.81 | VS |
| 23.37 | 3.81 | VS | 23.87 | 3.72 | M |
| 24.19 | 3.68 | M | 24.81 | 3.59 | S |
| 25.30 | 3.52 | M | 25.61 | 3.48 | M |
| 25.98 | 3.43 | S | 26.45 | 3.37 | M |
| 27.42 | 3.25 | M | 28.49 | 3.13 | M |
| 29.12 | 3.06 | W | 29.96 | 2.98 | M |
| 32.00 | 2.79 | M | 32.44 | 2.76 | W |
| 34.01 | 2.63 | M | 35.25 | 2.54 | M |
| 35.88 | 2.50 | W | 37.32 | 2.41 | W |

In another preferred embodiment, the X-ray powder diffraction pattern of crystal form A is substantially as shown in FIG. 1.

In another preferred embodiment, the molar ratio of hydrochloric acid to the compound of formula X in crystal form A is (0.8-2.1):1, preferably (0.9-1.1):1, more preferably 0.9:1.

In another preferred embodiment, the crystal form A further has one or more features selected from the following group:

(i) In the differential scanning calorimetry analysis spectrum, the starting temperature is 259±2° C.; preferably, its differential scanning calorimetry analysis spectrum is substantially as shown in FIG. 2C;

(ii) Thermogravimetric analysis spectrum is substantially as shown in FIG. 2C;

(iii) The crystal form A has a melting point of 259° C.-267° C., preferably 261° C.-265° C.

In another preferred embodiment, the crystal form A is in a hydrate form.

In another preferred embodiment, the crystal is B crystalline form of the phosphate of compound of formula X, i.e. crystal form B, which has an X-ray powder diffraction pattern with diffraction angle 2θ(°) values of the following group B1: 11.94±0.10, 19.92±0.10 (the highest peak), 22.27±0.10, 23.93±0.10.

In another preferred embodiment, the X-ray diffraction pattern of crystal form B further includes diffraction angle 2θ(°) values of the following group B2: 7.97±0.10, 9.50±0.10.

In another preferred embodiment, the X-ray diffraction pattern of crystal form B further includes 2 or more diffraction angle 2θ(°) values selected from the following group B3: 4.01±0.10, 10.71±0.10, 12.11±0.10, 12.56±0.10, 12.89±0.10, 13.94±0.10, 14.47±0.10, 15.16±0.10, 15.52±0.10, 16.54±0.10, 17.00±0.10, 17.42±0.10, 17.99±0.10, 18.38±0.10, 18.91±0.10, 20.81±0.10, 20.96±0.10, 21.29±0.10, 21.65±0.10, 21.99±0.10, 22.58±0.10, 23.02±0.10, 23.45±0.10, 24.31±0.10, 24.53±0.10, 24.76±0.10, 25.01±0.10, 27.29±0.10, 28.98±0.10.

In another preferred embodiment, the X-ray diffraction pattern of crystal form B includes six or more or all 2θ(°) values selected from the group B1, B2, and B3 (such as 6, 7, 8, 9, 11, 12, 13, 14, 15, etc.).

In another preferred embodiment, the X-ray diffraction pattern of crystal form B has the values shown in Table B2 below:

TABLE B2

| 2θ(°) | d value [Å] | relative intensity I/I$_0$ [%] | 2θ(°) | d value [Å] | relative intensity I/I$_0$ [%] |
|---|---|---|---|---|---|
| 4.01 | 22.04 | M | 6.65 | 13.29 | W |
| 7.97 | 11.09 | S | 9.50 | 9.31 | S |
| 10.71 | 8.26 | M | 11.94 | 7.41 | S |
| 12.11 | 7.31 | M | 12.56 | 7.05 | M |
| 12.89 | 6.87 | M | 13.94 | 6.35 | M |
| 14.47 | 6.12 | M | 15.16 | 5.85 | M |
| 15.52 | 5.71 | M | 16.54 | 5.36 | M |
| 17.00 | 5.22 | M | 17.42 | 5.09 | M |
| 17.99 | 4.93 | M | 18.38 | 4.83 | M |
| 18.91 | 4.69 | M | 19.92 | 4.46 | VS |
| 20.81 | 4.27 | M | 20.96 | 4.24 | M |
| 21.29 | 4.17 | M | 21.65 | 4.11 | M |
| 21.99 | 4.04 | M | 22.27 | 3.99 | VS |
| 22.58 | 3.94 | M | 23.02 | 3.86 | M |
| 23.45 | 3.79 | M | 23.93 | 3.72 | VS |
| 24.31 | 3.66 | M | 24.53 | 3.63 | M |
| 24.76 | 3.60 | M | 25.01 | 3.56 | M |
| 26.85 | 3.32 | W | 27.29 | 3.27 | M |
| 28.02 | 3.18 | W | 28.98 | 3.08 | M |
| 30.45 | 2.94 | W | 32.13 | 2.79 | W |
| 33.03 | 2.71 | W | 33.96 | 2.64 | W |
| 34.74 | 2.58 | W | 35.84 | 2.51 | W |
| 36.46 | 2.46 | W | | | |

In another preferred embodiment, the X-ray powder diffraction pattern of crystal form B is substantially as shown in FIG. 3.

In another preferred embodiment, the molar ratio of phosphoric acid to the compound of formula X in crystal form B is 1:(0.9-2.1), preferably 1:(1.1-2.1), more preferably 1:1.1.

In another preferred embodiment, the crystal form B further has one or more features selected from the following group:
  (i) In the differential scanning calorimetry analysis spectrum, the starting temperature is 229.7±2° C.; preferably, its differential scanning calorimetry analysis spectrum is substantially as shown in FIG. 4C;
  (ii) Thermogravimetric analysis spectrum is substantially as shown in FIG. 4C;
  (iii) The crystal form B has a melting point of 229° C.-239° C., preferably 231° C.-237° C.

In another preferred embodiment, the crystal form B is in a hydrate form.

In another preferred embodiment, the crystal is C-1 crystalline form of the maleate of compound of formula X, i.e. crystal form C-1, which has an X-ray powder diffraction pattern with diffraction angle 2θ(°) values of the following group C-1-1: 8.73±0.10, 13.37±0.10, 18.08±0.10 and 25.55±0.10 (the highest peak).

In another preferred embodiment, the X-ray powder diffraction pattern of crystal form C-1 further includes 2 or more diffraction angle 2θ(°) values selected from the following group C-1-2: 9.10±0.10, 14.14±0.10, 15.15±0.10, 17.20±0.10, 17.42±0.10, 18.61±0.10, 18.95±0.10, 19.15±0.10, 19.74±0.10, 20.59±0.10, 21.07±0.10, 21.49±0.10, 22.09±0.10, 22.58±0.10, 22.97±0.10, 23.32±0.10, 24.52±0.10, 24.86±0.10, 26.41±0.10, 26.77±0.10, 27.99±0.10, 28.80±0.10, 37.10±0.10.

In another preferred embodiment, the X-ray powder diffraction pattern of crystal form C-1 further includes 2 or more diffraction angle 2θ(°) values selected from the following group C-1-3: 10.12±0.10, 11.56±0.10, 23.85±0.10, 27.21±0.10, 27.55±0.10, 27.85±0.10, 29.54±0.10, 30.27±0.10, 30.76±0.10, 32.93±0.10, 33.47±0.10, 34.20±0.10, 35.03±0.10, 35.34±0.10, 36.04±0.10, 36.47±0.10, 37.56±0.10.

In another preferred embodiment, the X-ray powder diffraction pattern of crystal form C-1 includes six or more or all 2θ(°) values selected from the group C-1-1, C-1-2 and C-1-3 (such as 6, 7, 8, 9, 11, 12, 13, 14, 15, etc.).

In another preferred embodiment, the X-ray powder diffraction pattern of crystal form C-1 has the values shown in Table C-1-2 below:

TABLE C-1-2

| 2θ(°) | d value [Å] | relative intensity I/I$_0$ [%] | 2θ(°) | d value [Å] | relative intensity I/I$_0$ [%] |
|---|---|---|---|---|---|
| 7.14 | 12.38 | W | 8.73 | 10.12 | VS |
| 9.10 | 9.72 | S | 10.12 | 8.74 | M |
| 11.56 | 7.66 | M | 13.37 | 6.62 | VS |
| 14.14 | 6.27 | S | 15.15 | 5.85 | S |
| 17.20 | 5.16 | VS | 17.42 | 5.09 | VS |
| 18.08 | 4.91 | VS | 18.61 | 4.77 | S |
| 18.95 | 4.68 | VS | 19.15 | 4.64 | S |
| 19.74 | 4.50 | VS | 20.59 | 4.31 | S |
| 21.07 | 4.22 | S | 21.49 | 4.13 | VS |
| 22.09 | 4.02 | S | 22.58 | 3.94 | S |
| 22.97 | 3.87 | VS | 23.32 | 3.81 | VS |
| 23.85 | 3.73 | M | 24.52 | 3.63 | VS |
| 24.86 | 3.58 | S | 25.55 | 3.49 | VS |
| 26.41 | 3.38 | S | 26.77 | 3.33 | S |
| 27.21 | 3.28 | M | 27.55 | 3.24 | M |
| 27.85 | 3.20 | M | 27.99 | 3.19 | S |
| 28.80 | 3.10 | S | 29.54 | 3.02 | M |
| 30.27 | 2.95 | M | 30.76 | 2.91 | M |
| 32.93 | 2.72 | M | 33.47 | 2.68 | M |
| 34.20 | 2.62 | M | 35.03 | 2.56 | M |
| 35.34 | 2.54 | M | 36.04 | 2.49 | M |
| 36.47 | 2.46 | M | 37.10 | 2.42 | S |
| 37.56 | 2.40 | M | 38.51 | 2.34 | W |

In another preferred embodiment, the X-ray powder diffraction pattern of crystal form C-1 is substantially as shown in FIG. 5.

In another preferred embodiment, the molar ratio of maleic acid to the compound of formula X in crystal form C-1 is (0.8-1.2):1, preferably (0.9-1.1):1, more preferably 1:1.

In another preferred embodiment, the crystal form C-1 further has one or more features selected from the following group:

(i) In the differential scanning calorimetry analysis spectrum, the starting temperature is 211.6±2° C.; preferably, its differential scanning calorimetry analysis spectrum is substantially as shown in FIG. 6A;

(ii) Thermogravimetric analysis spectrum is substantially as shown in FIG. 6A;

(iii) The crystal form C-1 has a melting point of 211° C.-218° C., preferably 212° C.-216° C.

In another preferred embodiment, the crystal form C-1 is in an anhydrous form.

In another preferred embodiment, the crystal is C-2 crystalline form of the maleate of compound of formula X, i.e. crystal form C-2, which has an X-ray powder diffraction pattern with diffraction angle 2θ(°) values of the following group C-2-1: 7.48±0.10 (the highest peak), 8.60±0.10, 20.63-0.10 and 23.27±0.10.

In another preferred embodiment, the X-ray powder diffraction pattern of crystal form C-2 further includes diffraction angle 2θ(°) values of the following group C-2-2: 17.21±0.10, 18.71-0.10.

In another preferred embodiment, the X-ray powder diffraction pattern of crystal form C-2 further includes 2 or more diffraction angle 2θ(°) values selected from the following group C-2-3: 3.77±0.10, 11.75±0.10, 12.97±0.10, 15.36±0.10, 15.70±0.10, 18.03±0.10, 18.36±0.10, 20.13±0.10, 25.03±0.10.

In another preferred embodiment, the X-ray powder diffraction pattern of crystal form C-2 includes six or more or all 2θ(°) values selected from the group C-2-1, C-2-2 and C-2-3 (such as 6, 7, 8, 9, 10, 11, 12, 13, 14, 15, etc.).

In another preferred embodiment, the X-ray powder diffraction pattern of crystal form C-2 has the values shown in Table C-2-2 below:

TABLE C-2-2

| 2θ(°) | d value [Å] | relative intensity I/I₀ [%] | 2θ(°) | d value [Å] | relative intensity I/I₀ [%] |
|---|---|---|---|---|---|
| 3.77 | 23.42 | M | 7.48 | 11.82 | VS |
| 8.60 | 10.29 | VS | 11.75 | 7.53 | M |
| 12.97 | 6.82 | M | 14.65 | 6.05 | W |
| 15.36 | 5.77 | M | 15.70 | 5.65 | M |
| 17.21 | 5.15 | S | 18.03 | 4.92 | M |
| 18.36 | 4.83 | M | 18.71 | 4.74 | S |
| 20.13 | 4.41 | M | 20.63 | 4.30 | S |
| 21.50 | 4.13 | W | 22.38 | 3.97 | W |
| 23.27 | 3.82 | S | 24.57 | 3.62 | W |
| 25.03 | 3.56 | M | 26.27 | 3.39 | W |
| 26.74 | 3.33 | W | 27.35 | 3.26 | W |
| 32.95 | 2.72 | W | 33.83 | 2.65 | W |

In another preferred embodiment, the X-ray powder diffraction pattern of crystal form C-2 is substantially as shown in FIG. 7.

In another preferred embodiment, the molar ratio of maleic acid to the compound of formula X in crystal form C-2 is (0.8-1.2):1, preferably (0.9-1.1):1, more preferably 1:1.

In another preferred embodiment, the crystal form C-2 further has one or more features selected from the following group:

(i) In the differential scanning calorimetry analysis spectrum, the starting temperature is 208.4±2° C.; preferably, its differential scanning calorimetry analysis spectrum is substantially as shown in FIG. 8;

(ii) Thermogravimetric analysis spectrum is substantially as shown in FIG. 8;

(iii) The crystal form C-2 has a melting point of 208° C.-216° C., preferably 210° C.-214° C.

In another preferred embodiment, the crystal form C-2 is in an anhydrous form.

In another preferred embodiment, the crystal is D crystalline form of the L-malate of compound of formula X, i.e. crystal form D, which has an X-ray powder diffraction pattern with diffraction angle 2θ(°) values of the following group D1: 7.47±0.10, 18.75±0.10, 22.69±0.10 (the highest peak) and 24.39±0.10.

In another preferred embodiment, the X-ray powder diffraction pattern of crystal form D further includes 2 or more diffraction angle 2θ(°) values selected from the following group D2: 17.79±0.10, 18.32±0.10, 20.81±0.10.

In another preferred embodiment, the X-ray powder diffraction pattern of crystal form D further includes 2 or more diffraction angle 2θ(°) values selected from the following group D3: 11.23±0.10, 11.68±0.10, 12.72±0.10, 13.58±0.10, 14.67±0.10, 15.24±0.10, 20.09±0.10, 20.58±0.10, 21.15±0.10, 21.88±0.10, 22.20±0.10, 23.34±0.10, 24.81±0.10, 25.60±0.10, 26.33±0.10, 26.68±0.10, 32.07±0.10.

In another preferred embodiment, the X-ray powder diffraction pattern of crystal form D includes six or more or all 2θ(°) values selected from the group D1, D2 and D3 (such as 6, 7, 8, 9, 10, 11, 12, 13, 14, 15, etc.).

In another preferred embodiment, the X-ray powder diffraction pattern of crystal form D has the values shown in Table D2 below:

TABLE D2

| 2θ(°) | d value [Å] | relative intensity [%] | 2θ(°) | d value [Å] | relative intensity [%] |
|---|---|---|---|---|---|
| 7.47 | 11.83 | S | 11.23 | 7.88 | M |
| 11.68 | 7.58 | M | 12.72 | 6.96 | M |
| 13.58 | 6.52 | M | 14.67 | 6.04 | M |
| 15.24 | 5.81 | M | 17.79 | 4.99 | S |
| 18.32 | 4.84 | S | 18.75 | 4.73 | S |
| 19.72 | 4.50 | W | 20.09 | 4.42 | M |
| 20.58 | 4.32 | M | 20.81 | 4.27 | S |
| 21.15 | 4.20 | M | 21.88 | 4.06 | M |
| 22.20 | 4.00 | M | 22.69 | 3.92 | VS |
| 23.34 | 3.81 | M | 23.77 | 3.74 | W |
| 24.39 | 3.65 | S | 24.81 | 3.59 | M |
| 25.60 | 3.48 | M | 26.33 | 3.38 | M |
| 26.68 | 3.34 | M | 27.16 | 3.28 | W |
| 27.64 | 3.22 | W | 28.87 | 3.09 | W |
| 30.73 | 2.91 | W | 31.36 | 2.85 | W |
| 32.07 | 2.79 | M | 34.62 | 2.59 | W |
| 35.32 | 2.54 | W | 39.29 | 2.29 | W |

In another preferred embodiment, the X-ray powder diffraction pattern of crystal form D is substantially as shown in FIG. 9.

In another preferred embodiment, the molar ratio of L-malic acid to the compound of formula X in crystal form D is (0.5-1.4):1, preferably (0.7-1.3):1, more preferably about 1.3:1.

In another preferred embodiment, the crystal form D further has one or more features selected from the following group:

(i) In the differential scanning calorimetry analysis spectrum, the starting temperature is 201.4±2° C.; preferably, its differential scanning calorimetry analysis spectrum is substantially as shown in FIG. 10A;

(ii) Thermogravimetric analysis spectrum is substantially as shown in FIG. 10A;

(iii) The crystal form D has a melting point of 201° C.-209° C., preferably 202° C.-207° C.

In another preferred embodiment, the crystal form D is in an anhydrous form.

In another preferred embodiment, the crystal is E crystalline form of the adipate of compound of formula X, i.e. crystal form E, which has an X-ray powder diffraction pattern with diffraction angle 2θ(°) values of the following group E1: 7.43±0.10, 18.45±0.10, 21.64±0.10 (the highest peak) and 24.22±0.10.

In another preferred embodiment, the X-ray powder diffraction pattern of crystal form E further includes 2 or more diffraction angle 2θ(°) values selected from the following group E2: 15.66±0.10, 18.83±0.10, 21.16±0.10, 21.39±0.10, 24.38±0.10.

In another preferred embodiment, the X-ray powder diffraction pattern of crystal form E further includes 2 or more diffraction angle 2θ(°) values selected from the following group E3: 11.10±0.10, 11.43±0.10, 12.11±0.10, 13.78±0.10, 15.07±0.10, 15.25±0.10, 17.32±0.10, 20.07±0.10, 20.62±0.10, 20.96±0.10, 23.72±0.10, 25.41±0.10, 25.85±0.10, 26.42±0.10, 27.60±0.10.

In another preferred embodiment, the X-ray powder diffraction pattern of crystal form E includes six or more or all 2θ(°) values selected from the group E1, E2 and E3 (such as 6, 7, 8, 9, 10, 11, 12, 13, 14, 15, etc.).

In another preferred embodiment, the X-ray powder diffraction pattern of crystal form E has the values shown in Table E2 below:

TABLE E2

| 2θ(°) | d value [Å] | relative intensity I/I₀ [%] | 2θ(°) | d value [Å] | relative intensity I/I₀ [%] |
|---|---|---|---|---|---|
| 7.43 | 11.90 | S | 11.10 | 7.97 | M |
| 11.43 | 7.74 | M | 12.11 | 7.31 | M |
| 13.78 | 6.43 | M | 15.07 | 5.88 | M |
| 15.25 | 5.81 | M | 15.66 | 5.66 | S |
| 17.32 | 5.12 | M | 18.45 | 4.81 | VS |
| 18.83 | 4.71 | S | 20.07 | 4.42 | M |
| 20.62 | 4.31 | M | 20.96 | 4.24 | M |
| 21.16 | 4.20 | S | 21.39 | 4.15 | S |
| 21.64 | 4.11 | VS | 23.72 | 3.75 | M |
| 24.22 | 3.67 | S | 24.38 | 3.65 | S |
| 25.41 | 3.50 | M | 25.85 | 3.45 | M |
| 26.42 | 3.37 | M | 27.60 | 3.23 | M |
| 28.73 | 3.11 | W | 32.43 | 2.76 | W |
| 35.37 | 2.54 | W | 37.24 | 2.41 | W |
| 38.72 | 2.33 | W | | | |

In another preferred embodiment, the X-ray powder diffraction pattern of crystal form E is substantially as shown in FIG. 11.

In another preferred embodiment, the molar ratio of adipic acid to the compound of formula X in crystal form E is (0.8-1.2):1, preferably (0.9-1.1):1, more preferably about 1.1:1.

In another preferred embodiment, the crystal form E further has one or more features selected from the following group:
  (i) In the differential scanning calorimetry analysis spectrum, the starting temperature is 203.2±2° C.; preferably, its differential scanning calorimetry analysis spectrum is substantially as shown in FIG. 12A;
  (ii) Thermogravimetric analysis spectrum is substantially as shown in FIG. 12A;
  (iii) The crystal form E has a melting point of 203° C.-208° C., preferably 204° C.-206° C.

In another preferred embodiment, the crystal form E is in an anhydrous form.

In another preferred embodiment, the crystal is I crystalline form of the compound of formula X, which has an X-ray powder diffraction pattern with diffraction angle 2θ(°) values of the group I-1: 8.74±0.10, 9.80±0.10, 15.63±0.10, and 21.38±0.10 (the highest peak).

In another preferred embodiment, the X-ray powder diffraction pattern of crystal form I further includes 2 or more diffraction angle 2θ(°) values selected from the following group I-2: 15.45±0.10, 17.50±0.10, 17.81±0.10, 20.56±0.10, 20.89±0.10, 21.51±0.10, 21.91±0.10, 24.14±0.10, 25.99±0.10, 28.26±0.10.

In another preferred embodiment, the X-ray powder diffraction pattern of crystal form I further includes 2 or more diffraction angle 2θ(°) values selected from the following group I-3: 10.68±0.10, 12.94±0.10, 14.47±0.10, 16.39±0.10, 16.76±0.10, 18.69±0.10, 19.59±0.10, 24.84±0.10, 27.41±0.10, 31.13±0.10, 31.89±0.10.

In another preferred embodiment, the X-ray powder diffraction pattern of crystal form I includes six or more or all 2θ(°) values selected from the group I-1, I-2 and I-3 (such as 6, 7, 8, 9, 10, 11, 12, 13, 14, 15, etc.).

In another preferred embodiment, the X-ray powder diffraction pattern of crystal form I has the values shown in Table I2 below:

TABLE I2

| 2θ(°) | d value [Å] | relative intensity I/I₀ [%] | 2θ(°) | d value [Å] | relative intensity I/I₀ [%] |
|---|---|---|---|---|---|
| 8.74 | 10.12 | VS | 9.80 | 9.02 | VS |
| 10.68 | 8.29 | M | 12.94 | 6.84 | M |
| 14.47 | 6.12 | M | 15.45 | 5.73 | S |
| 15.63 | 5.67 | VS | 16.39 | 5.41 | M |
| 16.76 | 5.29 | M | 17.50 | 5.07 | S |
| 17.81 | 4.98 | S | 18.69 | 4.75 | M |
| 19.59 | 4.53 | M | 20.56 | 4.32 | VS |
| 20.89 | 4.25 | VS | 21.38 | 4.16 | VS |
| 21.51 | 4.13 | VS | 21.91 | 4.06 | S |
| 24.14 | 3.69 | S | 24.84 | 3.58 | M |
| 25.99 | 3.43 | S | 27.41 | 3.25 | M |
| 28.26 | 3.16 | S | 29.49 | 3.03 | W |
| 31.13 | 2.87 | M | 31.89 | 2.81 | M |
| 33.40 | 2.68 | W | 34.81 | 2.58 | W |
| 35.45 | 2.53 | W | 39.02 | 2.31 | W |

In another preferred embodiment, the X-ray powder diffraction pattern of crystal form I is substantially as shown in FIG. 13.

In another preferred embodiment, the crystal form I further has one or more features selected from the following group:
  (i) In the differential scanning calorimetry analysis spectrum, the starting temperature is 159.6±2° C.; preferably, its differential scanning calorimetry analysis spectrum is substantially as shown in FIG. 14;
  (ii) Thermogravimetric analysis spectrum is substantially as shown in FIG. 14;
  (iii) The crystal form I has a melting point of 159° C.-165° C., preferably 160° C.-163° C.

In another preferred embodiment, the crystal form I is in an anhydrous form.

In another preferred embodiment, the crystal is II crystalline form of the compound of formula X, which has an X-ray powder diffraction pattern with diffraction angle 2θ(°) values of the group II-1: 9.47±0.10 (the highest peak), 17.34±0.10, 18.87±0.10, and 23.89±0.10.

In another preferred embodiment, the X-ray powder diffraction pattern of crystal form II further includes 2 or more diffraction angle 2θ(°) values selected from the following group II-2: 6.61±0.10, 12.06±0.10, 16.96±0.10, 19.19±0.10, 19.84±0.10, 20.66±0.10, 20.96±0.10, 24.22±0.10, 28.93±0.10.

In another preferred embodiment, the X-ray powder diffraction pattern of crystal form II includes six or more or all 2θ(°) values selected from the group II-1, II-2 (such as 6, 7, 8, 9, 10, 11, 12, 13, 14, 15, etc.).

In another preferred embodiment, the X-ray powder diffraction pattern of crystal form II has the values shown in Table II2 below:

TABLE II2

| 2θ(°) | d value [Å] | relative intensity I/I₀ [%] | 2θ(°) | d value [Å] | relative intensity I/I₀ [%] |
|---|---|---|---|---|---|
| 6.61 | 13.37 | M | 9.47 | 9.34 | VS |
| 10.74 | 8.24 | W | 12.06 | 7.34 | M |
| 12.54 | 7.06 | W | 13.23 | 6.69 | W |
| 13.54 | 6.54 | W | 14.36 | 6.17 | W |
| 15.12 | 5.86 | W | 16.96 | 5.23 | S |
| 17.34 | 5.11 | S | 18.87 | 4.70 | S |
| 19.19 | 4.62 | M | 19.84 | 4.47 | M |
| 20.66 | 4.30 | M | 20.96 | 4.24 | M |
| 22.03 | 4.03 | W | 23.89 | 3.72 | S |
| 24.22 | 3.67 | M | 24.73 | 3.60 | W |
| 25.53 | 3.49 | W | 26.21 | 3.40 | W |
| 27.42 | 3.25 | W | 28.07 | 3.18 | W |
| 28.93 | 3.09 | M | 29.57 | 3.02 | W |
| 30.43 | 2.94 | W | 32.61 | 2.75 | W |
| 33.36 | 2.69 | W | 34.96 | 2.57 | W |
| 38.93 | 2.31 | W | | | |

In another preferred embodiment, the X-ray powder diffraction pattern of crystal form II is substantially as shown in FIG. 15.

In another preferred embodiment, the crystal form II further has one or more features selected from the following group:
(i) In the differential scanning calorimetry analysis spectrum, the starting temperature is 159.9±2° C.; preferably, its differential scanning calorimetry analysis spectrum is substantially as shown in FIG. 16;
(ii) Thermogravimetric analysis spectrum is substantially as shown in FIG. 16;
(iii) The crystal form II has a melting point of 159° C.-164° C., preferably 160° C.-163° C.

In another preferred embodiment, the crystal form II is in a hydrate form, preferably in a dihydrate form.

In another preferred embodiment, the crystal is III crystalline form of the compound of formula X, which has an X-ray powder diffraction pattern with diffraction angle 2θ(°) values of the group III-1: 9.72±0.10, 18.41±0.10, 23.89±0.10 (the highest peak) and 28.02±0.10.

In another preferred embodiment, the X-ray powder diffraction pattern of crystal form III further includes 2 or more diffraction angle 2θ(°) values selected from the following group III-2: 11.78±0.10, 16.34±0.10, 16.57±0.10, 17.54±0.10, 18.19±0.10, 20.06±0.10, 21.33±0.10, 23.68±0.10, 25.05±0.10.

In another preferred embodiment, the X-ray powder diffraction pattern of crystal form III further includes 2 or more diffraction angle 2θ(°) values selected from the following group III-3: 6.68±0.10, 8.25±0.10, 13.19±0.10, 13.92±0.10, 15.54±0.10, 19.58±0.10, 21.66±0.10, 22.39±0.10, 22.96±0.10, 24.26±0.10, 26.34±0.10, 27.36±0.10, 29.06±0.10, 29.41±0.10, 31.00±0.10, 34.62±0.10.

In another preferred embodiment, the X-ray powder diffraction pattern of crystal form III includes six or more or all 2θ(°) values selected from the group III-1, III-2 and III-3 (such as 6, 7, 8, 9, 10, 11, 12, 13, 14, 15, etc.).

In another preferred embodiment, the X-ray powder diffraction pattern of crystal form III has the values shown in Table III2 below:

TABLE III2

| 2θ(°) | d value [Å] | relative intensity I/I₀ [%] | 2θ(°) | d value [Å] | relative intensity I/I₀ [%] |
|---|---|---|---|---|---|
| 6.68 | 13.23 | M | 8.25 | 10.72 | M |
| 9.72 | 9.10 | VS | 11.78 | 7.51 | S |
| 13.19 | 6.71 | M | 13.92 | 6.36 | M |
| 15.54 | 5.70 | M | 16.34 | 5.42 | S |
| 16.57 | 5.35 | S | 17.54 | 5.06 | S |
| 18.19 | 4.88 | S | 18.41 | 4.82 | VS |
| 19.58 | 4.53 | M | 20.06 | 4.43 | S |
| 21.33 | 4.17 | S | 21.66 | 4.10 | M |
| 22.39 | 3.97 | M | 22.96 | 3.87 | M |
| 23.68 | 3.76 | S | 23.89 | 3.72 | VS |
| 24.26 | 3.67 | M | 25.05 | 3.55 | S |
| 26.34 | 3.38 | M | 27.36 | 3.26 | M |
| 28.02 | 3.18 | VS | 29.06 | 3.07 | M |
| 29.41 | 3.04 | M | 31.00 | 2.88 | M |
| 33.19 | 2.70 | W | 34.62 | 2.59 | M |
| 37.97 | 2.37 | W | 38.77 | 2.32 | W |

In another preferred embodiment, the X-ray powder diffraction pattern of crystal form III is substantially as shown in FIG. 17.

In another preferred embodiment, the crystal form III further has one or more features selected from the following group:
(i) In the differential scanning calorimetry analysis spectrum, the starting temperature is 159.9±2° C.; preferably, its differential scanning calorimetry analysis spectrum is substantially as shown in FIG. 18A;
(ii) Thermogravimetric analysis spectrum is substantially as shown in FIG. 18A;
(iii) The crystal form III has a melting point of 159° C.-164° C., preferably 160° C.-162° C.

In another preferred embodiment, the crystal form III is in a solvate form, preferably a methanol solvate.

In another preferred embodiment, the crystal is IV crystalline form of the compound of formula X, which has an X-ray powder diffraction pattern with diffraction angle 2θ(°) values of the group IV-1: 7.69±0.10 (the highest peak), 18.90±0.10.

In another preferred embodiment, the X-ray powder diffraction pattern of crystal form IV further includes 2 or more diffraction angle 2θ(°) values selected from the following group IV-2: 5.38±0.10, 9.43±0.10, 13.31±0.10, 18.06±0.10, 23.19±0.10, 24.18±0.10.

In another preferred embodiment, the X-ray powder diffraction pattern of crystal form IV includes four or more or all 2θ(°) values selected from the group IV-1 and IV-2 (such as 4, 5, 6, 7, 8, 9, 10, 11, 12, 13, etc.).

In another preferred embodiment, the X-ray powder diffraction pattern of crystal form IV has the values shown in Table IV2 below:

TABLE IV2

| 2θ(°) | d value [Å] | relative intensity [%] | 2θ(°) | d value [Å] | relative intensity [%] |
|---|---|---|---|---|---|
| 5.38 | 16.43 | M | 7.69 | 11.50 | VS |
| 9.43 | 9.38 | M | 13.31 | 6.65 | M |
| 15.28 | 5.80 | W | 16.31 | 5.44 | W |
| 18.06 | 4.91 | M | 18.90 | 4.70 | VS |
| 20.35 | 4.36 | W | 23.19 | 3.84 | M |
| 24.18 | 3.68 | M | 24.64 | 3.61 | W |
| 27.80 | 3.21 | W | | | |

In another preferred embodiment, the X-ray powder diffraction pattern of crystal form IV is substantially as shown in FIG. 19.

In another preferred embodiment, the crystal form IV further has one or more features selected from the following group:
(i) In the differential scanning calorimetry analysis spectrum, the starting temperature is 159.5±2° C.; preferably, its differential scanning calorimetry analysis spectrum is substantially as shown in FIG. 20;
(ii) Thermogravimetric analysis spectrum is substantially as shown in FIG. 20;
(iii) The crystal form IV has a melting point of 159° C.-164° C., preferably 160° C.-162° C.

In another preferred embodiment, the crystal form IV is in a hydrate form.

In another preferred embodiment, the crystal is V crystalline form of the compound of formula X, which has an X-ray powder diffraction pattern with diffraction angle 2θ(°) values of the group V-1: 8.28±0.10, 8.89±0.10 (the highest peak), 9.44±0.10, 17.76±0.10.

In another preferred embodiment, the X-ray powder diffraction pattern of crystal form V further includes 2 or more diffraction angle 2θ(°) values selected from the following group V-2: 14.01±0.10, 15.39±0.10, 16.55±0.10, 18.46±0.10, 18.91±0.10, 21.71±0.10, 22.91±0.10, 23.24±0.10, 24.87±0.10.

In another preferred embodiment, the X-ray powder diffraction pattern of crystal form V includes six or more or all 2θ(°) values selected from the group V-1 and V-2 (such as 6, 7, 8, 9, 10, 11, 12, 13, 14, 15, etc.).

In another preferred embodiment, the X-ray powder diffraction pattern of crystal form V has the values shown in Table V2 below:

TABLE V2

| 2θ(°) | d value [Å] | relative intensity I/I₀ [%] | 2θ(°) | d value [Å] | relative intensity I/I₀ [%] |
|---|---|---|---|---|---|
| 8.28 | 10.68 | VS | 8.89 | 9.95 | VS |
| 9.44 | 9.36 | S | 11.47 | 7.71 | W |
| 14.01 | 6.32 | M | 14.55 | 6.09 | W |
| 15.39 | 5.76 | M | 16.36 | 5.42 | W |
| 16.55 | 5.36 | M | 16.81 | 5.27 | W |
| 17.76 | 4.99 | S | 18.46 | 4.81 | M |
| 18.91 | 4.69 | M | 19.61 | 4.53 | W |
| 21.71 | 4.09 | M | 22.29 | 3.99 | W |
| 22.91 | 3.88 | M | 23.24 | 3.83 | M |
| 24.28 | 3.67 | W | 24.87 | 3.58 | M |
| 26.75 | 3.33 | W | 27.20 | 3.28 | W |
| 30.03 | 2.98 | W | 30.72 | 2.91 | W |
| 38.31 | 2.35 | W | | | |

In another preferred embodiment, the X-ray powder diffraction pattern of crystal form V is substantially as shown in FIG. 21.

In another preferred embodiment, the crystal form V further has one or more features selected from the following group:
(i) In the differential scanning calorimetry analysis spectrum, the starting temperature is 150.7±2° C.; preferably, its differential scanning calorimetry analysis spectrum is substantially as shown in FIG. 22A;
(ii) Thermogravimetric analysis spectrum is substantially as shown in FIG. 22A;
(iii) The crystal form V has a melting point of 149° C.-157° C., preferably 151° C.-155° C.

In another preferred embodiment, the crystal form V is in a solvate form, preferably in an ethyl acetate solvate form.

In the second aspect of the present invention, a process for preparing the compound of formula X, or its pharmaceutically acceptable salt of the first aspect of the present invention is provided, and the process comprises the steps:
(1) Compound I-2 is reacted with compound 3a in an inert solvent to form the compound of formula X; and

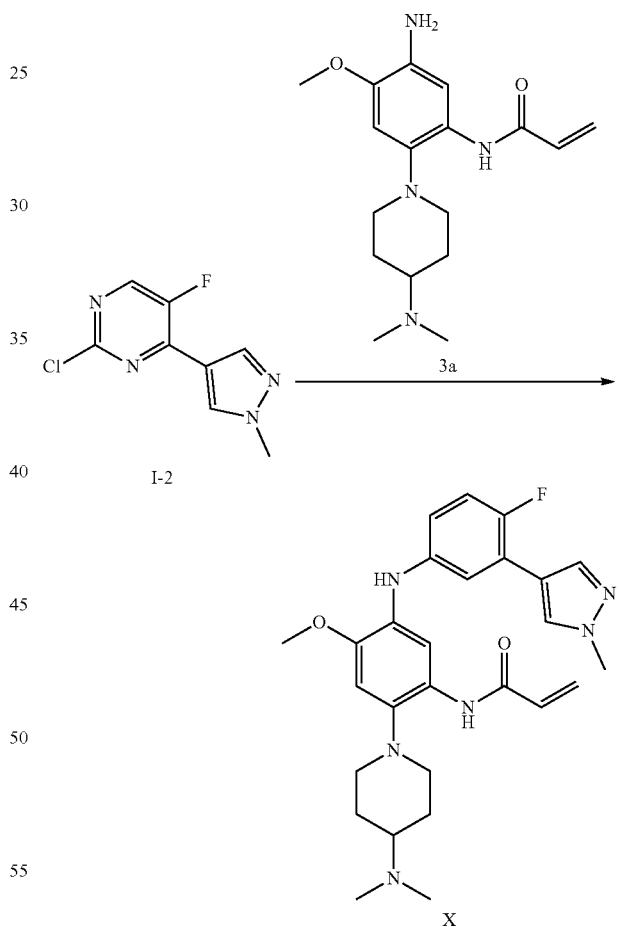

(2) The compound of formula X is optionally reacted with an acid to form a pharmaceutically acceptable salt;
(3) the compound of formula X, or a pharmaceutically acceptable salt thereof formed in step (1) or (2) is optionally crystallized to obtain a crystal.

In another preferred embodiment, in step (1), the inert solvent is selected from the group consisting of 1,4-dioxane, dimethylsulfoxide and DMF.

In another preferred embodiment, in the step (1), the process further comprises the step:

1-1) The formed compound of formula X is added into an organic solvent, and dissolved to form a solution by heating and refluxing;

1-2) water is added to the solution such that the volume ratio of the organic solvent to water is (1-2):1 (preferably (1.2-1.8):1);

1-3) the solution is cooled, and the solid is precipitated, filtered and washed with water to obtain the compound of formula X.

In another preferred embodiment, in step 1-1), the organic solvent is selected from the group consisting of methanol, ethanol, propanol, isopropanol, butanol, acetone, acetonitrile, tetrahydrofuran, propylene glycol or a mixture thereof, preferably ethanol.

In another preferred embodiment, in step 1-1), the concentration of the compound of formula X in an organic solvent is 0.1-0.5 g/mL.

In another preferred embodiment, the process comprises any of the following sub-processes (A)-(E) and (I)-(V):

(A) the crystal is A crystalline form of the hydrochloride of compound of formula X, i.e. crystal form A, and the step (3) comprises crystallization process of the compound of formula X in an organic solvent in the presence of hydrochloric acid, thereby forming crystal form A;

In another preferred embodiment, in sub-process (A), the organic solvent is selected from the group consisting of methanol, ethanol, propanol, isopropanol, butanol, acetone, acetonitrile, tetrahydrofuran, propylene glycol or mixtures thereof, and preferably, the organic solvent is acetonitrile.

In another preferred embodiment, in sub-process (A), the concentration of hydrochloric acid in organic solvent is 0.1 to 0.5 g/mL.

In another preferred embodiment, in sub-process (A), the molar ratio of hydrochloric acid to the compound of formula X is (1-2):1, preferably (1-1.2):1.

In another preferred embodiment, in sub-process (A), the crystallization process is suspension stirring.

In another preferred embodiment, in sub-process (A), the temperature for crystallization process is 5-30° C., preferably 10-20° C.

In another preferred embodiment, in sub-process (A), the time for crystallization process is 1 to 72 hours, preferably 10 to 50 hours.

(B) the crystal is B crystalline form of the phosphate of compound of formula X, i.e. crystal form B, and the step (3) comprises crystallization process of the compound of formula X in an organic solvent in the presence of phosphoric acid, thereby forming crystal form B;

In another preferred embodiment, in sub-process (B), the organic solvent is selected from the group consisting of methanol, ethanol, propanol, isopropanol, butanol, acetone, acetonitrile, tetrahydrofuran, propylene glycol or mixtures thereof, and preferably, the organic solvent is acetonitrile.

In another preferred embodiment, in sub-process (B), the concentration of phosphoric acid in organic solvent is 0.1 to 0.5 g/mL.

In another preferred embodiment, in sub-process (B), the molar ratio of phosphoric acid to the compound of formula X is (1-2):1, preferably (1-1.2):1.

In another preferred embodiment, in sub-process (B), the crystallization process is suspension stirring.

In another preferred embodiment, in sub-process (B), the temperature for crystallization process is 5-30° C., preferably 10-20° C.

In another preferred embodiment, in sub-process (B), the time for crystallization process is 1 to 72 hours, preferably 10 to 50 hours.

(C-1-1) the crystal is C-1 crystalline form of the maleate of compound of formula X, i.e. crystal form C-1, and the step (3) comprises crystallization process of the compound of formula X in an organic solvent in the presence of maleic acid, thereby forming crystal form C-1;

In another preferred embodiment, in sub-process (C-1-1), the organic solvent is selected from the group consisting of methanol, ethanol, propanol, isopropanol, butanol, acetone, acetonitrile, tetrahydrofuran, propylene glycol or mixtures thereof, and preferably, the organic solvent is acetonitrile.

In another preferred embodiment, in sub-process (C-1-1), the feed ratio (m:v) of maleic acid to the organic solvent is 5-12 mg/mL.

In another preferred embodiment, in sub-process (C-1-1), the molar ratio of maleic acid to the compound of formula X is (1-2):1, preferably (1-1.2):1.

In another preferred embodiment, in sub-process (C-1-1), the crystallization process is suspension stirring.

In another preferred embodiment, in sub-process (C-1-1), the temperature for crystallization process is 5-30° C., preferably 10-20° C.

In another preferred embodiment, in sub-process (C-1-1), the time for crystallization process is 1 to 72 hours, preferably 10 to 50 hours.

(C-1-2) the crystal is a C-1 crystalline form of the maleate of compound of formula X, i.e. crystal form C-1, the step (3) comprises adding maleic acid to the organic solvent in reflux of the compound of formula X, and cooling with stirring, thereby forming crystal form C-1;

In another preferred embodiment, in sub-process (C-1-2), the organic solvent is selected from the group consisting of methanol, ethanol, propanol, isopropanol, butanol, acetone, acetonitrile, tetrahydrofuran and propylene glycol and the mixture thereof, and preferably, the organic solvent is methanol, ethanol, acetone, acetonitrile.

In another preferred embodiment, in sub-process (C-1-2), the molar ratio of maleic acid to the compound of formula X is (1-3):1, preferably (1-1.5):1.

In another preferred embodiment, in sub-process (C-1-2), the concentration of the compound of formula X in organic solvent is 0.1-1 g/mL, preferably 0.2-0.6 g/mL.

In another preferred embodiment, in sub-process (C-1-2), the cooling time is 1-10 hours.

In another preferred embodiment, in sub-process (C-1-2), the solvent is cooled to 5-15° C.

(D) the crystal is D crystalline form of the L-malate of compound of formula X, i.e. crystal form D, and the step (3) comprises crystallization process of the compound of formula X in an organic solvent in the presence of L-malic acid, thereby forming crystal form D;

In another preferred embodiment, in sub-process (D), the organic solvent is selected from the group consisting of methanol, ethanol, propanol, isopropanol, butanol, acetone, acetonitrile, tetrahydrofuran, propylene glycol or mixtures thereof, and preferably, the organic solvent is acetonitrile.

In another preferred embodiment, in sub-process (D), the feed ratio (m:v) of L-malic acid to the organic solvent is 5-12 mg/mL.

In another preferred embodiment, in sub-process (D), the molar ratio of L-malic acid to the compound of formula X is (1-2):1, preferably (1-1.2):1.

In another preferred embodiment, in sub-process (D), the crystallization process is suspension stirring.

In another preferred embodiment, in sub-process (D), the temperature for crystallization process is 5-30° C., preferably 10-20° C.

In another preferred embodiment, in sub-process (D), the time for crystallization process is 1 to 72 hours, preferably 10 to 50 hours.

(E) the crystal is E crystalline form of the adipate of compound of formula X, i.e. crystal form E, and the step (3) comprises crystallization process of the compound of formula X in an organic solvent in the presence of adipic acid, thereby forming crystal form E;

In another preferred embodiment, in sub-process (E), the organic solvent is selected from the group consisting of methanol, ethanol, propanol, isopropanol, butanol, acetone, acetonitrile, tetrahydrofuran, propylene glycol or mixtures thereof, and preferably, the organic solvent is acetonitrile.

In another preferred embodiment, in sub-process (E), the feed ratio (m:v) of adipic acid to the organic solvent is 5-12 mg/mL.

In another preferred embodiment, in sub-process (E), the molar ratio of adipic acid to the compound of formula X is (1-2):1, preferably (1-1.2):1.

In another preferred embodiment, in sub-process (E), the crystallization process is suspension stirring.

In another preferred embodiment, in sub-process (E), the temperature for crystallization process is 5-30° C., preferably 10-20° C.

In another preferred embodiment, in sub-process (E), the time for crystallization process is 1 to 72 hours, preferably 10 to 50 hours.

(I) the crystal is crystal form I of the compound of formula X, and the step (3) comprises crystallization process of the compound of formula X in an solvent, thereby forming crystal form I.

In another preferred embodiment, in sub-process (I), the solvent is selected from the group consisting of water, methanol, ethanol, propanol, isopropanol, butanol, acetone, acetonitrile, tetrahydrofuran, propylene glycol, ethyl acetate, methyl isobutyl ketone, isopropyl acetate, 2-methyl tetrahydrofuran, dichloromethane, methyl tert-butyl ether, dimethylsulfoxide, toluene, N, N-dimethylacetamide, N-methylpyrrolidone, or a mixture thereof.

In another preferred embodiment, in sub-process (I), the solvent is selected from the group consisting of methanol, isopropanol, methyl isobutyl ketone, ethyl acetate, isopropyl acetate, 2-methyltetrahydrofuran, acetonitrile, dichloromethane/methyl tert-butyl ether (V:V is 1:1-1:4), dimethylsulfoxide/toluene (V:V is 1:1 to 1:4), N-methylpyrrolidone/methyl tert-butyl ether (V:V is 1:1 to 1:4), water/acetone.

In another preferred embodiment, in sub-process (I), the crystallization process is suspension stirring or slow volatilization.

In another preferred embodiment, in sub-process (I), the temperature for crystallization process is 5-30° C., preferably 10-20° C.

In another preferred embodiment, in sub-process (I), the time for crystallization process is 1 to 10 days, preferably 4 to 8 days.

(II) the crystal is crystal form II of the compound of formula X, and the step (3) comprises crystallization process of the compound of formula X in an solvent, thereby forming crystal form II.

In another preferred embodiment, in sub-process (II), the solvent is selected from the group consisting of water, methanol, ethanol, propanol, isopropanol, butanol, acetone, acetonitrile, tetrahydrofuran, propylene glycol, ethyl acetate, methyl isobutyl ketone, isopropyl acetate, 2-methyl tetrahydrofuran, dichloromethane, methyl tert-butyl ether, dimethylsulfoxide, toluene, N, N-dimethylacetamide, N-methylpyrrolidone, or a mixture thereof.

In another preferred embodiment, in sub-process (II), the solvent is selected from the group consisting of methanol, isopropanol, methyl isobutyl ketone, ethyl acetate, isopropyl acetate, 2-methyltetrahydrofuran, acetonitrile, methylene chloride/methyl tert-butyl ether (V:V) 1:1-1:4), dimethyl sulfoxide/toluene (V:V is 1:1-1:4), N,N-dimethylacetamide/isopropyl acetate (V:V is 1:1 to 1:4), N-methylpyrrolidone/methyl t-butyl ether (V:V is 1:1 to 1:4), water/acetone.

In another preferred embodiment, in sub-process (II), the crystallization process is suspension stirring or addition of an anti-solvent.

In another preferred embodiment, in sub-process (II), the temperature for crystallization process is 5-30° C., preferably 10-20° C.

In another preferred embodiment, in sub-process (II), the time for crystallization process is 1 to 10 days, preferably 4 to 8 days.

(III) the crystal is crystal form III of the compound of formula X, and the step (3) comprises crystallization process of the compound of formula X in an solvent, thereby forming crystal form III.

In another preferred embodiment, in sub-process (III), the solvent is selected from the group consisting of water, methanol, ethanol, propanol, isopropanol, butanol, acetone, acetonitrile, tetrahydrofuran, propylene glycol, ethyl acetate, methyl isobutyl ketone, isopropyl acetate, 2-methyl tetrahydrofuran, dichloromethane, methyl tert-butyl ether, dimethylsulfoxide, toluene, N, N-dimethylacetamide, N-methylpyrrolidone, or a mixture thereof.

In another preferred embodiment, in sub-process (III), the solvent is selected from the group consisting of methanol, isopropanol, methyl isobutyl ketone, ethyl acetate, isopropyl acetate, 2-methyltetrahydrofuran, acetonitrile, methylene chloride/methyl tert-butyl ether (V:V) 1:1-1:4), dimethyl sulfoxide/toluene (V:V is 1:1-1:4), N,N-dimethylacetamide/isopropyl acetate (V:V is 1:1 to 1:4), N-methylpyrrolidone/methyl t-butyl ether (V:V is 1:1 to 1:4), water/acetone.

In another preferred embodiment, in sub-process (III), the crystallization process is suspension stirring.

In another preferred embodiment, in sub-process (III), the temperature for crystallization process is 5-30° C., preferably 10-20° C.

In another preferred embodiment, in sub-process (III), the time for crystallization process is 1 to 5 days, preferably 2 to 4 days.

(IV) the crystal is crystal form IV of the compound of formula X, and the step (3) comprises crystallization process of the compound of formula X in an solvent, thereby forming crystal form IV.

In another preferred embodiment, in sub-process (IV), the solvent is selected from the group consisting of methanol, ethanol, propanol, isopropanol, butanol, acetone, acetonitrile, tetrahydrofuran, propylene glycol, ethyl acetate, 1,4-dioxane, 2-methyltetrahydrofuran, or a mixture thereof.

In another preferred embodiment, in sub-process (IV), the crystallization process is slow volatilization.

In another preferred embodiment, in sub-process (IV), the temperature for crystallization process is 5-30° C., preferably 10-20° C.

In another preferred embodiment, in sub-process (IV), the time for crystallization process is 1 to 10 days, preferably 4 to 8 days.

(V) the crystal is crystal form V of the compound of formula X, and the step (3) comprises crystallization process of the compound of formula X in an solvent, thereby forming crystal form V.

In another preferred embodiment, in sub-process (V), the solvent is selected from the group consisting of methanol, ethanol, propanol, isopropanol, butanol, acetone, acetonitrile, tetrahydrofuran, propylene glycol, ethyl acetate, 1,4-dioxane, 2-methyltetrahydrofuran, or a mixture thereof.

In another preferred embodiment, in sub-process (V), the crystallization process is slow volatilization or addition of anti-solvent.

In another preferred embodiment, in sub-process (II), the temperature for crystallization process is 5-30° C., preferably 10-20° C.

In another preferred embodiment, in sub-process (II), the time for crystallization process is 1 to 10 days, preferably 4 to 6 days.

In another preferred embodiment, the crystal is a crystalline form of the compound of formula X, and
1) the compound of formula X is crystallized in solvent F to obtain crystal form I, II, or III; or
2) the compound of formula X is crystallized in solvent H to obtain crystal form IV or V;
wherein the solvent F is selected from the group consisting of water, methanol, ethanol, propanol, isopropanol, butanol, acetone, acetonitrile, tetrahydrofuran, propylene glycol, ethyl acetate, methyl isobutyl ketone, isopropyl acetate, 2-methyltetrahydrofuran, dichloromethane, methyl tert-butyl ether, dimethylsulfoxide, toluene, N,N-dimethylacetamide, N-methylpyrrolidone or a mixture thereof.

In another preferred embodiment, the solvent F is selected from the group consisting of methanol, isopropanol, methyl isobutyl ketone, ethyl acetate, isopropyl acetate, 2-methyltetrahydrofuran, acetonitrile, dichloromethane/methyl t-butyl ether (V:V is 1:1 to 1:4), dimethylsulfoxide/toluene (V:V is 1:1 to 1:4), N,N-dimethylacetamide/isopropyl acetate (V:V 1:1-1:4), N-methylpyrrolidone/methyl tert-butyl ether (V:V 1:1-1:4), water/acetone.

The solvent H is selected from the group consisting of methanol, ethanol, propanol, isopropanol, butanol, acetone, acetonitrile, tetrahydrofuran, propylene glycol, ethyl acetate, 1,4-dioxane, 2-methyltetrahydrofuran, or a mixture thereof.

In another preferred embodiment, the crystallization includes suspension stirring crystallization, concentration crystallization, supersaturation crystallization, evaporation crystallization, volatilization crystallization, or a combination thereof.

In the third aspect of the invention, a pharmaceutical composition is provided, comprising:
(a) the compound of formula X, a pharmaceutically acceptable salt, or a prodrug thereof according to any one of the first aspect of the invention; and (b) a pharmaceutically acceptable carrier.

In another preferred embodiment, the pharmaceutical composition further comprises one or more other drugs for treating and/or preventing tumors.

In another preferred embodiment, the other drug is one or more selected from the group consisting of gefitinib, erlotinib, icotinib, lapatinib, XL647, NVP-DEE-788, DRRY-334543, EKB-569, BIBW2992, HKI272, BMS-690514, CI-1033, vandetanib, PF00299804, WZ4002, cetuximab, trastuzumab, panitumumab, matuzumab, nimotuzumab, zalutumumab, pertuzumab, MDX-214, CDX-110, IMC-11F8, ZemDb, Her2 vaccine PX 1041, HSP90 inhibitors, CNF2024, tanespimycin, alvespimycin, IPI-504, SNX-5422, NVP-DUY922, or a combination thereof.

In the fourth aspect of the present invention, the use of the compound of the first aspect of the present invention, or a pharmaceutically acceptable salt, or prodrug thereof, or a pharmaceutical composition of the third aspect of the present invention for the manufacture of a medicament for regulating EGFR tyrosine kinase or treating EGFR-related diseases is provided.

In another preferred embodiment, the EGFR-related disease is selected from the group consisting of cancer, diabetes, immune system diseases, neurodegenerative diseases, cardiovascular diseases, diseases with acquired resistance during treatment using EGFR modulators.

In another preferred embodiment, the diseases with acquired resistance are caused by the T790 mutations encoded by EGFR exon 20, or by the inclusion of T790 mutations encoded by EGFR exon 20.

It should be understood that each of the above technical features of the invention and each technical feature specifically described below (such as in Examples) can be combined with each other within the scope of the present invention so as to constitute new or preferred technical solutions which need not be specified again herein.

DETAIL DESCRIPTION OF INVENTION

Figure 1:
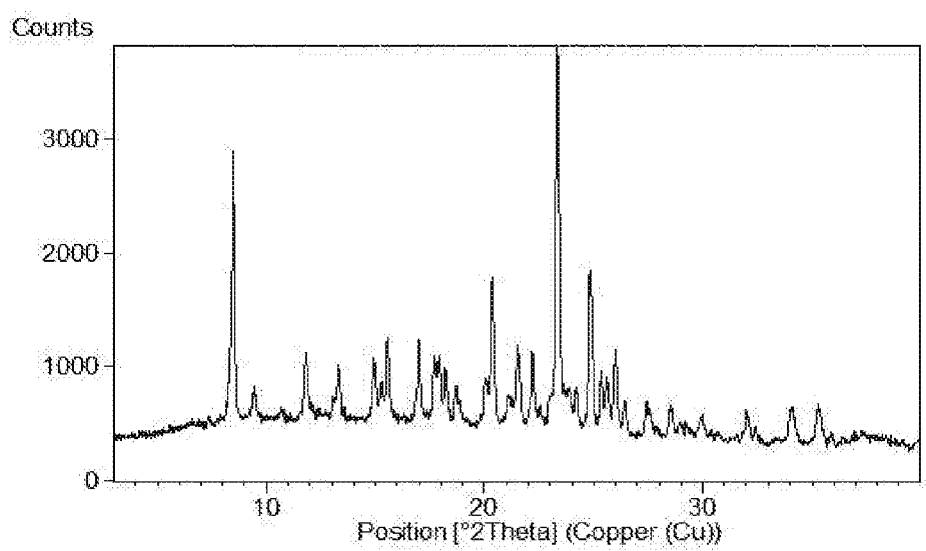
FIG. 1 shows the XRPD pattern of crystal form A.

Inventors discovered a series of free base polymorphs, salts and salt polymorphs of the compound of formula X after a long and intensive study. The in vitro enzyme and cell growth inhibition experiments showed that the free base of the compound of formula X exhibited a strong inhibitory activity against EGFR T790M mutant enzyme and cells, but had a weak inhibitory activity against EGFR wild type enzyme and cells, and showed low cytotoxicity, the compound of formula X is therefore an ideal third generation of EGFR mutant selective inhibitor. The study also found that a series of free base polymorphs, salts and salt polymorphs of the compound of formula X not only had good physical and chemical stability but also had good pharmacological activity in vivo and in vitro, and therefore could be further developed into drugs.

Term

As used herein, the term "compound of the present invention" includes the compound of formula X of the present invention, a pharmaceutically acceptable salt of the compound of formula X of the present invention, and a polymorph of the present invention.

Compound of Formula X

In the present invention, "compound of formula X" or "compound shown as formula X" can be used interchangeably. Unless otherwise specified, the term generally refers to the free base form.

In the present invention, the compound of formula X is N-(2-(4-(dimethylamino) piperidin-1-yl)-5-(5-fluoro-4-(1-methyl-1H-pyrazol-4-yl)pyrimidin-2-ylamino)-4-methoxyphenyl)acrylamide, which has good selective inhibitory activity against T790M mutant EGFR and lower cytotoxicity, as well as favorable metabolic profiles.

In the present invention, "the free base sample" or "free base" refers to the free base of the compound of Formula X prepared in Example 1.

Pharmaceutically Acceptable Salt of the Compound of Formula X

In the present invention, the pharmaceutically acceptable salts are preferably selected from the group consisting of hydrochloride, sulfate, phosphate, acetate, L-lactate, maleate, fumarate, succinate, L-malate, adipate, L-tartrate, hippurate, citrate, mucate, glycolate, glucuronate, benzoate, gentisate, nicotinate, ethanedisulfonate, oxalate, methanesulfonate, benzenesulfonate, hydroxyethanesulfonate and hydrobromide.

Polymorphs

Solid exists in amorphous form or in crystalline form. In the case of crystal form, the molecules are localized in the three-dimensional lattice sites. When a compound is crystallized from a solution or slurry, it can be crystallized in different space lattice arrangement (this property is called "polymorphism") to form crystals with different crystalline forms, each of which is called as "polymorphs." Different polymorphs of a given substance may differ from each other in one or more physical properties (such as solubility and dissolution rate, true specific gravity, crystalline form, packing pattern, flowability and/or solid state stability).

Crystallization

Crystallization on the production scale can be accomplished by manipulating a solution such that the solubility limit of the interested compound is exceeded. This can be done in a number of ways, for example, by dissolving the compound at a relatively high temperature and then cooling the solution below a saturation limit, or by boiling, evaporating at ordinary pressure, drying under vacuum or by some other means to reduce the liquid volume. The solubility of the interested compound may be reduced by adding an anti-solvent or a solvent in which the compound has a low solubility or a mixture of such solvents. An alternative method is to adjust the pH to reduce the solubility. See Crystallization, Third Edition, J W Mullens, Butterworth-Heineman Ltd., 1993, ISBN 0750611294 for a detailed description of crystallization.

As used herein, the term "suspension stirring" means a way to get crystals by mixing the compound of formula X with the corresponding acid or a solution of the corresponding acid to form a turbid solution, or by mixing the compound of formula X with a suitable solvent to form a turbid solution before stirring. Suitable solvents may be water or organic solvents.

As used herein, the term "slow volatilization" means a way to get crystals by placing a solution of the compound of formula X or a solution of the compound of formula X and the corresponding acid at a certain temperature for slow volatilization of the solvent.

As used herein, the term "addition of anti-solvent" means a way to get crystals by adding a suitable solvent to a solution of the compound of formula X and precipitating the crystals.

If salt formation and crystallization are expected to occur at the same time, the addition of an appropriate acid or base can result in the direct crystallization of the desired salt if the salt is less soluble in the reaction medium than the raw material. Likewise, in a medium in which the solubility of the desired final form is lower than that of reactant, the final product can be directly crystallized when the synthetic reaction is completed.

Optimization of crystallization can include inoculation of the crystal of desired form as a seed into the crystallization medium. In addition, many crystallization methods include a combination of the above strategies. One example is to dissolve the interested compound in a solvent at a high temperature, followed by the addition of an antisolvent with a suitable volume in a controlled manner so that the system is just below saturation level. At this moment, the seed of desired form (the integrity of the seed is kept) can be added and the system is cooled to complete the crystallization.

As used herein, the term "room temperature" generally means 4-30° C., preferably 20±5° C.

Polymorphs of the Present Invention

As used herein, "crystals of the present invention", "crystalline form of the present invention", "polymorphs of the present invention" and the like can be used interchangeably and include the polymorphs of the compound of formula X of the present invention and the polymorphs of a pharmaceutically acceptable salt of the compound of formula X of the present invention.

In the present invention, "polymorph of the compound of formula X" and "polymorph of the free base of the compound of formula X" are used interchangeably.

As used herein, the term "polymorph of the present invention" includes polymorphs of the free base of the compound of formula X or a pharmaceutically acceptable salt of the compound of formula X (e.g., hydrochloride, phosphate, maleate, L-malate, adipate, sulphate, fumarate, succinate, L-tartrate, citrate, methanesulfonate, benzoate, and benzenesulfonate), or polymorphs of various solvates of the compound of formula X, and also include different polymorphs of the same salts (such as hydrochloride, phosphate, maleate, L-malate, adipate, sulfate, fumarate, succinate, L-tartrate, citrate, methanesulfonate, benzoate and benzenesulfonate) or solvates.

Preferred polymorphs of the present invention include (but not limited to):

(i) crystal form A, B, C (including C-1, C-2), D, E (crystal form of salt)

(ii) crystal form I, II, III, IV, V (crystal form of the compound of formula X).

In the present invention, some of the crystal forms can be converted into each other, and thus the present invention also provides a method for mutual transformation of part of the crystal forms.

Identification and Properties of Polymorphs

Polymorphs of the compounds of formula X or the pharmaceutically acceptable salts can be characterized using known methods or instruments, for example, using a variety of means and instruments as follows.

X-Ray Powder Diffraction

Methods of determining X-ray powder diffraction of the crystals are known in the art. For example, an X-ray powder diffractometer was used to obtain a pattern with a copper radiation target at a scanning speed of 2° per minute.

The polymorph of the compound of formula X of the present invention or a pharmaceutically acceptable salt thereof has a specific crystalline form and has specific characteristic peaks in an X-ray powder diffraction (XRPD) pattern.

Differential Scanning Calorimetry

It is also called "differential scanning calorimetry analysis" (DSC) which is a technique that measures the relationship between energy difference of the measured substance and the reference substance and temperature during heating. The location, shape and number of peaks on the DSC pattern are related to the nature of the substance, and therefore can be used to qualitatively identify the substance. This method can be commonly used in the art to detect the phase transition temperature, glass transition temperature, reaction heat and other parameters of a substance.

Pharmaceutical Compositions of Compound of Formula X and their Use

Generally, the compound of formula X of the present invention or a pharmaceutically acceptable salt thereof may form a suitable dosage form for administration with one or more pharmaceutically acceptable carriers. These dosage forms are suitable for oral, rectal, topical, intraoral administration, and other parenteral administration (e.g., subcutaneous, intramuscular, intravenous administration, etc.). For example, dosage forms suitable for oral administration include capsules, tablets, granules and syrups. Compounds of the present invention contained in these formulations may be solid powders or granules; aqueous or non-aqueous liquid solutions or suspensions; water-in-oil or oil-in-water emulsions. Such dosage forms may be prepared with active compounds and one or more carriers or excipients through the conventional pharmacy methods. The above-mentioned carriers should be compatible with active compounds or other excipients. For solid formulations, conventional non-toxic carriers include, but not limited to mannitol, lactose, starch, magnesium stearate, cellulose, glucose, sucrose and the like. Carriers used for liquid preparations include water, saline, aqueous dextrose, ethylene glycol and polyethylene glycol. The active compounds may form a solution or suspension with the above-mentioned carriers.

The compositions of the present invention are formulated, quantified and administrated in a manner consistent with the practice of medicine. The "effective amount" of the administrated compound depends on the factors such as the specific disease to be treated, the individual being treated, the cause of diseases, the drug targets and the mode of administration, etc.

The use of the compound of the first aspect of the present invention, or a pharmaceutically acceptable salt, or prodrug thereof for the manufacture of a medicament for adjusting EGFR tyrosine kinase activity or treating EGFR-related diseases is provided.

Preferably, the EGFR-related disease is cancer, diabetes, immune system diseases, neurodegenerative diseases or cardiovascular diseases.

Preferably, the cancer is non-small cell lung cancer, head and neck cancer, breast cancer, renal cancer, pancreatic cancer, cervical cancer, esophageal cancer, pancreatic cancer, prostate cancer, bladder cancer, colorectal cancer, ovarian cancer, stomach cancer, brain malignancies including glioblastoma, etc., or any combination thereof.

Preferably, the non-small cell lung cancer is caused by EGFR mutations, including sensitive mutations (such as L858R mutation or exon 19 deletion) and resistance mutations (such as EGFR T790M mutation).

Preferably, the compound, or a pharmaceutically acceptable salt, or prodrug thereof can also be used to manufacture a medicament for treating a disease with EGFR abnormal expression, or a disease that has acquired resistance during the treatment using EGFR modulators.

Preferably, the acquired resistance is the resistance caused by the T790 mutations encoded by EGFR exon 20, or by comprising the T790 mutations encoded by EGFR exon 20, such as T790M.

In the present invention, the EGFR modulator refers to a small molecule tyrosine kinase inhibitor which targets EGFR, such as gefitinib, erlotinib, Icotinib, lapatinib or afatinib.

A pharmaceutical composition is also provided in the present invention, including a therapeutically effective amount of the compound of the first aspect of the present invention, or a pharmaceutically acceptable salt, or prodrug thereof, as well as one or more other drugs selected from a group consisting of gefitinib, erlotinib, icotinib, lapatinib, XL647, NVP-AEE-788, ARRY-334543, EKB-569, BIBW2992, HKI272, BMS-690514, CI-1033, vandetanib, PF00299804, WZ4002, cetuximab, trastuzumab, panitumumab, matuzumab, nimotuzumab, zalutumumab, pertuzumab, MDX-214, CDX-110, IMC-11F8, Zemab, Her2 vaccine PX 1041, HSP90 inhibitors, CNF2024, tanespimycin, alvespimycin, IPI-504, SNX-5422, NVP-AUY922, or combinations thereof. In addition to the compound of the present invention, or a pharmaceutically acceptable salt, stereoisomer, solvate or prodrug thereof, the other drugs in the pharmaceutical composition described above are the antitumor drugs well known to those skilled in the art.

As used herein, "therapeutically effective amount" refers to the amount that yields a function or activity to humans and/or animals and may be tolerated by humans and/or animals.

The therapeutically effective amount of the compound of the present invention, or a pharmaceutically acceptable salt, stereoisomer, solvate or prodrug thereof contained in the pharmaceutical composition or medicinal composition of the present invention is preferably 0.1 mg-5 g/kg (weight).

The pharmaceutical compositions of the present invention are useful for treating EGFR-related diseases such as cancer, diabetes, immune system disorders, neurodegenerative diseases or cardiovascular diseases, or treating a disease with acquired resistance during the treatment of EGFR modulator.

The disease with the acquired resistance is caused by the T790 mutations encoded by EGFR exon 20, or by comprising the T790 mutations encoded by EGFR exon 20.

In another preferred embodiment, the T790 encoded by EGFR exon 20 is T790M.

For certain diseases, the compounds of the present invention or a pharmaceutically acceptable salt thereof may be used in combination with other drugs in order to achieve the desired therapeutic effect. An example of the combination is for treating advanced NSCLC. For example, a therapeutically effective amount of the compound of formula I of the present invention is used in combination with mTOR inhibitors (e.g., rapamycin); or Met inhibitors (include Met antibody MetMAb and small molecule Met inhibitors PF02341066) MS; or IGF1R inhibitors (e.g., OSI-906); or heat shock protein inhibitors and the like.

The Main Advantages of the Present Invention are:

The polymorph of the compound of formula X or a pharmaceutically acceptable salt thereof has an excellent physical and chemical stability and outstanding related pharmacological activity and is an ideal third generation of EGFR mutant selective inhibitor.

DETAILED DESCRIPTION OF THE EMBODIMENT

The present invention will be further illustrated below with reference to the specific examples. It should be understood that these examples are only to illustrate the invention but not to limit the disclosure of the invention. The experimental methods without specific conditions in the following embodiments are generally carried out according to conventional conditions, or in accordance with the conditions recommended by the manufacturer. Unless indicated otherwise, parts and percentage are calculated by weight.

Reagents and Instruments

The structure and purity of the compounds are identified by nuclear magnetic resonance ($^1$HNMR) and/or LC-MS mass spectrometry (LC-MS) in the present invention. $^1$HNMR: Bruker AVANCE-400 NMR machine, the internal standard was tetramethylsilane (TMS). LC-MS: Agilent 1200 HPLC System/6140 MS liquid-mass spectrometer (available from Agilent), column Waters X-Bridge, 150×4.6 mm, 3.5 μm. Preparative high performance liquid chromatography (pre-HPLC): Waters PHW007, column XBridge C18, 4.6*150 mm, 3.5 um.

ISCO Combiflash-Rf75 or Rf200 automatic eluting column instrument, Agela 4 g, 12 g, 20 g, 40 g, 80 g, 120 g disposable silica gel column.

The known starting materials of the invention may be synthesized by using the methods known in the art, or may be purchased from ABCR GmbH & Co. KG, Acros Organics, Aldrich Chemical Company, Accela ChemBio Inc and Darui Chemical Company etc.

All examples were performed under nitrogen or argon atmosphere and the solution refers to the aqueous solution if without special explanation.

As used herein, DMF refers to dimethylformamide, DMSO refers to dimethylsulfoxide, THF refers to tetrahydrofuran, DIEA refers to N,N-diisopropylethylamine, EA refers to ethyl acetate, PE refers to petroleum ether, BINAP refers to (2R,3S)-2,2'-bis diphenylphosphino-1,1'-binaphthyl, NBS refers to N-bromosuccinimide, NCS refers to N-chlorosuccinimide, $Pd_2(dba)_3$ refers to tris(dibenzylideneacetone)dipalladium, and $Pd(dppf)Cl_2$ refers to [1,1'-bis (diphenylphosphino) ferrocene] palladium dichloride.

As used herein, room temperature refers to be about 25° C.

General Method

The powder X-ray diffraction patterns are obtained using a PANalytical Empyrean X-ray powder diffraction analyzer through methods known in the art. Instrument test conditions are shown in Table i below:

TABLE i

| Parameter | XRPD (reflection mode) |
| --- | --- |
| X-ray | Cu, kα, Kα1(Å): 1.540598; Kα2 (Å): 1.544426 Kα2/Kα1 Intensity ratio: 0.50 |
| X-ray tube settings | 45 kV, 40 mA |
| Divergence slit | automatic |
| Monochromator | no |
| Scanning mode | continuous |
| Scanning range (°2θ(°)) | 3°-40° |
| Scanning step (°2θ(°)) | 0.013 |
| Scan time (minutes) | ~7 |

In the powder X-ray diffraction pattern, the site of each peak was determined by 2θ(°). It should be understood that different instruments and/or conditions could result in slightly different data and changes in peak site and relative intensity. The division of the intensity of peaks only reflects the approximate size of peaks in each site. In the present invention, the highest diffraction peak of each crystalline form was taken as the base peak which was defined as $I_0$ with the relative intensity as 100%. (for example, the peak at 2θ(°) value of 21.38 as the base peak of crystal form I, the peak at 2θ(°) value of 9.47 as the base peak of crystal form II, the peak at 2θ(°) value of 23.89 as the base peak of crystal form III, the peak at 2θ(°) value of 7.69 as the base peak of crystal form IV, the peak at 2θ(°) value of 8.89 as the base peak of crystal form V, the peak at 2θ(°) value of 23.31 as the base peak of crystal form A, the peak at 2θ(°) value of 19.92 as the base peak of crystal form B, the peak at 2θ(°) value of 25.55 as the base peak of crystal form C-1, the peak at 2θ(°) value of 7.48 as the base peak of crystal form C-2, the peak at 2θ(°) value of 22.69 as the base peak of crystal form D, the peak at 2θ(°) value of 21.64 as the base peak of crystal form E), and other peaks had the ratio of their peak height to the peak height of base peak as the relative intensity $I/I_0$. The definition of the relative intensity of each peak was shown in the following table ii:

TABLE ii

| Relative intensity I/I$_0$(%) | Definition |
|---|---|
| 50-100 | VS (very strong) |
| 20-50 | S (strong) |
| 5-20 | M (medium) |
| 1-5 | W (weak) |

The acid-base molar ratio of the salts of the present invention or their crystalline forms was determined by HPLC/IC or $^1$H NMR.

High Performance Liquid Chromatography (HPLC) spectrum was acquired on an Agilent 1100/1260 HPLC.

TGA and DSC pattern: TGA and DSC pattern were acquired on a TA Q500/5000 thermogravimetric analyzer and a TA Q200/2000 differential scanning calorimeter respectively. The instrument test conditions are shown in the following table iii:

TABLE iii

| Parameter | TGA | DSC |
|---|---|---|
| Method | Linear warming | Linear warming |
| Sample tray | Platinum plate, open | Aluminum plate, gland |
| Temperature range | Room temperature-set temperature | 25° C.-set the temperature |
| Scanning rate (° C./min) | 10 | 10 |
| Protective gas | Nitrogen | Nitrogen |

Dynamic Vapor Sorption (DVS) curve: collected on DVS Intrinsic SMS (Surface Measurement Systems). The relative humidity at 25° C. is corrected with the deliquescent points of LiCl, Mg (NO$_3$)$_2$ and KCl. Instrument test conditions are shown in Table iv below:

TABLE iv

| Parameters | Setting value |
|---|---|
| Temperature | 25° C. |
| Sample size | 10-20 mg |
| Protect gas and flow | N$_2$, 200 ml/min |
| dm/dt | 0.002%/min |
| Minimum dm/dt balance time | 10 minutes |
| The maximum balance time | 180 minutes |
| RH range | 0% RH-90% RH-0% RH |
| RH gradient | 10%(0% RH-90% RH, 90% RH-0% RH) 5%(90% RH-95% RH, 95% RH-90% RH) |

Moisture content: the test was performed on a Wantong 870 Karl Fischer moisture meter, the titrant solution used was Hydranal® R-Composite5 (34805-1L-R, Batch # SZBD3330V) from Sigma-Aldrich, and analytical pure MeOH was used as solvent. Correction with high purity water was performed before moisture measurement.

It should be understood that different values may be obtained when other types of instruments with the same function as the instruments described above or test conditions which are different from the conditions used in the present invention were used. Therefore, the recited value should not be considered as an absolute numerical value.

Due to the instrumental errors or different operators, one skilled in the art will understand that the above parameters used to characterize the physical properties of crystals may differ slightly, so the parameters described above are only used to assist in characterizing the polymorphs provided herein, and can not be regarded as a limitation on the polymorphs of the present invention.

Preparation of Intermediate

Preparation of Compound 1a

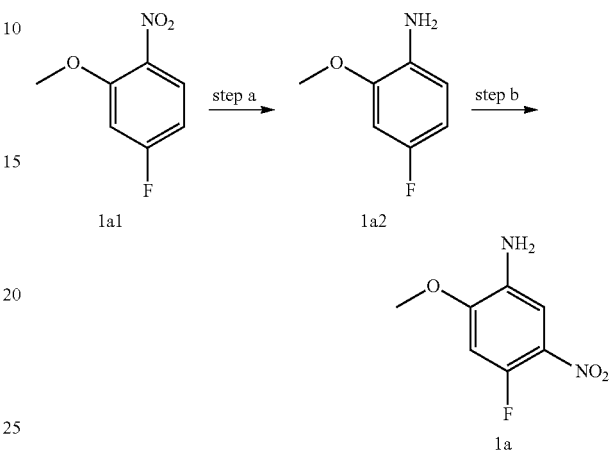

Step a: Compound 1a1 (10.6 g, 58 mmol) was added into a 500 ml reaction flask, and THF/water (100 ml/60 ml) mixed solution was added to dissolve the compound. Ammonium chloride (15.5 g, 292 mmol) and reduced iron powder (26 g, 467 mmol) were sequentially added with stirring at room temperature, and then the reaction system was heated to 65° C. and stirred continually for 3 h. The reaction progress was monitored by TLC. After completion of the reaction, the excess iron powder was removed by filtration, and the filter cake was washed for three times with EA. Filtrate was extracted with EA/water system for three times, and the organic layer was separated, washed with water, saturated brine, dried over anhydrous Na$_2$SO$_4$, and concentrated under reduced pressure to give compound 1a2 (8.0 g) which was used directly in the next reaction. Yield: 93%; purity: 90%; MS m/z (ESI):142.0 [M+H]+.

Step b: Compound 1a2 (8.0 g, 43 mmol) was added into a 500 ml reaction flask, and concentrated sulfuric acid (100 ml) was added to dissolve the substrate under constant agitation. At −20° C., concentrated nitric acid (6.15 ml, 48 mmol) was slowly added dropwise with stirring, and the reaction mixture was stirred for 5 mins at this temperature. The reaction progress was monitored by TLC. After completion of the reaction, the mixture was poured into ice water. Sodium hydroxide/water solution (150 ml/300 ml) were added slowly to the reaction system at −20° C. in an ice-water bath, and the mixture was adjusted to pH 8-9. The reaction solution was extracted with EA/water system for three times, the organic layer was separated, washed with water, saturated brine, dried over anhydrous Na$_2$SO$_4$, and concentrated under reduced pressure to give compound 1a (8.7 g) which was used directly in the next reaction. Yield: 80%; purity: 100%; MS m/z (ESI): 187.0 [M+H]+; 1H NMR (400 MHz, DMSO-d6): δ 7.34 (d, J=7.8 Hz, 1H), 7.04 (d, J=13.4 Hz, 1H), 5.25 (brs, 2H), 3.90 (s, 3H).

Preparation of Intermediate 2a

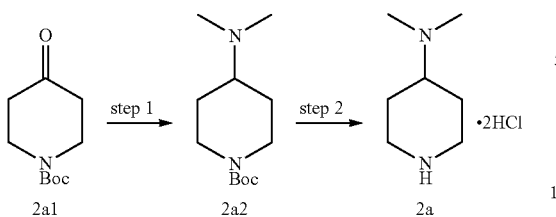

Step 1: Compound 2a1 (500 g, 2.51 mol) and dimethylamine hydrochloride (244 g, 3.01 mol) were added to methanol (2.2 L), triethylamine (508 g, 5.03 mol) and 10% Palladium on carbon (50 g) were added. The mixture was then reacted in hydrogen (15 kg, 40° C.) for 24 hours. The reaction was complete by LCMS, filtrated, the filtrate was evaporated to dryness under reduced pressure to give the oily crude compound 2a2 (542 g) which can be used directly in the next step without purification. MS m/z (ESI): 228 [M−H].

Step 2: Compound 2a2 (542 g, 2.38 mol) was dissolved in methanol (1.5 L), concentrated hydrochloric acid (1 L) was added slowly and in portions and the mixture was stirred at 50° C. for 2 hours, and evaporated to dryness under reduced pressure to give a crude solid. The crude solid was slurried in methanol (2 L) for 1 h and filtered to give 2a as a white solid (389 g, 80%). $^1$H NMR (400 MHz, DMSO) delta 3.47 (m, 3H), 2.97 (m, 2H), 2.70 (s, 6H), 2.22 (m, 2H), 1.87 (m, 2H).

Preparation of Intermediate 3a

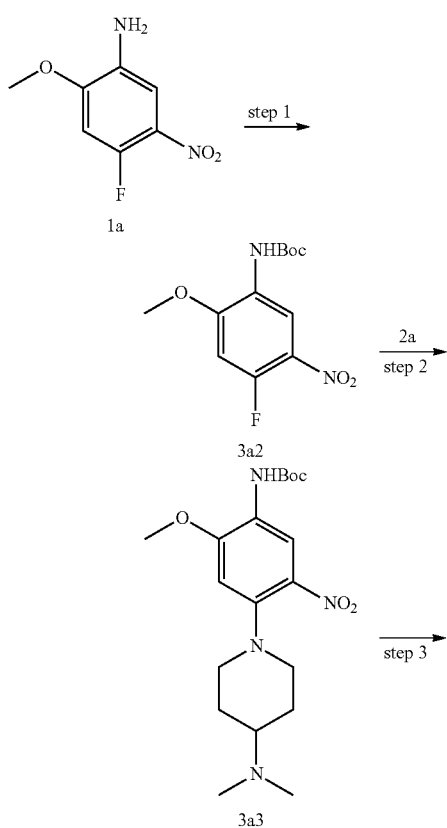

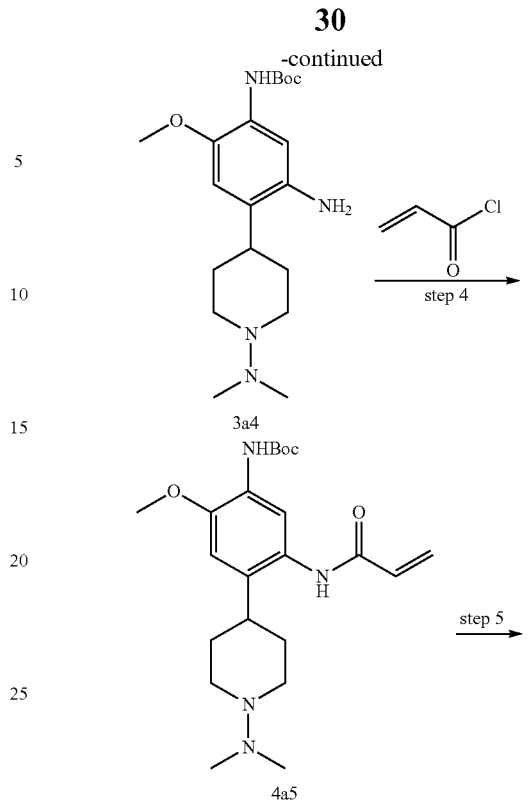

Step 1: Compound 1a (11.16 g, 60 mmol) was dissolved in 150 ml of dichloromethane, ditertbutyl dicarbonate (15.60 g, 72 mmol), triethylamine (12.24 g, 120 mmol) and 4-dimethylaminopyridine (0.74 g of, 6 mmol) were added and stirred at room temperature for 18 h. The reaction progress was monitored by TLC. After completion of the reaction, the reaction solution was concentrated under reduced pressure, isolated and purified by column chromatography [PE:EA=80:20] to give the title compound 3a2 (12.56 g, 73%). MS m/z (ESI): 285 [M−H]+.

Step 2: Compound 3a2 (11.46 g, 40 mmol) was dissolved in 60 ml N,N-dimethylacetamide, and compound 2a (9.6 g, 48 mmol), N,N-diisopropylethylamine (7.74 g, 60 mmol) were added and heated to 90° C. and stirred for 6 h. The reaction progress was monitored by TLC. After completion of the reaction, the reaction solution was cooled to room temperature, poured into ice water, extracted with ethyl acetate, washed with water and saturated brine, dried over anhydrous Na$_2$SO$_4$, and concentrated under reduced pressure to give the title product compound 3a3 (13.43 g, 85%). It was used directly in the next reaction. MS m/z (ESI): 395 [M+H]+.

Step 3: Compound 3a3 (12.8 g, 32.6 mmol) was dissolved in 200 ml of methanol, and 1.0 g 10% Pd/C was added. After the replacement of air with hydrogen, the reaction solution was stirred for 1 h under hydrogen filled in the balloon at room temperature. The reaction progress was monitored by TLC. After completion of the reaction, the reaction system was filtered by buchuer funnel, the filter cake was washed with small amount of methanol, and the filtrate was concentrated to give the title product compound 3a4 (11.54 g, 97%). It was used directly in the next reaction. MS m/z (ESI): 365 [M+H]+.

Step 4: Compound 3a4 (10.95 g, 30 mmol) and triethylamine (6.12 g, 60 mmol) were dissolved in 200 ml of dichloromethane, and cooled to 0° C. Acryloyl chloride (3.24 g, 36 mmol) was added and stirred under nitrogen at room temperature for 3 h. The reaction progress was monitored by TLC. After completion of the reaction, the reaction solution was washed successively with saturated aqueous sodium bicarbonate solution and saturated brine, dried over anhydrous $Na_2SO_4$, filtered, and concentrated under reduced pressure to give the title product compound 3a5 (10.3 g, 82%). It was used directly in the next reaction. MS m/z (ESI):419 [M+H]+.

Step 5: Compound 3a5 (10 g, 24 mmol) was dissolved in 100 ml of dichloromethane, cooled to 0° C., 20 ml of trifluoroacetic acid was added, and the reaction was stirred under nitrogen at room temperature for 18 h. The reaction progress was monitored by TLC. After completion of the reaction, the reaction solution was concentrated under reduced pressure. The residue was dissolved in 300 ml of dichloromethane, washed with saturated aqueous sodium bicarbonate solution, and saturated brine successively, dried over anhydrous $Na_2SO_4$, filtered, and concentrated under reduced pressure to give the crude product, which was purified by column chromatography [DCM:MeOH=10:1] to give the title product Compound 3a (3.54 g, 46.5%). MS m/z (ESI): 319 [M+H]+.

Example 1 Preparation of the Compound of Formula X

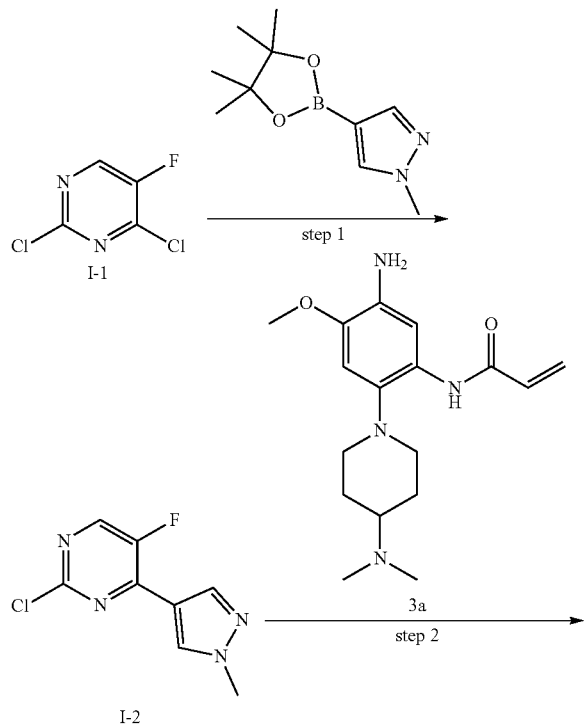

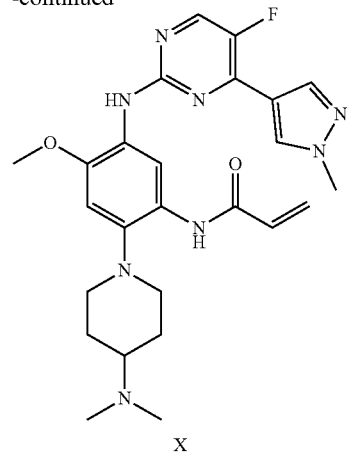

X step 1: The mixed solution of 1-methyl-4-(4,4,5,5-tetramethyl-1,3,2-dioxaborolan-2-yl)-1H-pyrazole (1.1 g, 5.25 mmol), compound I-1 (664 mg, 4 mmol), Pd(dppf)Cl$_2$ (109.7 mg, 0.15 mmol) and sodium carbonate solution (5 ml, 2M) in acetonitrile (30 mL) was stirred under nitrogen atmosphere at 85° C. for 6 h. After completion of the reaction, the reaction was quenched with water, EA (150 ml) was added to the reaction mixture, the layers separated, the aqueous phase was extracted with EA (50 ml×2) twice, and the combined organic phase was dried over $Na_2SO_4$ and concentrated to give the crude product which was purified by Combi-flash column chromatography [PE:EA=5:1-2:1] to give 0.73 g title compound I-2. MS m/z (ESI): 213[M+H]+.

Step 2: Cesium carbonate (487.5 mg, 0.5 mmol) was added to a solution of compound 3a (159 mg, 0.5 mmol), compound I-2 (106 mg, 0.5 mmol), Pd$_2$(dba)$_3$ (45.75 mg, 0.05 mmol) and Xantphos (28.4 mg, 0.05 mmol) in 1,4-dioxane (4 ml), the reaction mixture was stirred at 100° C. for 3 h, EA (50 ml×2) and water (10 ml) were added to the reaction mixture, the organic phase was washed with water (10 ml×3), dried over $Na_2SO_4$, and concentrated to give the crude product, and the resulting crude product was separated and purified by preparative liquid chromatography to give the title compound X (22 mg, 9%), MS m/z (ESI):495.0[M+H]$^+$; $^1$HNMR (400 MHz, DMSO-d$_6$) δ 9.05 (1s, 1H), 9.01 (1s, 1H), 8.80 (s, 1H), 8.48 (d, J=4 Hz, 1H), 8.18 (s, 1H), 7.89 (s, 1H), 6.87 (s, 1H), 6.73 (m, 1H), 6.32 (m, 1H), 5.78 (t, 1H), 3.97 (s, 3H), 3.88 (s, 3H), 3.01 (d, J=12 Hz, 2H), 2.66 (t, 2H), 2.19 (s, 6H), 2.16 (m, 1H), 1.84 (m, 2H), 1.71 (m, 2H).

Comparative Example

By using the corresponding boron ester and unsubstituted or 5-methoxy substituted 2,4-dichloropyrimidine as the starting materials, comparative compounds 2 and 3 were prepared with reference to the similar method of compound of formula X, as shown in Table v.

TABLE V

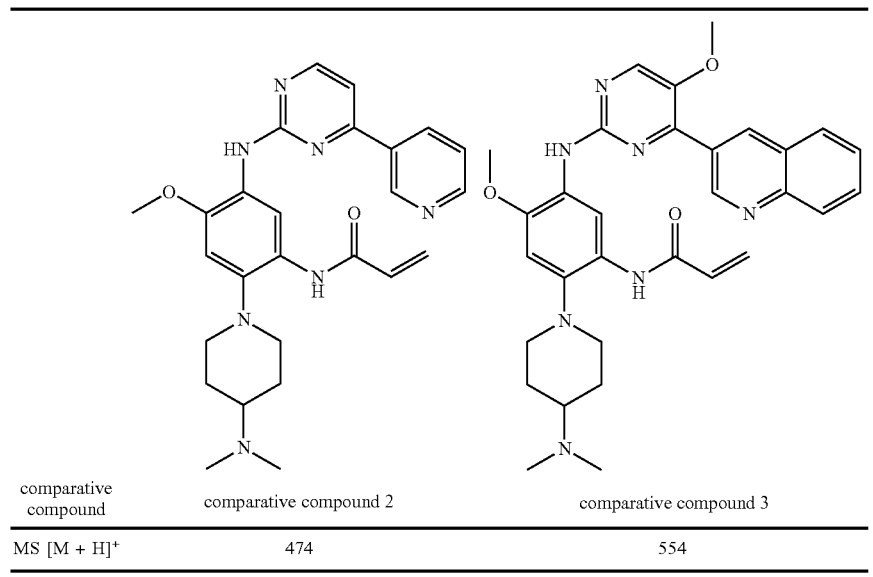

| comparative compound | comparative compound 2 | comparative compound 3 |
|---|---|---|
| MS [M + H]+ | 474 | 554 |

Example 2 Preparation of the Free Base of Compound of Formula X as the Starting Compound 55.8 g of the compound of formula X was added into 230 ml of ethanol, refluxed and stirred, 160 ml of water was added under reflux, the reaction solution became cloudy, then 10 ml of ethanol was added to make the reaction solution clear and heating was stopped. The reaction solution was slowly cooled to room temperature, a large amount of yellow solid was precipitated from the solution, filtered, washed with water and dried under vacuum to give 52.8 g of yellow powder, yield 94.7%.

Example 3 Preparation of Crystal Form a of the Compound of Formula X

Figure 2A:
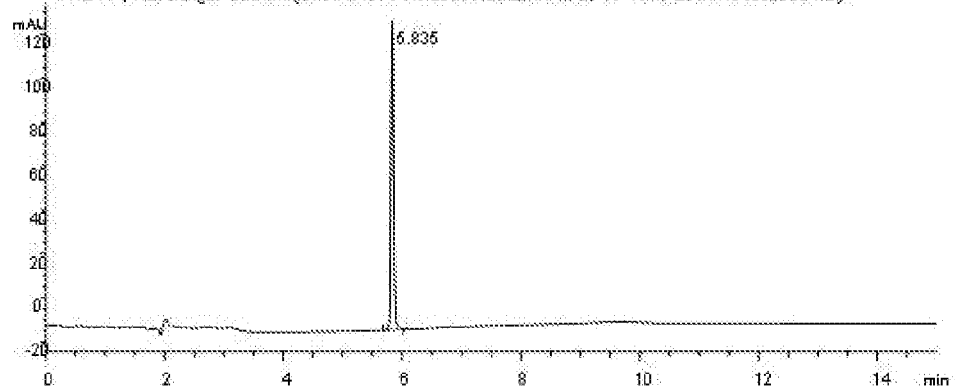
FIG. 2 shows the HPLC spectrum (FIG. 2A), the IC spectrum (FIG. 2B) and the TGA/DSC pattern (FIG. 2C) of crystal form A.
Figure 2B:
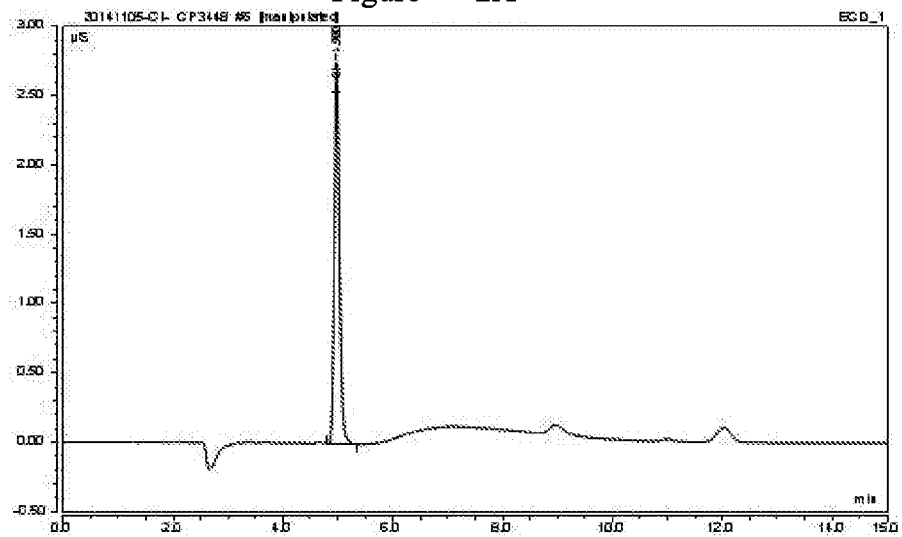
Figure 2C:
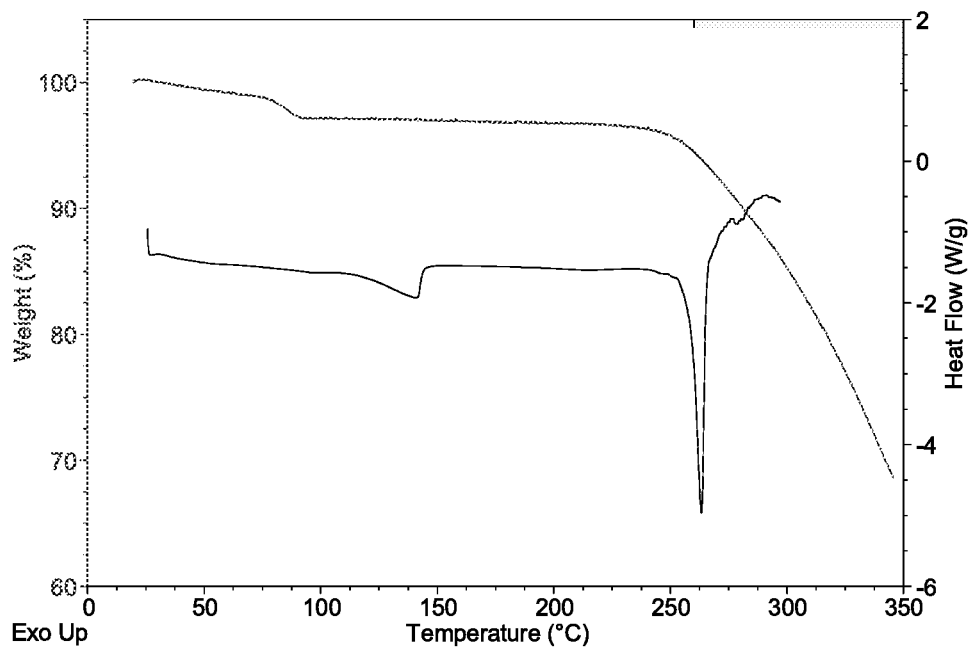

A solution of hydrochloric acid in acetonitrile (0.2 mol/L, 3.3 mL) and acetonitrile (2.0 mL) were added to a reaction flask containing 300 mg of the free base of compound of formula X as the starting sample to form a turbid solution which was magnetically stirred for about 43 hours at 15° C. at a speed of about 1000 r/min. The solid was separated by vacuum suction filtration. After vacuum drying at 50° C. for about 4 hours, 245 mg of a yellow crystalline powder was collected, yield: 81.7%. The powder X-ray diffraction pattern of the resulting crystal is shown in FIG. 1 (2° angles are indicated). The HPLC and IC spectra of the crystal are shown in FIGS. 2A and 2B respectively. The molar ratio of acid to base is 0.9:1. The TGA/DSC spectra was characterized in FIG. 2C; mp 261-265° C. The crystal form is defined as crystal form A in the present application.

Example 4 Preparation of Crystal Form B of the Compound of Formula X

Figure 3:
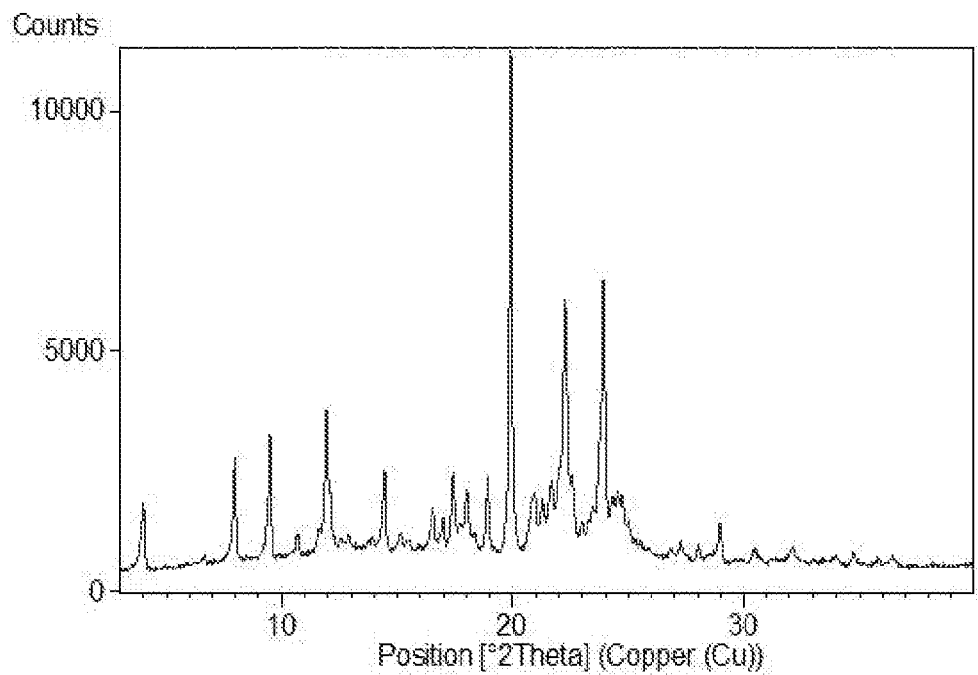
FIG. 3 shows the XRPD pattern of crystal form B.
Figure 4:
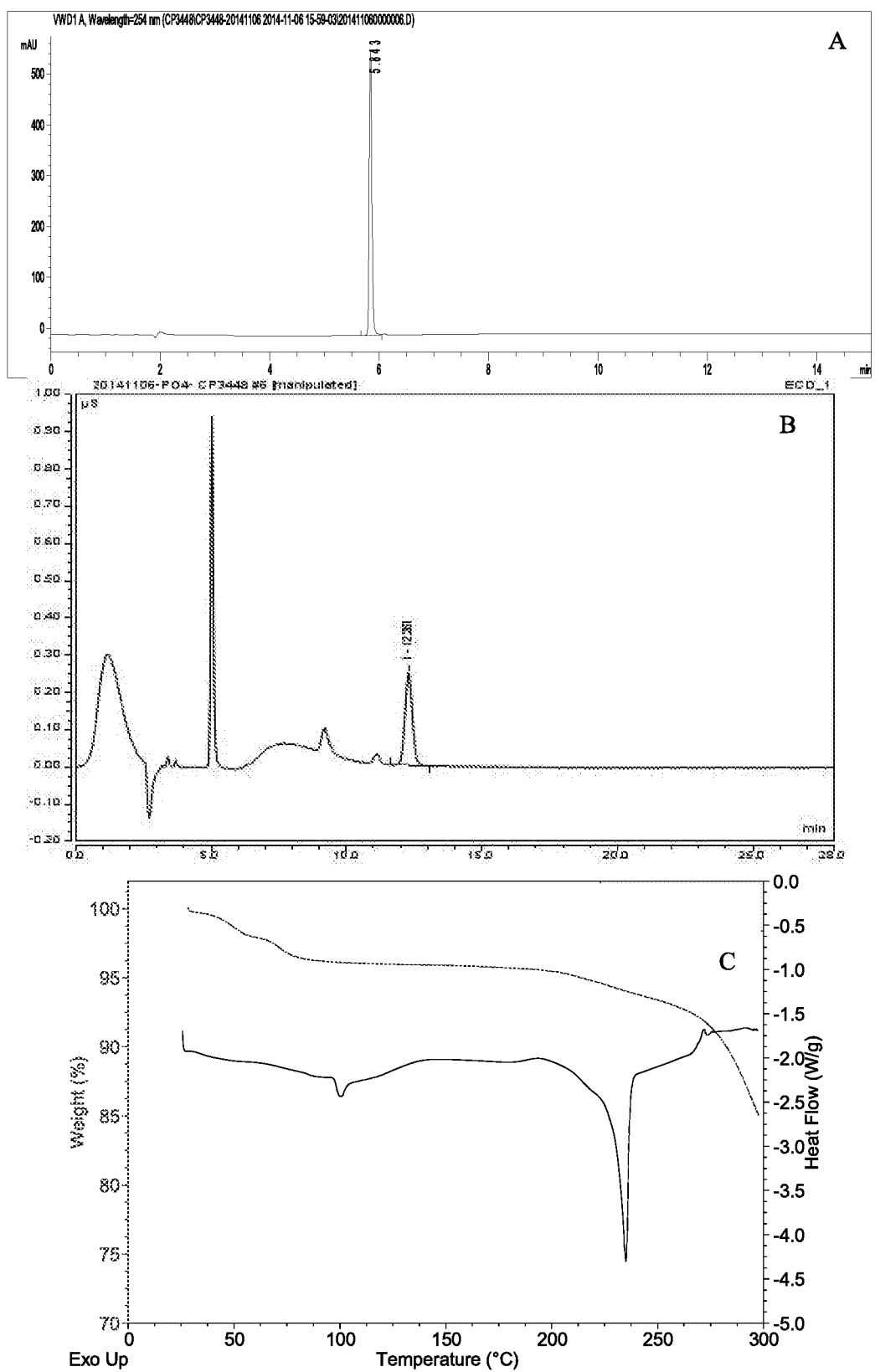
FIG. 4 shows the HPLC spectrum (FIG. 4A), the IC spectrum (FIG. 4B) and the TGA/DSC pattern (FIG. 4C) of crystal form B.

A solution of phosphoric acid in acetonitrile (0.2 mol/L, 3.3 mL) and acetonitrile (1.0 mL) were added to a reaction flask containing 300 mg of the free base of compound of formula X as the starting sample to form a turbid solution which was magnetically stirred for about 43 hours at 15° C. at a speed of about 1000 rev/min. The solid was isolated by vacuum suction filtration. After vacuum drying at 50° C. for about 4 hours, 280 mg of a yellow crystalline powder was collected, yield: 93.4%. The powder X-ray diffraction pattern of the resulting crystal is shown in FIG. 3. The HPLC and IC spectra of the crystal are shown in FIGS. 4A and 4B respectively. The molar ratio of acid to base is 0.9:1. The TGA/DSC spectra was characterized in FIG. 4C; mp 231° C.-237° C. The crystal form is defined as crystal form B in the present application.

Figure 5:
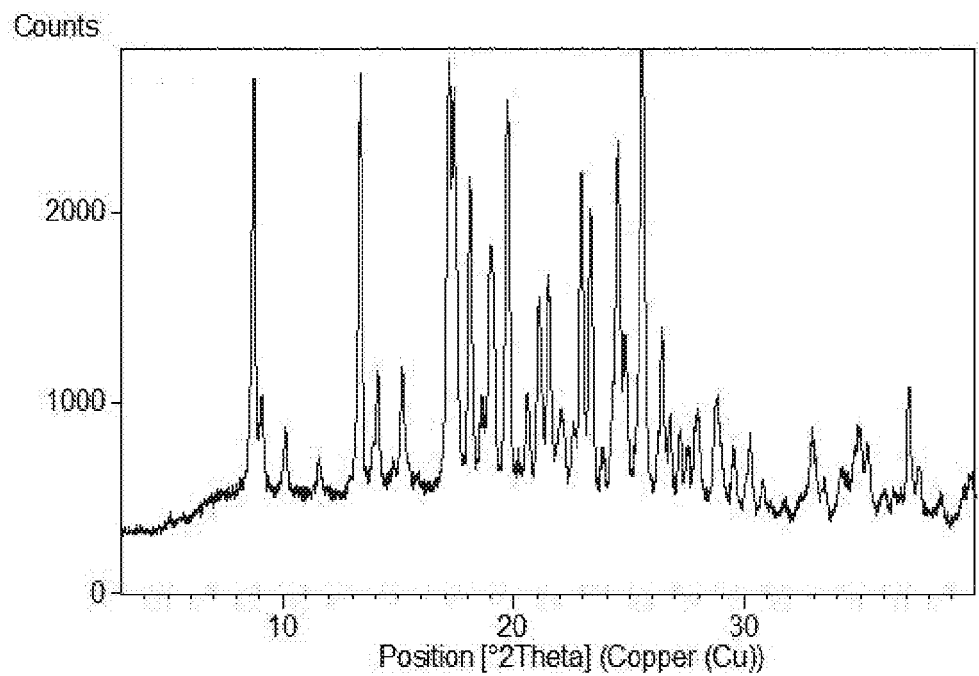
FIG. 5 shows the XRPD pattern of crystal form C-1.
Figure 6A:
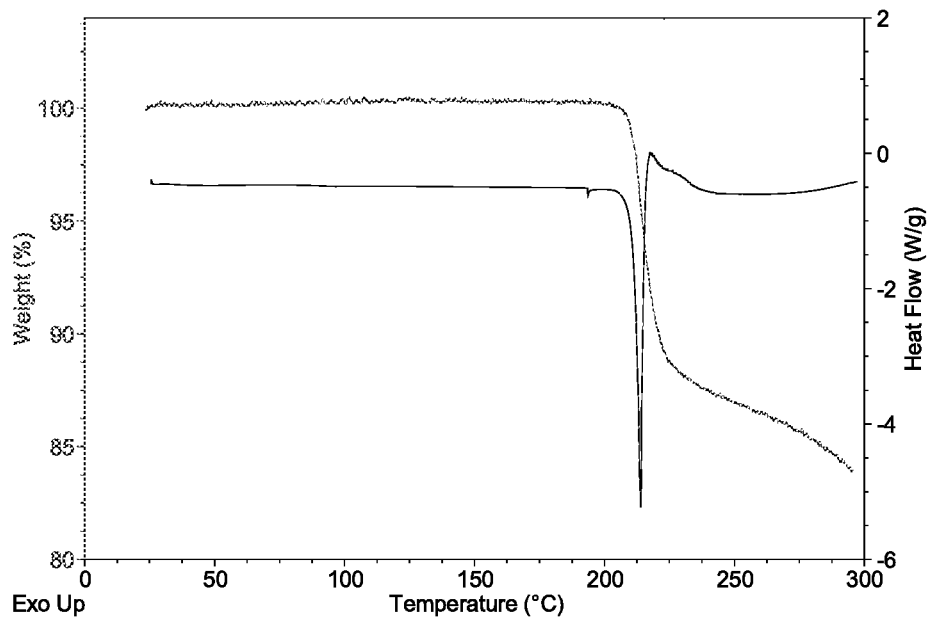
FIG. 6 shows the TGA/DSC pattern (FIG. 6A), and the $^1$HNMR spectrum (FIG. 6B) of crystal form C-1.
Figure 6B:
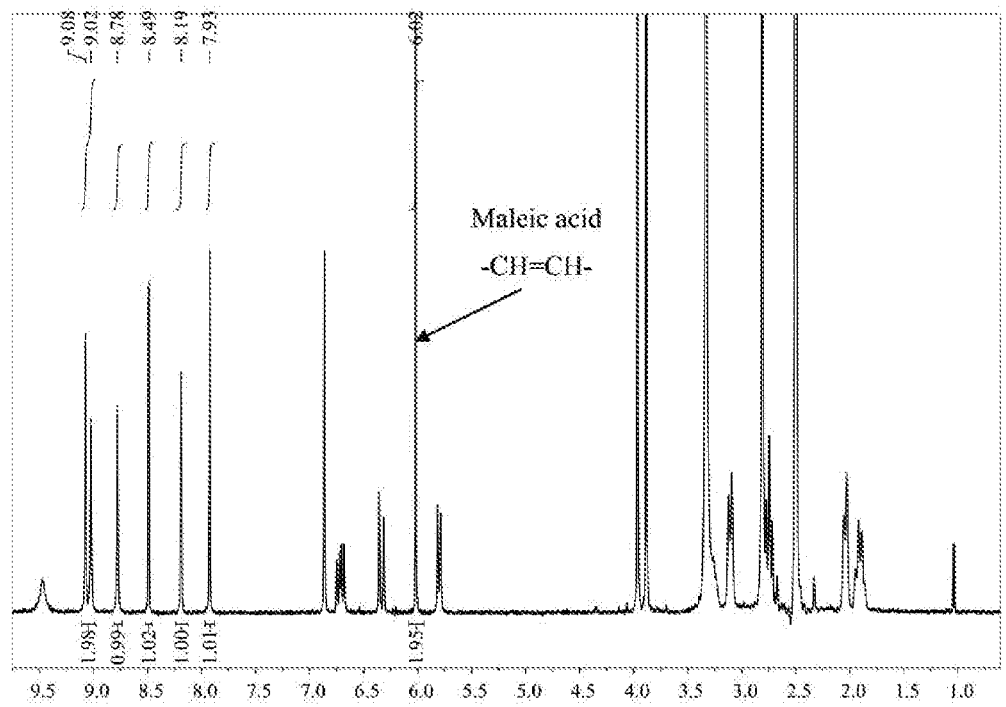

Example 5 Preparation of Crystal Form C-1 of the Compound of Formula X 70.2 mg of maleic acid and acetonitrile (10.0 mL) were added to a reaction flask containing 300 mg of the free base of compound of formula X as the starting sample to form a turbid solution which was magnetically stirred for about 28 hours at 15° C. at a speed of about 1000 rev/min. The solid was isolated by vacuum suction filtration. After vacuum drying at 50° C. for about 24 hours, 286.2 mg of a yellow crystalline powder was collected, yield: 95.4%. The powder X-ray diffraction pattern of the resulting crystal is shown in FIG. 5. The TGA/DSC spectra was characterized in FIG. 6A; The $^1$H NMR spectrum is shown in FIG. 6B. The molar ratio of acid to base is 1:1. mp 212° C.-216° C. The crystal form is defined as crystal form C-1 in the present application.

Example 6 Preparation of Crystal Form C-1 of the Compound of Formula X

The free base of compound of formula X as the starting sample (5.50 g, 11.1 mmol) was dissolved in ethanol (16.5 mL), warmed to 70° C. and maleic acid (1.55 g, 13.3 mmol) was added with stirring, and the temperature of the reaction was controlled at 70° C., the mixture was stirred for 30 min, a large amount of solid was precipitated, heating was stopped, the mixture was naturally cooled to 5° C. with stirring for 2 hours, and stirred for 1 h after cooling, filtered, the filter cake was rinsed with ethanol, dried under blast at 50° C. for 2 h, dried under blast at 80° C. for 6 h to obtain the crystalline yellow powder 6.05 g, yield of 89.1%. The powder X-ray diffraction pattern of the resulting crystal is shown in FIG. 5. The TGA/DSC spectrum was characterized in FIG. 6A; The $^1$H NMR spectrum is shown in FIG. 6B. The molar ratio of acid to base is 1:1. mp 212° C.-216° C. The crystal form is defined as crystal form C-1 in the present application.

Figure 7:
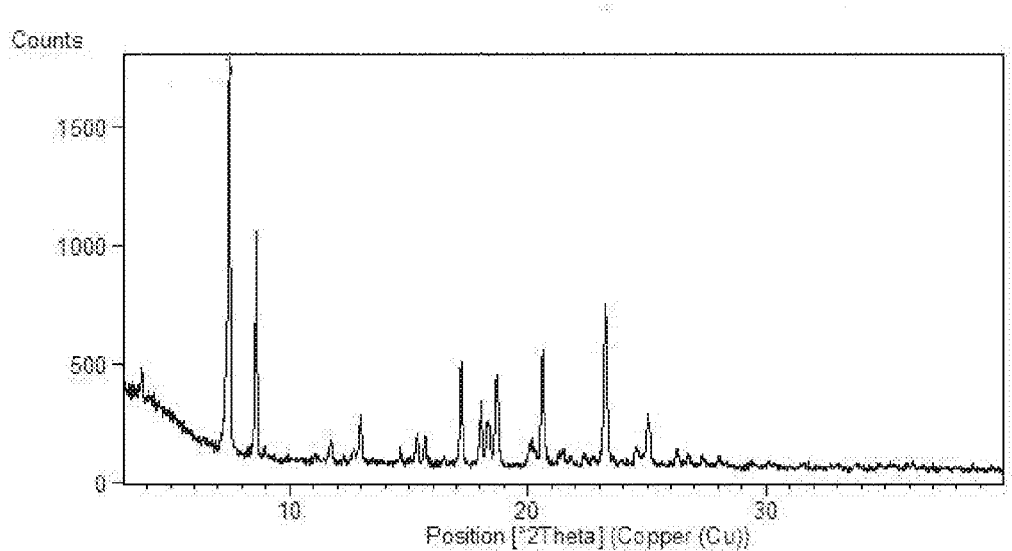
FIG. 7 shows the XRPD pattern of crystal form C-2.
Figure 8:
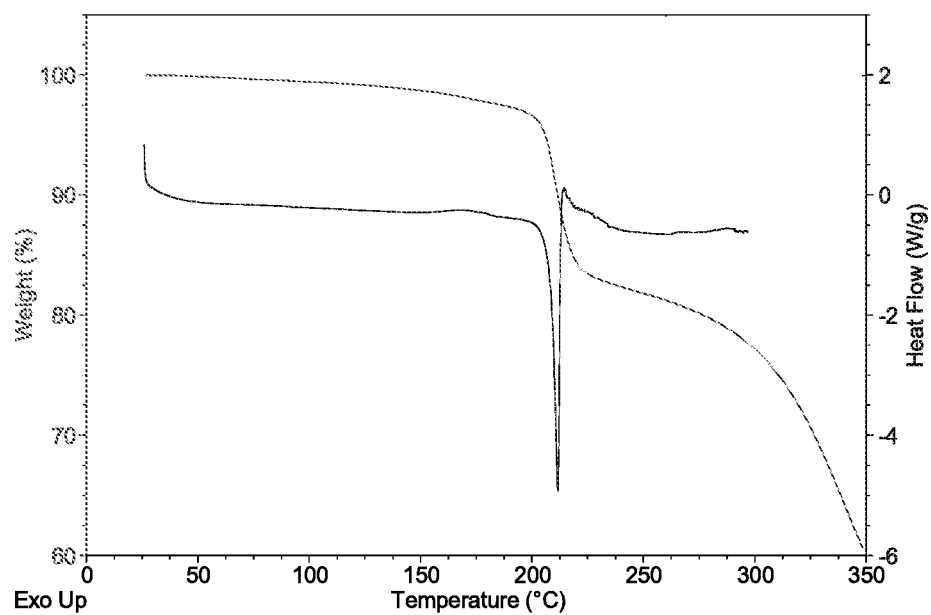
FIG. 8 shows the TGA/DSC pattern of crystal form C-2.

Example 7 Preparation of Crystal Form C-2 of the Compound of Formula X 1.5 ml of DCM was added to a reaction flask containing 10.1 mg of crystal form C-1, after dissolved, the flask was sealed with a sealing film at 15° C. After punctured 3-4 small holes with a needle, the flask was placed in a fume cupboard for slow natural volatilization, after 10 days, the sample was dried to give a yellow crystalline powder 9 mg, yield 89.1%. The powder X-ray diffraction pattern of the resulting crystal is shown in FIG. 7, the molar ratio of acid to base is 1:1, and the TGA/DSC pattern is characterized in FIG. 8; mp 210-214° C. The crystal form is defined as crystal form C-2 in the present application.

Figure 9:
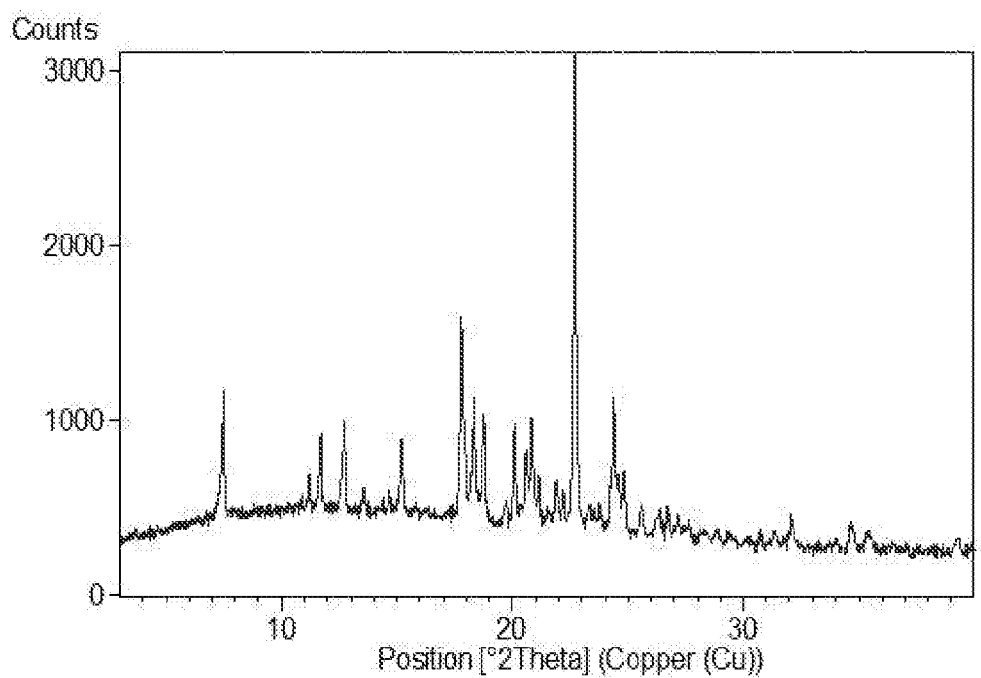
FIG. 9 shows the XRPD pattern of crystal form D.
Figure 10:
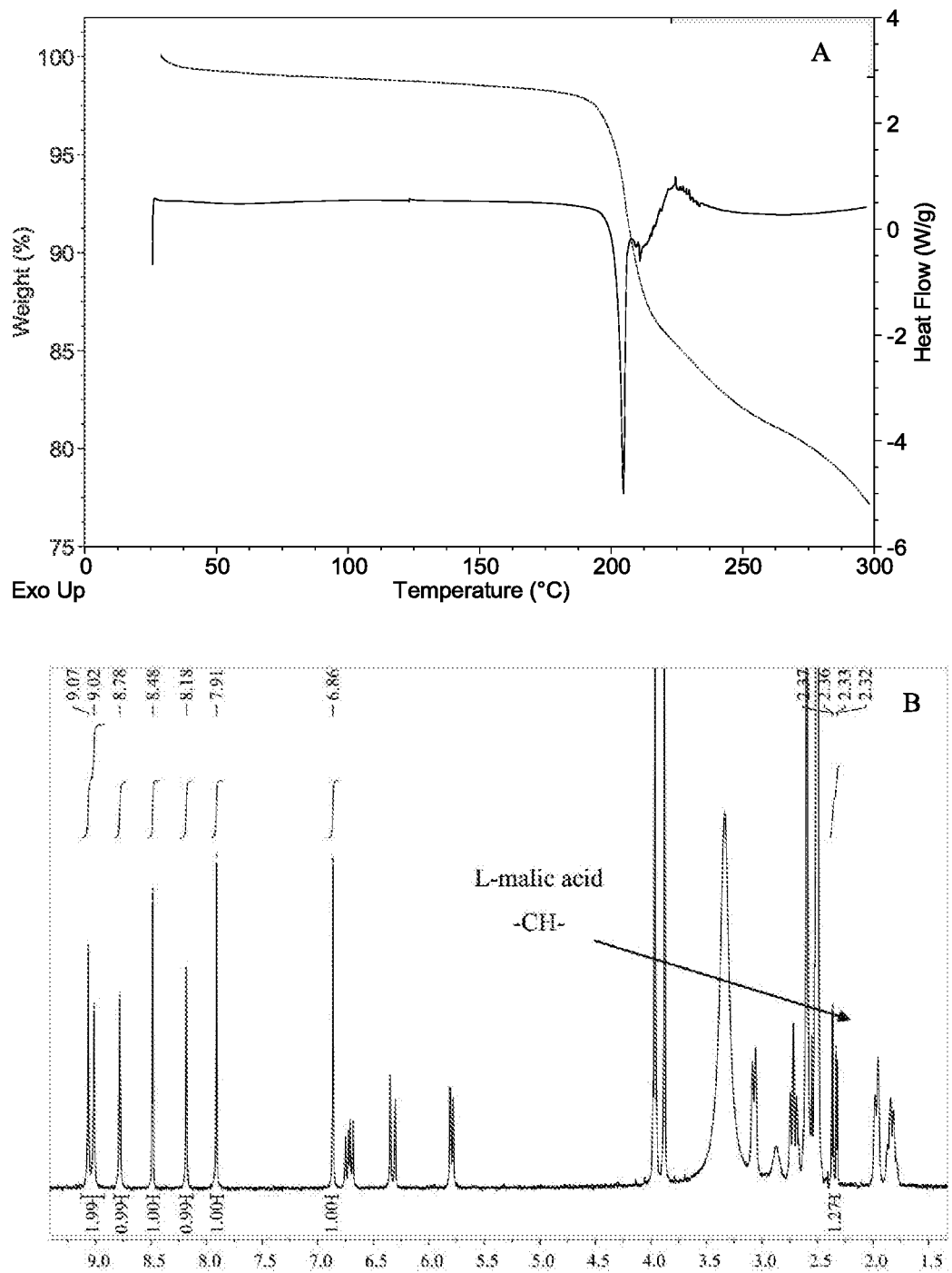
FIG. 10 shows the TGA/DSC pattern (FIG. 10A) and the $^1$HNMR spectrum (FIG. 10B) of crystal form D.

Example 8 Preparation of Crystal Form D of the Compound of Formula X 81.3 mg of L-malic acid and acetonitrile (8.0 mL) were added to a reaction flask containing 300 mg of the free base of compound of formula X as the starting sample to form a turbid solution which was magnetically stirred for about 28 hours at 15° C. at a speed of about 1000 r/min. The solid was isolated by vacuum suction filtration. After vacuum drying at 50° C. for about 24 hours, 253 mg of a yellow crystalline powder was collected, yield: 84.4%. The powder X-ray diffraction pattern of the resulting crystal is shown in FIG. 9. The $^1$H NMR spectrum is shown in FIG. 10B, The molar ratio of acid to base is 1.3:1, The TGA/DSC spectra was characterized in FIG. 10A; mp 202° C.-207° C. The crystal form is defined as crystal form D in the present application.

Figure 11:
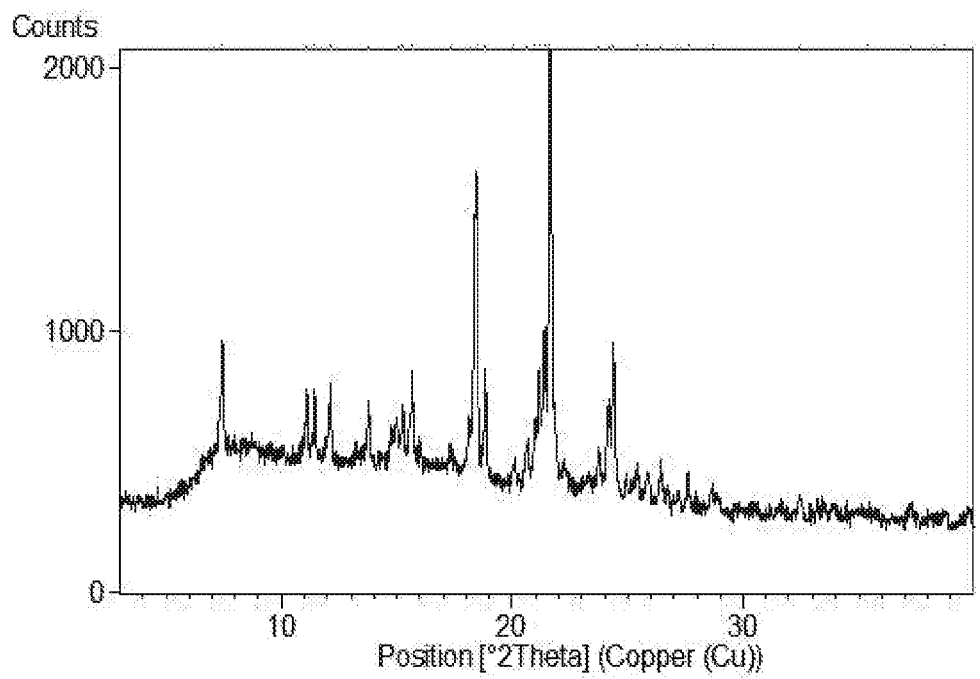
FIG. 11 shows the XRPD pattern of crystal form E.
Figure 12A:
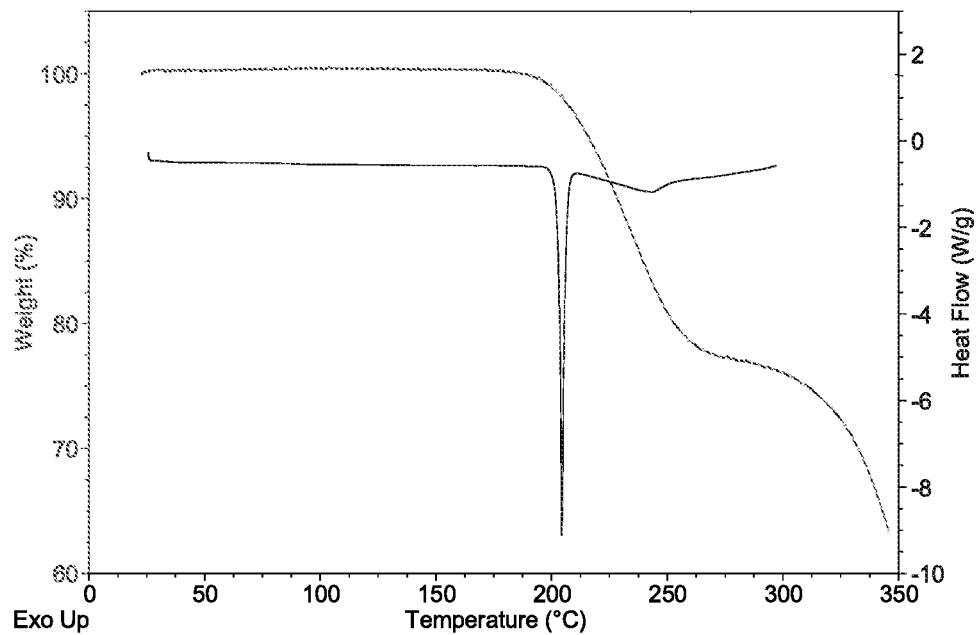
FIG. 12 shows the TGA/DSC pattern (FIG. 12A) and the $^1$HNMR spectrum (FIG. 12B) of crystal form E.
Figure 12:
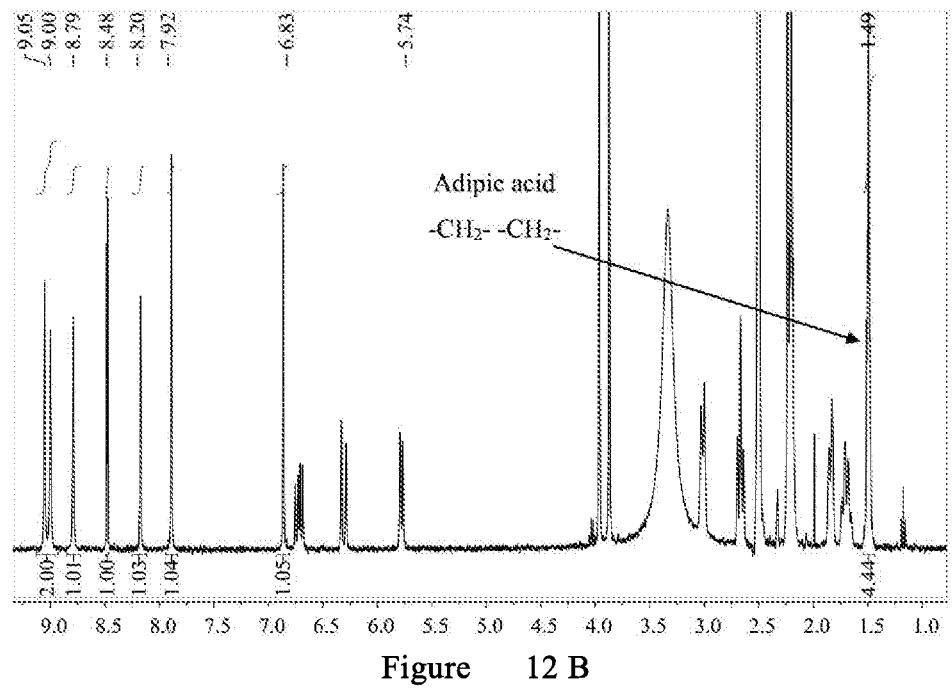

Example 9 Preparation of Crystal Form E of the Compound of Formula X 88.5 mg of adipic acid and acetonitrile (8.0 mL) were added to a reaction flask containing 300 mg of the free base of compound of formula X as the starting sample to form a turbid solution which was magnetically stirred for about 28 hours at 15° C. at a speed of about 1000 r/min. The solid was isolated by vacuum suction filtration. After vacuum drying at 50° C. for about 24 hours, 278 mg of a yellow crystalline powder was collected, yield: 92.8%. The powder X-ray diffraction pattern of the resulting crystal is shown in FIG. 11. The $^1$H NMR spectrum is shown in FIG. 12B, The molar ratio of acid to base is 1:1, The TGA/DSC spectra was characterized in FIG. 12A; mp 204° C.-206° C. The crystal form is defined as crystal form E in the present application.

Figure 13:
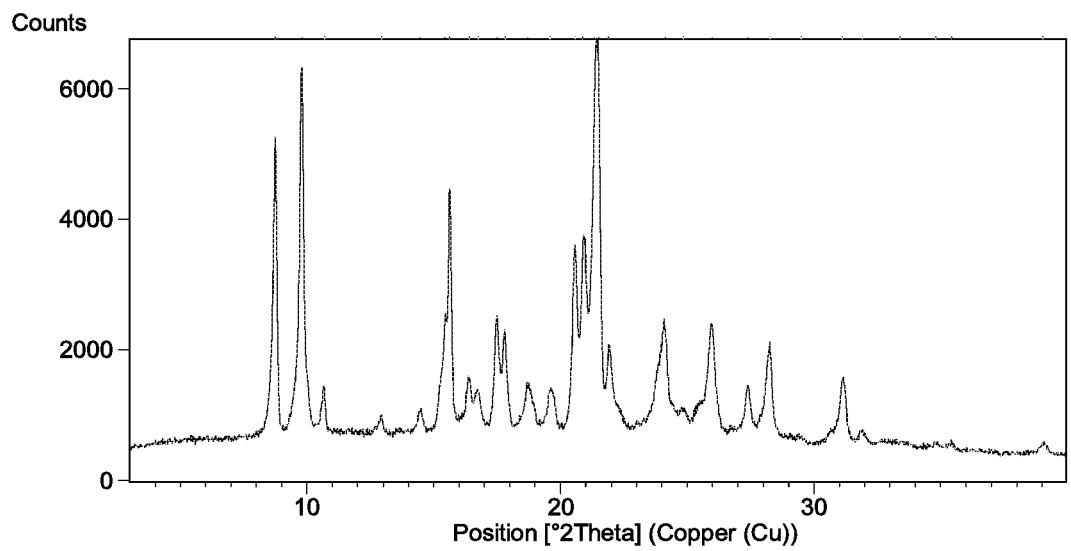
FIG. 13 shows the XRPD pattern of crystal form I.
Figure 14:
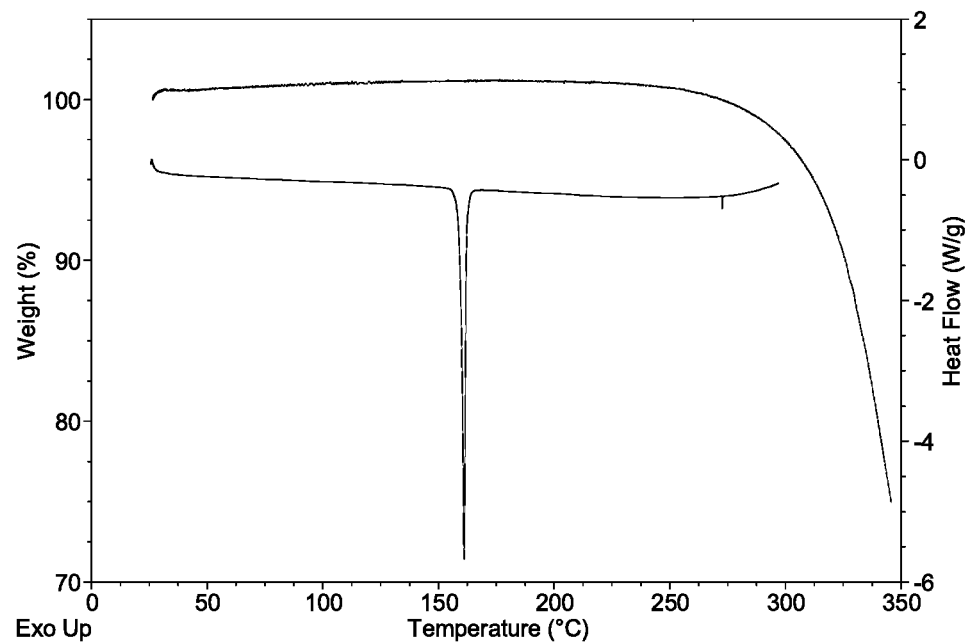
FIG. 14 shows the TGA/DSC pattern of crystal form I.

Example 10 Preparation of Crystal Form I of the Free Base of the Compound of Formula X Isopropanol (0.5 mL) was added to a reaction flask containing 15 mg of the free base of compound of formula X as the starting sample to form a turbid solution which was magnetically stirred at 15° C. for about 5 days at a speed of about 1000 r/min. The solid was isolated by centrifugation, (centrifuge speed: 10000 rpm; time: 3 minutes) and placed in a fume cupboard at 15° C. to dry, 10 mg of yellow crystalline powder was obtained, yield: 66.7%. The powder X-ray diffraction pattern of the resulting crystal is shown in FIG. 13, and the TGA/DSC pattern is shown in FIG. 14; mp is 160° C.-163° C. The crystal form is defined as crystal form I in the present application.

Example 11 Preparation of Crystal Form I of the Free Base of the Compound of Formula X 1,4-dioxane (1.5 mL) was added to a reaction flask containing 10 mg of the free base of compound of formula X as the starting sample to form a clear solution, the flask was sealed with a sealing film at 15° C. After punctured 3-4 small holes with a needle, the flask was placed in a fume cupboard for slow natural volatilization, after 7 days, the sample was dried to give a yellow crystalline powder 8.7 mg, yield 87%. The powder X-ray diffraction pattern of the resulting crystal is shown in FIG. 13, and the TGA/DSC pattern is characterized in FIG. 14; mp 160° C.-163° C. The crystal form is defined as crystal form I in the present application.

Figure 15:
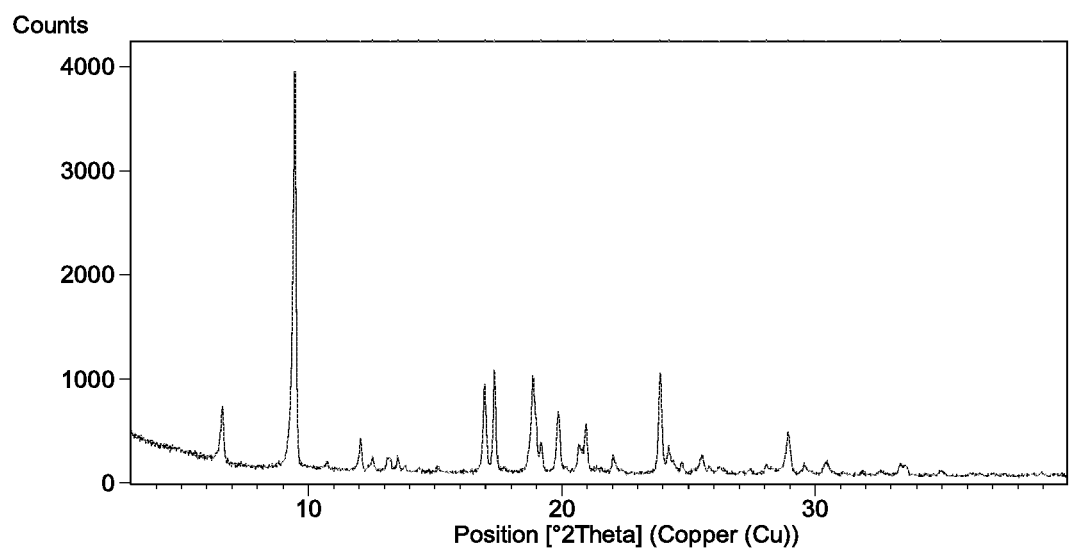
FIG. 15 shows the XRPD pattern of crystal form II.
Figure 16:
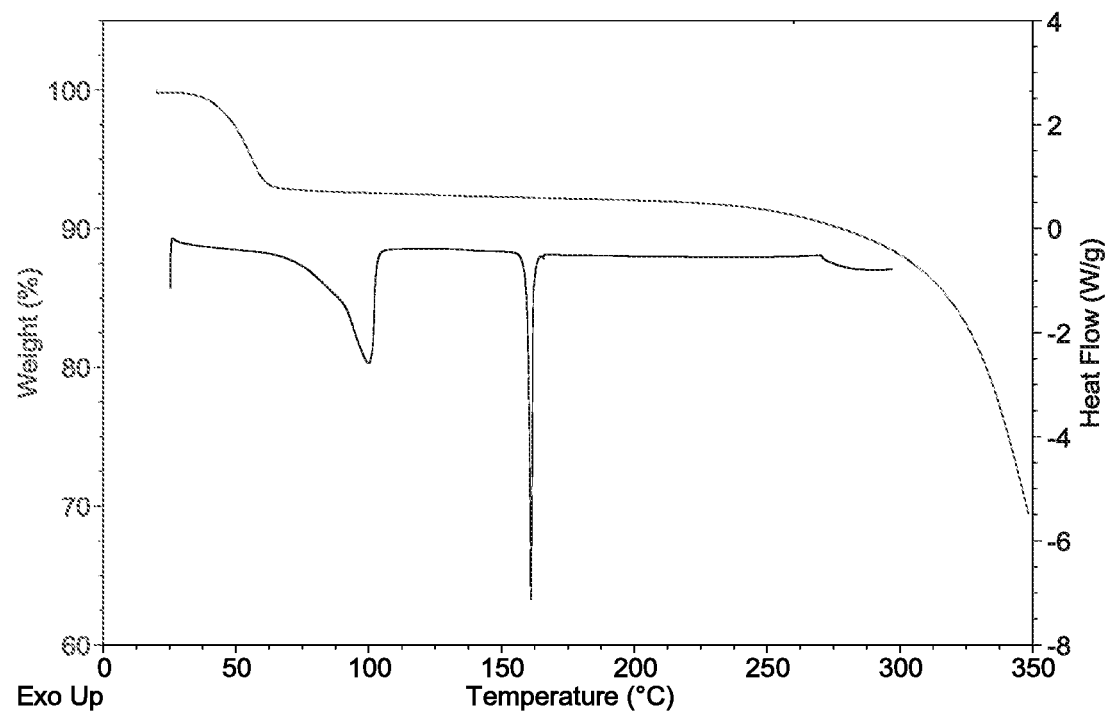
FIG. 16 shows the TGA/DSC pattern of crystal form II.

Example 12 Preparation of Crystal Form II of the Free Base of the Compound of Formula X Acetone (0.4 mL) was added to a reaction flask containing 10.1 mg of the free base of compound of formula X as the starting sample to give a clear solution. The antisolvent H$_2$O was added dropwise to the flask under magnetic stirring at 15° C. After added to 1.0 mL, the solution appeared cloudy and the solid was isolated by centrifugation (centrifuge speed: 10000 rpm; time: 3 minutes), and placed in a fume cupboard at 15° C. to dry, 8 mg of yellow crystalline powder was obtained, yield: 79.2%. The powder X-ray diffraction pattern of the resulting crystal is shown in FIG. 15, the TGA/DSC pattern is shown in FIG. 16, and mp is 160° C.-163° C. The crystal form is defined as crystal form II in the present application.

Example 13 Preparation of Crystal Form II of the Free Base of the Compound of Formula X Ethyl acetate (0.5 mL) was added to a reaction flask containing 15 mg of the free base of compound of formula X as the starting sample to form a turbid solution which was magnetically stirred at 15° C. for about 5 days at a speed of about 1000 r/min. The solid was isolated by centrifugation, (centrifuge speed: 10000 rpm; time: 3 minutes) and placed in a fume cupboard at 15° C. to dry, 13 mg of yellow crystalline powder was obtained, yield: 86.7%. The powder X-ray diffraction pattern of the resulting crystal is shown in FIG. 15, mp is 160° C.-163° C. The crystal form is defined as crystal form II in the present application.

The TGA/DSC pattern for crystal form II is shown in FIG. 16, and the TGA spectrum shows that the weight loss of the sample is about 7.2% when heated to about 80° C. The DSC pattern shows a broad endothermic peak (peak temperature range 98° C.-102° C.) before melting at 158° C.-162° C. The results of Karl Fischer test (moisture test) show that crystal form II contains 7.2% moisture, which is similar to the weight loss before decomposition in TGA characterization results (FIG. 16) of this sample. The XRPD pattern shows that crystal form II is converted to crystal form I after heated to 140° C. and then cooled to room temperature. Crystal form II therefore exists in hydrate form, more preferably in dihydrate form (theoretical weight loss of the free base dihydrate is 6.8%).

Figure 17:
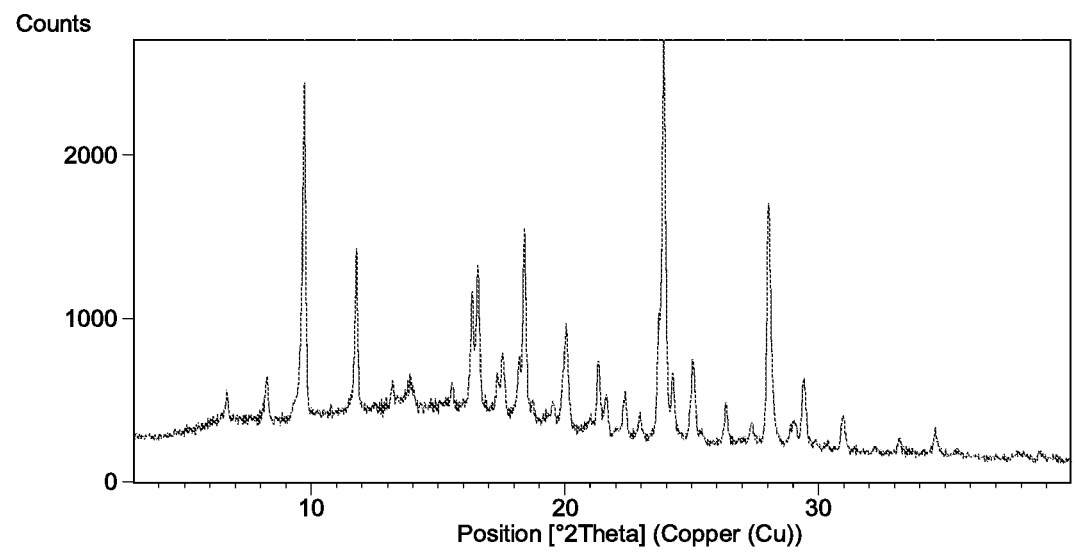
FIG. 17 shows the XRPD pattern of crystal form III.

Example 14 Preparation of Crystal Form III of the Free Base of the Compound of Formula X Methanol (0.5 mL) was added to a reaction flask containing 40 mg of the free base of compound of formula X as the starting sample to form a turbid solution which was magnetically stirred at 15° C. for about 47 hours at a speed of about 1000 r/min. The solid was isolated by centrifugation, (centrifuge speed: 10000 rpm; time: 3 minutes) and placed in a fume cupboard at 15° C. to dry, 36 mg of yellow crystalline powder was obtained, yield: 90%. The powder X-ray diffraction pattern of the resulting crystal is shown in FIG. 17, mp is 160° C.-162° C. The crystal form is defined as crystal form III in the present application.

Example 15 Preparation of Crystal Form III of the Free Base of the Compound of Formula X 10 mg of the free base of compound of formula X as the starting sample was added to a 3.0 mL reaction vial, methanol (4 mL) was added to a 20 mL flask, and the unsealed 3.0 mL vial containing the sample was placed in the 20 mL flask, capped tightly and placed in a fume cupboard for standing, the 3.0 mL vial was taken out after about 7 days, 7.8 mg of a yellow crystalline powder was collected, yield: 78%. The powder X-ray diffraction pattern of the resulting crystal is shown in FIG. 17, and mp is 160° C.-162° C. The crystal form is defined as crystal form III in the present application.

Figure 18A:
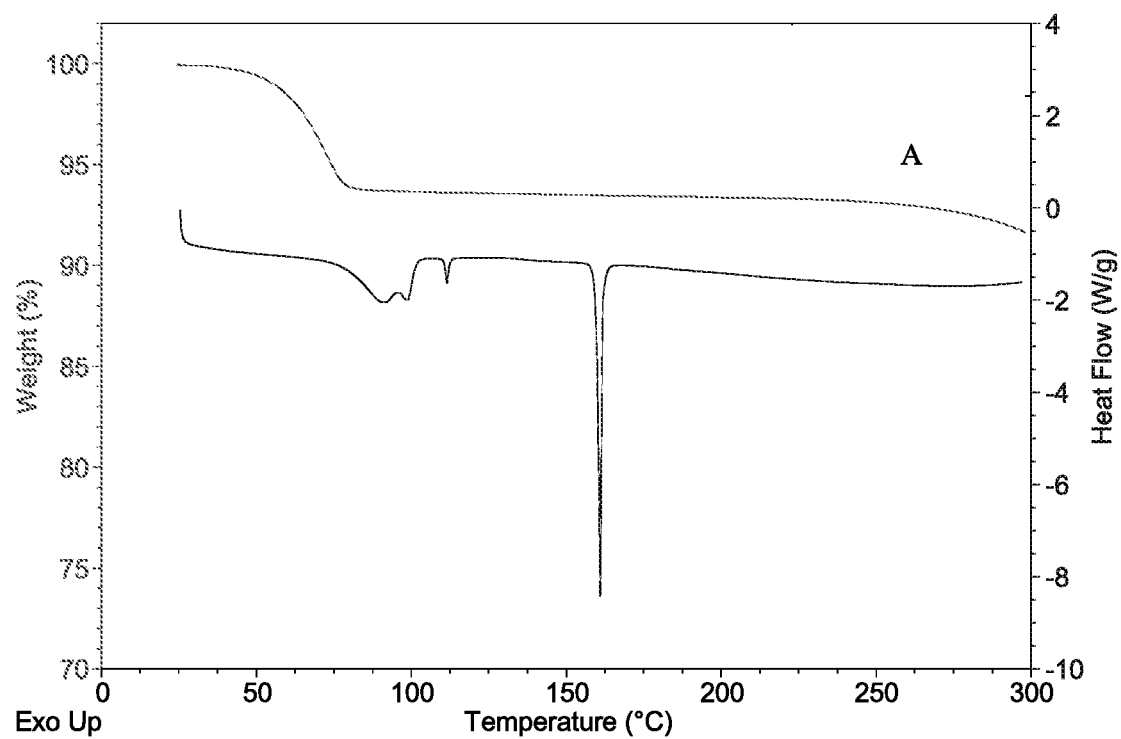
FIG. 18 shows the TGA/DSC pattern (FIG. 18A) and the $^1$HNMR spectrum (FIG. 18B) of crystal form III.
Figure 18B:
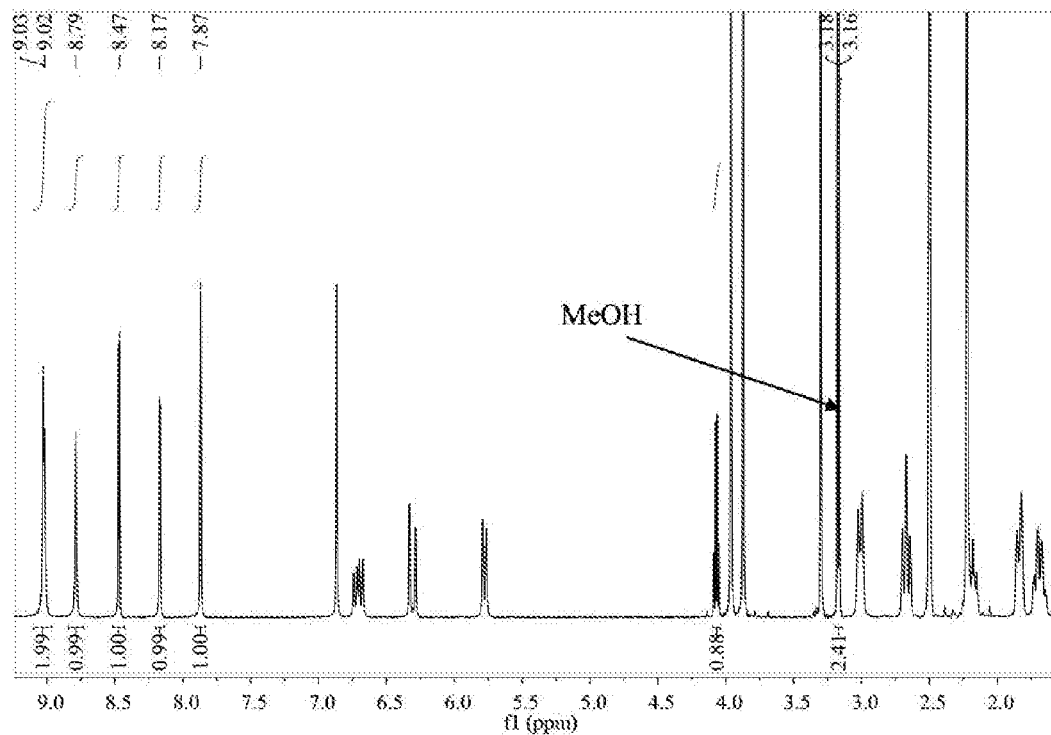

The TGA/DSC pattern of crystal form III is shown in FIG. 18A. The TGA spectrum shows that the weight loss of the sample is about 6.4% before heated to about 130° C. The DSC pattern shows that there are multiple endothermic peaks before melting at 158° C.-162° C. (initial temperature). The XRPD pattern shows that crystal form III is converted to crystal form I after heated to 130° C. and then cooled to room temperature. The $^1$H NMR results of crystal form III (FIG. 18B) show that the methanol content is 4.9%. Crystal form III therefore exists in methanol solvate form.

Figure 19:
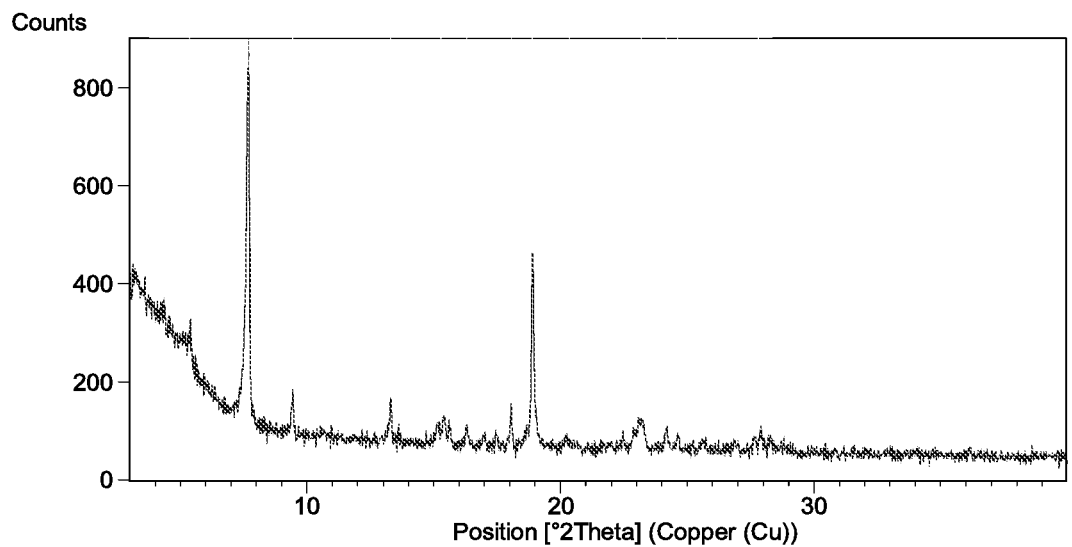
FIG. 19 shows the XRPD pattern of crystal form IV.

Example 16 Preparation of Crystal Form IV of the Free Base of the Compound of Formula X Acetone (1.5 mL) was added to a reaction flask containing 10.4 mg of the free base of compound of formula X as the starting sample to form a clear solution, and the flask was sealed with a sealing film at 15° C. After punctured 3-4 small holes with a needle, the flask was placed in a fume cupboard for slow natural volatilization, after 6 days, the sample was dried to give a yellow crystalline powder 9.3 mg, yield 89.4%. The powder X-ray diffraction pattern of the resulting crystal is shown in FIG. 19, mp 160° C.-162° C. The crystal form is defined as crystal form IV in the present application.

Example 17 Preparation of Crystal Form IV of the Free Base of the Compound of Formula X 10 mg of the free base of compound of formula X as the starting sample was added to a 3.0 mL reaction vial and tetrahydrofuran (0.5 mL) was added to the reaction vial to give a clear solution. Another 4.0 mL of antisolvent n-hexane was weighed into a 20 mL flask. The unsealed 3.0 mL vial containing the sample was placed in the 20 mL flask, capped tightly and placed in a fume cupboard for standing. The solid was precipitated in the 3.0 mL vial after about 4 days, and the vial was removed and dried in air to obtain 8.7 mg of yellow crystalline powder, yield: 87%. The powder X-ray diffraction pattern of the resulting crystal is shown in FIG. 19 and mp is 160° C.-162° C. The crystal form is defined as crystal form IV in the present application.

Figure 20:
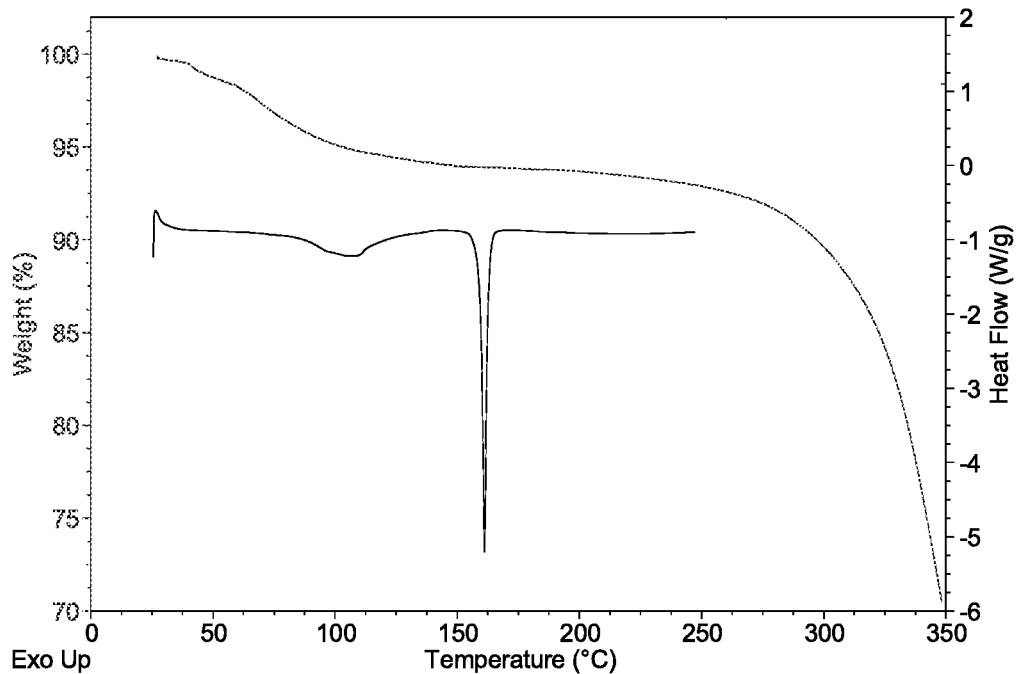
FIG. 20 shows the TGA/DSC pattern of crystal form IV.

The TGA/DSC pattern of crystal form IV is shown in FIG. 20. The TGA spectrum shows that the weight loss of the sample is about 5.8% before heated to about 150° C. The DSC pattern shows that there is an endothermic peak before melting at 158° C.-162° C. (the peak temperature range is 105° C.-109° C.). The XRPD pattern shows that crystal form IV is converted to crystal form I after heated to 130° C. and then cooled to room temperature. Crystal form IV also exists in hydrate form.

Figure 21:
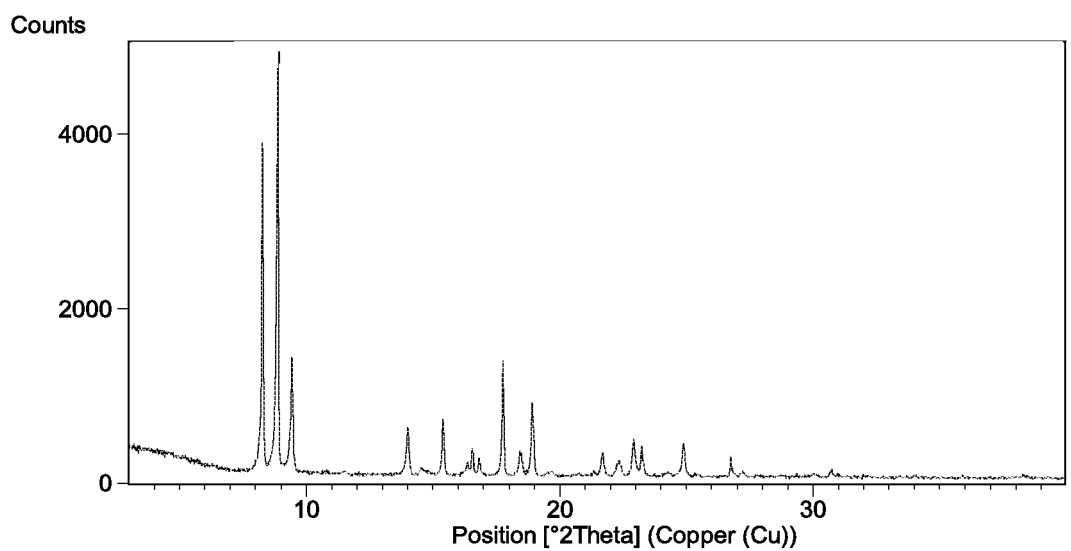
FIG. 21 shows the XRPD pattern of crystal form V.

Example 18 Preparation of Crystal Form V of the Free Base of the Compound of Formula X Ethyl acetate (5 mL) was added to a reaction flask containing 100 mg of the free base of compound of formula X as the starting sample to give a clear solution which was filtered with a 0.22 μm nylon filter into a new 5.0 mL glass vial. The vial was sealed with a sealing film at 21° C. After punctured 3-4 small holes with a needle, the vial was placed in a fume cupboard for natural volatilization. After about 6 days, the sample was dried to give 93 mg of yellow crystalline powder, yield: 93%. The powder X-ray diffraction pattern of the resulting crystal is shown in FIG. 21 and mp is 151° C.-155° C. The crystal form is defined as crystal form V in the present application.

Example 19 Preparation of Crystal Form V of the Free Base of the Compound of Formula X 10 mg of the free base of compound of formula X as the starting sample was added to a 3.0 mL reaction vial, acetone (0.5 mL) was added to the reaction vial to give a clear solution. Another 4.0 mL of antisolvent n-hexane was weighed into a 20 mL flask, and the unsealed 3.0 mL vial containing the sample was placed in the 20 mL flask, capped tightly and placed in a fume cupboard for standing, the solid was precipitated in the 3.0 mL vial after about 4 days, and the vial was taken out and dried in air to obtain 8.4 mg of yellow crystalline powder, yield: 84%. The powder X-ray diffraction pattern of the resulting crystal is shown in FIG. 21, and mp is 151° C.-155° C. The crystal form is defined as crystal form V in the present application.

Figure 22A:
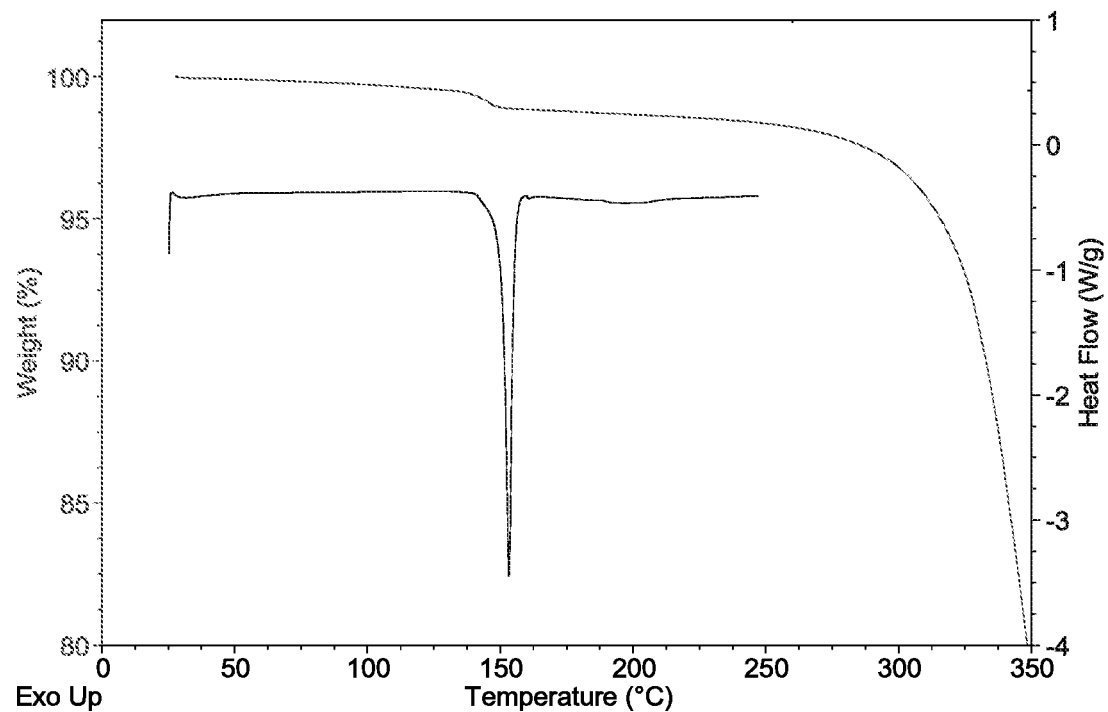
FIG. 22 shows the TGA/DSC pattern (FIG. 22A) and the $^1$HNMR spectrum (FIG. 22B) of crystal form V.
Figure 22B:
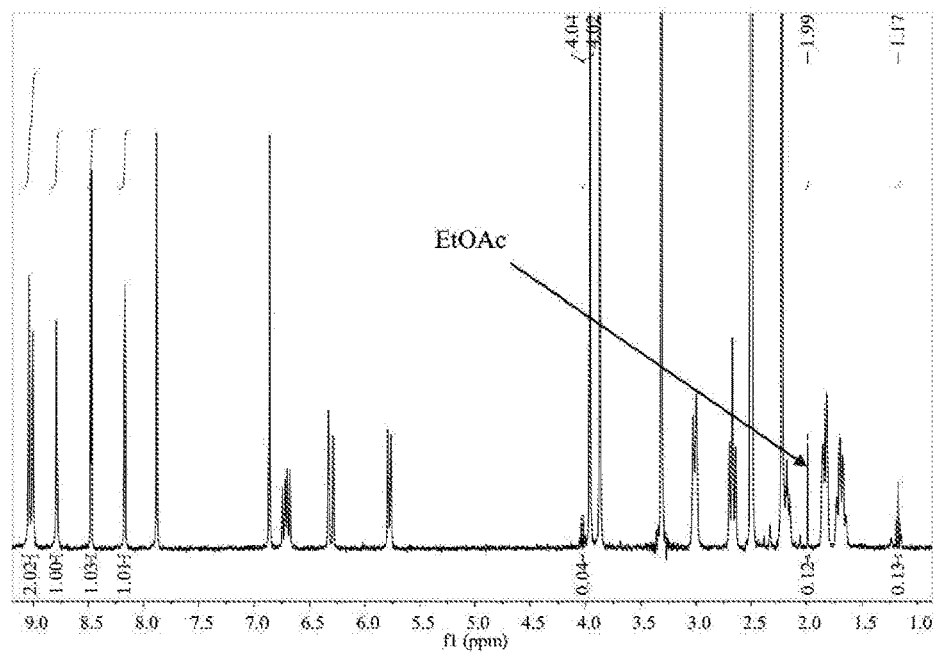

The TGA/DSC pattern of crystal form V is shown in FIG. 22A. The TGA spectrum shows that the weight loss of the sample is about 0.7% between about 130° C. and 160° C., which is consistent with the EtOAc content of this sample detected by $^1$H NMR (FIG. 22B). The DSC pattern shows that there is no significant endothermic or exothermic peak before melting at 149° C.-153° C. (initial temperature). The XRPD pattern shows that crystal form V is converted to crystal form I after stirring in isopropanol at room temperature for about 24 hours. The $^1$H NMR results of crystal form V (FIG. 22B) show that crystal form V exists in ethyl acetate solvate form.

Example 20 Preparation of Various Salts of Compound of Formula X

The corresponding solid acids with a molar ratio of 1:1 to 10 mg of free base were weighed into a reaction flask and a solution of hydrochloric acid, sulfuric acid, phosphoric acid and hydrobromic acid formulated as 0.2 mol/L solution of the corresponding solvent was weighed by volume. 10 mg/mL of a clear solution of the free base of compound of formula X in four corresponding solvents (isopropanol, acetonitrile, ethyl acetate, acetone:water (19:1, v/v) was separately formulated, and 1.0 mL of a clear solution was weighed into the reaction flask containing the corresponding acid, magnetically stirred at a speed of about 1000 r/min at a certain temperature. After the solid was precipitated from the reaction solution, isolated by centrifugation, and collected after vacuum drying at 50° C. for about 1 hour to obtain the corresponding acid salt. When L-lactic acid and benzenesulfonic acid were formulated with a mixed solvent of acetone and water, an appropriate amount of n-hexane was added to the clear solution before stirring. A mixture of salt and acid was obtained in four solvents in the case of mucic acid. The corresponding reaction temperature and time for each acid are shown in Table 1 below:

TABLE 1

| Acid | Amount of acid (mg) | Isopropanol (Condition 1) | acetonitrile (Condition 2) | Ethyl acetate (Condition 3) | Acetone:water (19:1, v/v) (Condition 4) |
|---|---|---|---|---|---|
| hydrochloric acid (0.2M) | 0.1 mL | 15° C./20 hrs | 15° C./20 hrs | 15° C./20 hrs | 15° C./20 hrs |
| sulfuric acid (0.2M) | 0.1 mL | 15° C./20 hrs | 15° C./20 hrs | 15° C./20 hrs | 15° C./20 hrs |
| phosphoric acid (0.2M) | 0.1 mL | 15° C./20 hrs | 15° C./20 hrs | 15° C./20 hrs | 15° C./20 hrs |
| acetic acid | 1.21 | N/A | 5° C./3天 | 5° C./3天 | N/A |
| L-lactic acid | 1.82 | 15° C./20 hrs | 5° C./8 hrs | 15° C./20 hrs | 15° C./3 hrs/ 6 ml n-hexane |
| maleic acid | 2.34 | 15° C./20 hrs | 15° C./20 hrs | 15° C./20 hrs | N/A |
| fumaric acid | 2.35 | 15° C./20 hrs | 15° C./20 hrs | 15° C./20 hrs | 15° C./20 hrs |
| succinic acid | 2.39 | 15° C./20 hrs | 15° C./20 hrs | 15° C./20 hrs | 15° C./20 hrs |
| L-malic acid | 2.71 | 15° C./20 hrs | 15° C./20 hrs | 15° C./20 hrs | 15° C./20 hrs |
| adipic acid | 2.95 | 15° C./20 hrs | 15° C./20 hrs | 15° C./20 hrs | 15° C./20 hrs |
| L-tartaric acid | 3.03 | 15° C./20 hrs | 15° C./20 hrs | 15° C./20 hrs | 15° C./20 hrs |
| hippuric acid | 3.62 | 15° C./20 hrs | 15° C./20 hrs | 15° C./20 hrs | 5° C./8 hrs |
| citric acid | 3.88 | 15° C./20 hrs | 15° C./20 hrs | 15° C./20 hrs | 15° C./20 hrs |
| mucic acid | 4.25 | 15° C./20 hrs | 15° C./20 hrs | 15° C./20 hrs | 15° C./20 hrs |
| glycolic acid | 1.54 | 15° C./20 hrs | 15° C./20 hrs | 15° C./20 hrs | 15° C./20 hrs |
| D-glucuronic acid | 3.92 | 15° C./20 hrs | 15° C./20 hrs | 15° C./20 hrs | 15° C./20 hrs |
| benzoic acid | 2.47 | 15° C./20 hrs | 15° C./20 hrs | 15° C./20 hrs | 15° C./20 hrs |
| gentisic acid | 3.11 | 15° C./20 hrs | 15° C./20 hrs | 15° C./20 hrs | 15° C./20 hrs |
| nicotinic acid | 2.49 | 15° C./20 hrs | 15° C./20 hrs | 15° C./20 hrs | 5° C./8 hrs |
| ethylene disulfonic acid | 4.57 | 15° C./20 hrs | 15° C./20 hrs | 15° C./20 hrs | 15° C./20 hrs |
| oxalic acid | 2.55 | 15° C./20 hrs | 15° C./20 hrs | 15° C./20 hrs | 15° C./20 hrs |
| methanesulfonic acid | 1.94 | 15° C./20 hrs | 15° C./20 hrs | 15° C./20 hrs | 15° C./20 hrs |
| benzenesulfonic acid | 4.57 | 15° C./20 hrs | 15° C./20 hrs | 15° C./20 hrs | 15° C./23 hrs/ 6 ml n-hexane |
| 2-hydroxyethanesulfonic acid | 3.19 | 15° C./20 hrs | 15° C./20 hrs | 15° C./20 hrs | 15° C./20 hrs |
| hydrobromic acid (0.2M) | 0.1 mL | 15° C./20 hrs | 15° C./20 hrs | 15° C./20 hrs | 15° C./20 hrs |

| Salt | The molar ratio of acid to compound of formula X in the salt | Salt | The molar ratio of acid to compound of formula X in the salt |
|---|---|---|---|
| Hydrochloride | 0.9:1 | Sulfate | 1:1 |
| Phosphate | 0.9:1 | Acetate | 1:1 |
| L-lactate | 1:1 | Maleate | 1:1 |
| Fumarate | 1:1 | Succinate | 1:1 |
| L-malate | 1.3:1 | Adipate | 1:1 |
| L-tartrate | 1:1 | Hippurate | 1:1 |
| Citrate | 1:1 | Mucic acid salt | 1:1 |
| Glycolate | 1:1 | D-glucuronate | 1:1 |
| Benzoate | 1:1 | Gentisate | 1:1 |
| Nicotinate | 1:1 | Ethylene disulfonate | 1:1 |
| Oxalate | 1:1 | Methanesulfonate | 1:1 |
| Benzenesulfonate | 1:1 | 2-hydroxyethane sulfonate | 1:1 |
| Hydrobromide | 1:1 | | |

N/A: solid was unavailable.

Example 21 Preparation of Various Salts of Compound of Formula X

To solution A of 300 mg of the compound of formula X, solution B of the corresponding acid (the molar ratio of the acid to the compound of formula X is 1.05:1) was added. After a period of reaction at a certain reaction temperature, the reaction solution was filtered, and the filter cake was washed with a solvent, and dried in vacuo to give the corresponding salt. The original feeding of the reaction and the reaction conditions are shown in Table 2 below.

TABLE 2

| Salt | The molar ratio of acid to compound of formula X in the salt | Solvent A/B/washing solvent | Reaction time/ Reaction temperature | The amount of product |
|---|---|---|---|---|
| fumarate | 0.5:1 | 3 ml ethanol/2 ml ethanol/4 ml ethanol | 2 h/25° C. | 246 mg |
| L-malate | 0.7:1 | 3 ml ethanol/2 ml ethanol/4 ml ethanol | 2 h/25° C. | 286 mg |
| L-tartrate | 1:1 | 4 ml acetone/5 ml acetone/4 ml acetone | 2 h/25° C. | 341 mg |
| citrate | 0.5:1 | 3 ml ethanol/2 ml ethanol/4 ml ethanol | 2 h/25° C. | 312 mg |
| glycolate | 1:1 | 3 ml ethanol/2 ml ethanol/4 ml ethanol | 2 h/25° C. | 230 mg |
| benzoate | 1:1 | 3 ml ethanol/2 ml ethanol/4 ml ethanol | 2 h/25° C. | 282 mg |
| nicotinate | 1:1 | 2.5 ml ethanol/NA/4 ml ethanol | 4 h/78° C. | 182 mg |
| oxalate | NA | 3 ml ethanol/2 ml ethanol/4 ml ethanol | 2 h/25° C. | 307 mg |
| benzenesulfonate | 1:1 | 3 ml ethanol/2 ml ethanol/4 ml ethanol | 2 h/25° C. | 330 mg |
| acetate | 1:1 | 2 ml methyl tert-butyl ether/2 ml methyl tert-butyl ether/4 ml methyl tert-butyl ether | 2 h/25° C. | 307 mg |
| maleate | 1:1 | 3 ml ethanol/2 ml ethanol/4 ml ethanol | 2 h/25° C. | 321 mg |
| succinate | 1:1 | 3 ml ethanol/2 ml ethanol/4 ml ethanol | 2 h/25° C. | 281 mg |
| adipate | 1:1 | 3 ml ethanol/2 ml ethanol/4 ml ethanol | 2 h/25° C. | 357 mg |
| hippurate | 1:1 | 2 ml ethanol/NA/4 ml ethanol | 4 h/78° C. | 219 mg |
| mucic acid salt | 0.5:1 | NA/5 ml 1-Methyl-2-pyrrolidone/6 ml methyl tert-butyl ether | 12 h/100° C. | 244 mg |
| D-glucuronate | 1:1 | 8 ml methanol/NA/NA | 0.5 h/60° C. | 312 mg |
| gentisate | 1:1 | 3 ml ethanol/2 ml ethanol/4 ml ethanol | 2 h/25° C. | 376 mg |
| ethylene disulfonate | 1:1 | 3 ml ethanol/2 ml ethanol/4 ml ethanol | 2 h/25° C. | 361 mg |
| methanesulfonate | 1:1 | 8 ml methanol/9 ml methyl tert-butyl ether/NA | 1 h/25° C. | 300 mg |
| 2-hydroxyethanesulfonate | 1:1 | 3 ml ethanol/2 ml ethanol/4 ml ethanol | 2 h/25° C. | 307 mg |

The physical properties of each salt are shown in Table 3 below:

TABLE 3

| salt | Solid form | Melting point (° C.) |
|---|---|---|
| fumarate | light yellow solid | 214.3-215.4 |
| L-malate | light yellow solid | 188.4-191.7 |
| L-tartrate | yellow solid | 191.3-193.1 |
| citrate | light yellow solid | 168.4-172.0 |
| glycolate | light yellow solid | NA |
| benzoate | yellow solid | 181.0-182.7 |
| nicotinate | light yellow solid | NA |
| oxalate | yellow solid | 227.4-228.9 |
| benzenesulfonate | light yellow solid | 213.0-214.0 |
| acetate | light yellow solid | 139.5-144.2 |
| maleate | light yellow solid | 201.5-202.3 |
| succinate | light yellow solid | 183.9-184.8 |
| adipate | light yellow solid | 195.2-196.2 |
| hippurate | light yellow solid | NA |
| mucic acid salt | light yellow solid | NA |
| D-glucuronate | yellow solid | NA |
| gentisate | light yellow solid | 227.9-228.9 |
| ethylene disulfonate | yellow solid | NA |
| methanesulfonate | yellow solid | NA |
| 2-hydroxyethanesulfonate | yellow solid | NA |

Example 22 Solid Phase Stability Experiment

An appropriate amount of samples were weighed and stored at 25° C./60% RH and 40° C./75% RH (unsealed), respectively. Another set of samples were sealed and kept as a control at 5° C. at the same time. All samples were characterized by XRPD, HPLC and TGA one week later, and the crystal form, purity and weight loss were tested. The test results are shown in Table 4 below:

TABLE 4

| | 5° C. (control)* | | | 25° C./60% RH | | | 40° C./75% RH | |
|---|---|---|---|---|---|---|---|---|
| Samples of compound | Purity (%) | Weight loss (%) | crystal transition | Relative purity (%) | Weight loss (%) | crystal transition | Relative purity (%) | Weight loss (%) |
| crystal form A | 99.45 | 3.0 | no | 100.0 | 4.3 | no | 100.0 | 3.4 |
| crystal form B | 99.56 | 4.1 | no | 100.0 | 4.6 | no | 100.0 | 4.5 |
| crystal form C-1 | 99.39 | 0.1 | no | 100.0 | 1.2 | no | 100.0 | 1.3 |
| crystal form D | 99.37 | 1.6 | no | 100.0 | 1.3 | no | 100.0 | 1.2 |

TABLE 4-continued

| | 5° C. (control)* | | | 25° C./60% RH | | | 40° C./75% RH | |
|---|---|---|---|---|---|---|---|---|
| Samples of compound | Purity (%) | Weight loss (%) | crystal transition | Relative purity (%) | Weight loss (%) | crystal transition | Relative purity (%) | Weight loss (%) |
| crystal form E | 99.30 | 0.1 | no | 100.0 | 0.5 | no | 100.0 | 0.4 |
| the free base as the starting sample | 99.23 | 5.1 | no | 100.0 | 5.3 | no | 100.0 | 6.2 |

Figure 23:
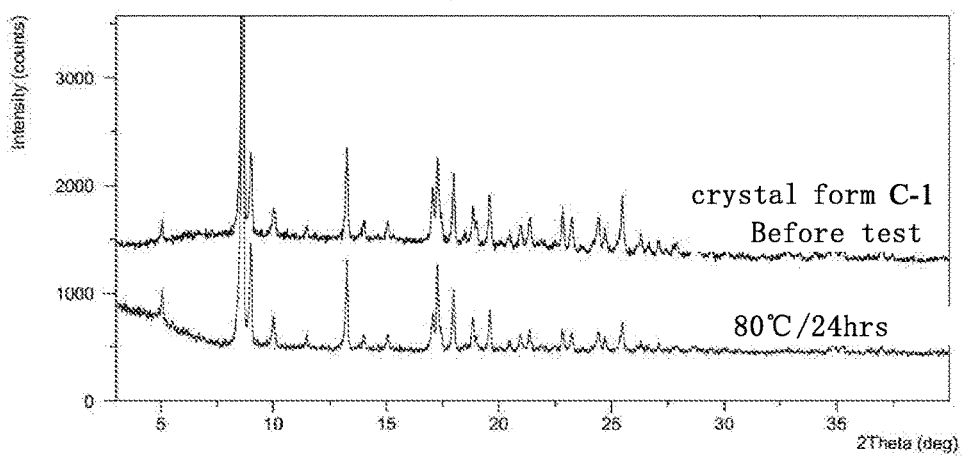
FIG. 23 shows the XRPD comparison of crystal form C-1 before and after being placed at 80° C. for 24 hours.
Figure 24:
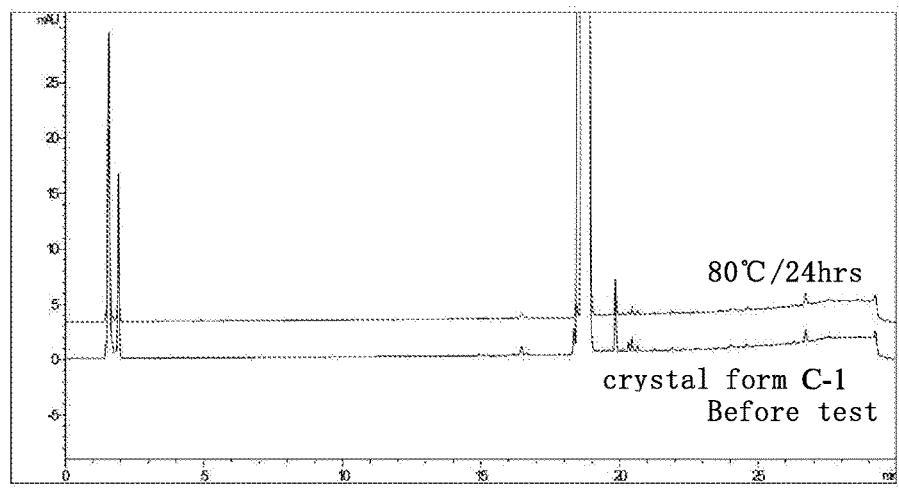
FIG. 24 shows the HPLC comparison of crystal form C-1 before and after being placed at 80° C. for 24 hours.

*a set of samples was stored at 5° C. for evaluation.
Relative purity: compared with the control The above salt forms of the compound of formula X, the free base starting sample and HPLC purity did not change obviously, indicating that the crystal forms of the above salts of the compound of formula X have good physical and chemical stability. TGA test results showed that the crystal forms of the above salts showed less weight loss after being stored at 25° C./60% RH and 40° C./75% RH for a week, which further confirmed that the crystal forms of the above salts of the compound of formula X had better physical stability.

crystal form C-1 was stored at 80° C. for 24 hours and samples were collected for XRPD and HPLC characterization. As illustrated in FIG. 23 and FIG. 24, the crystal form and HPLC purity of crystal form C-1 did not change before and after the test, indicating that crystal form C-1 had better physical and chemical stability.

Example 23 Dynamic Solubility Experiment

The dynamic solubility of the crystal forms of the salts of the compound of formula X and the free base starting sample in water and three biological solvents: simulated gastric fluid (SGF), fasting state simulated intestinal fluid (FaSSIF), feeding state simulated intestinal fluid (FeSSIF) was tested at room temperature. In the experiment, 20 mg of solid and 2 ml of solvent were mixed in a 4 ml centrifuge tube, and the tube was sealed and fixed on a rotating plate at a speed of 25 rpm. One hour later, crystal form B, crystal form C-1, crystal form D and crystal form E samples were observed to be completely dissolved in each of the four solvents and samples were tested for accurate concentration and pH respectively; after 24 hours of equilibration, no solid precipitation was observed in the clear solution, and the HPLC purity of the solution was tested. It can be seen from the results that all samples show no degradation and precipitation after 24 hours of dispersion. The results are shown in Table 5.

TABLE 5

| | FaSSIF | | | FeSSIF | | | SGF | | | 水 | | |
|---|---|---|---|---|---|---|---|---|---|---|---|---|
| Samples of compound | Solubility * | pH * | Phenomenon ** | Solubility * | pH * | phenomenon ** | Solubility * | pH * | Phenomenon ** | Solubility * | pH * | phenomenon ** |
| crystal form B | ≥8.8 | 6.2 | clarified | ≥8.6 | 5.0 | clarified | ≥8.4 | 2.3 | clarified | ≥9.1 | 4.8 | clarified |
| crystal form C-1 | ≥8.9 | 5.8 | clarified | ≥8.7 | 5.0 | clarified | ≥8.3 | 2.2 | clarified | ≥9.0 | 4.2 | clarified |
| crystal form D | ≥8.3 | 4.8 | clarified | ≥8.2 | 4.8 | clarified | ≥8.5 | 2.7 | clarified | ≥8.8 | 3.9 | clarified |
| crystal form E | ≥8.0 | 5.3 | clarified | ≥8.3 | 4.9 | clarified | ≥8.7 | 3.5 | clarified | ≥9.0 | 4.7 | clarified |
| the free base as the starting sample | 4.2 | 7.0 | turbid | ≥10.5 | 5.4 | clarified | ≥8.5 | 6.3 | clarified | 0.01 | N/A | turbid |

* Solubility (mg/ml) and pH measured after 1 hour of solid dispersion.
** Phenomenon observed after 24 hours of solid dispersion.
N/A pH data was not collected due to the less remaining supernatant after solid isolation.
all of crystal form B, crystal form C-1, crystal form D and crystal form E have good solubility in three biological solvents and the solubility of the crystal form of salt in water and FaSSIF increased significantly (>8 mg/mL) compared with the free base.

Example 24 Hygroscopicity Experiment

The crystal form C-1 and crystal form E were dried at 0% RH to remove the adsorbed solvent or water before starting the test. Test for Crystal form B was started from 40% RH.

Figure 25:
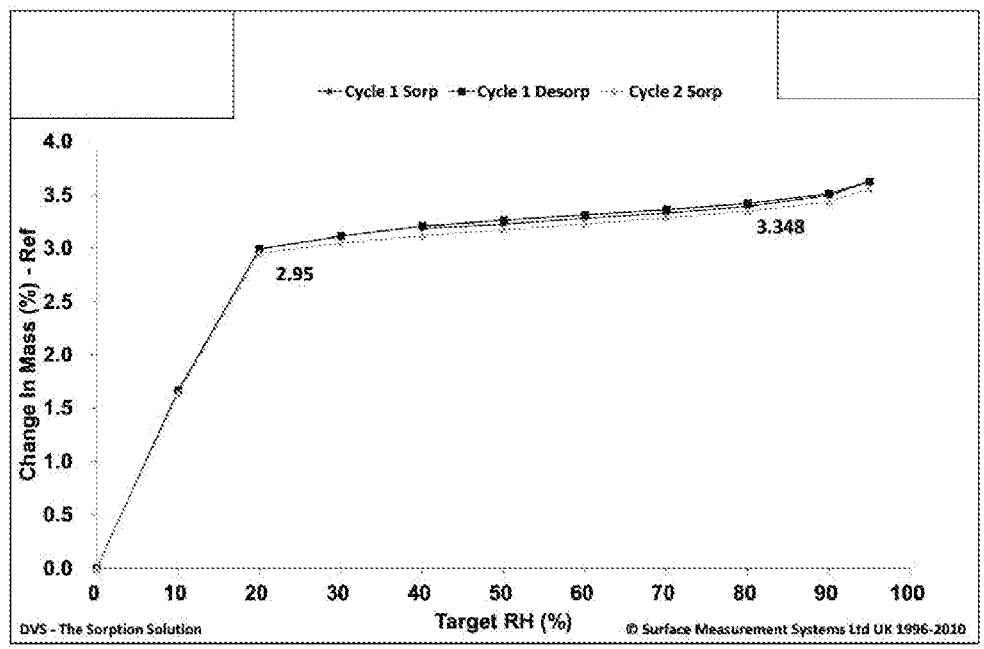
FIG. 25 shows the DVS pattern of crystal form B.
Figure 26:
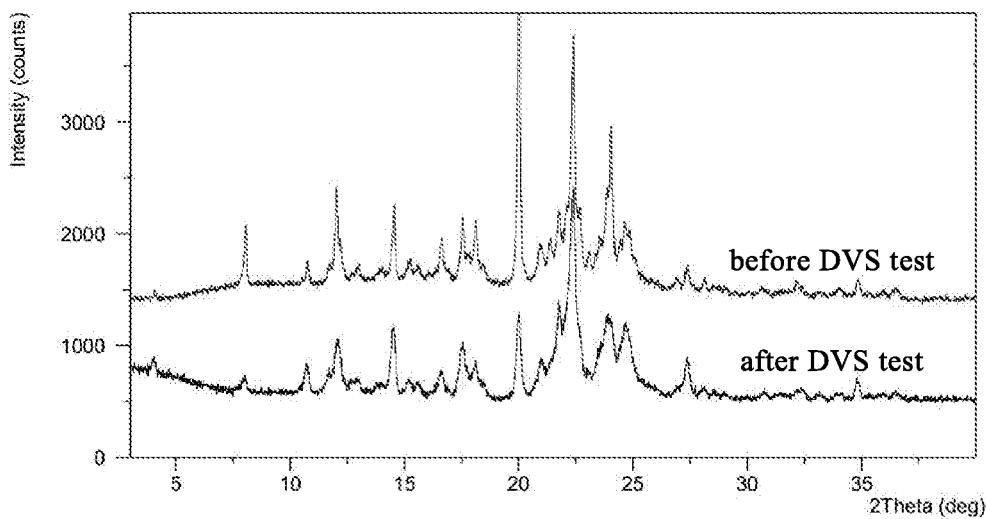
FIG. 26 shows the XRPD comparison of crystal form B before and after DVS test.

The DVS test results of crystal form B are shown in FIG. 25. The rate of weight loss increases when the humidity is reduced to 20% RH at 25° C. The XRPD comparison of the samples before and after the DVS test is shown in FIG. 26, indicating that crystal form B does not change before and after the DVS test.

Figure 27:
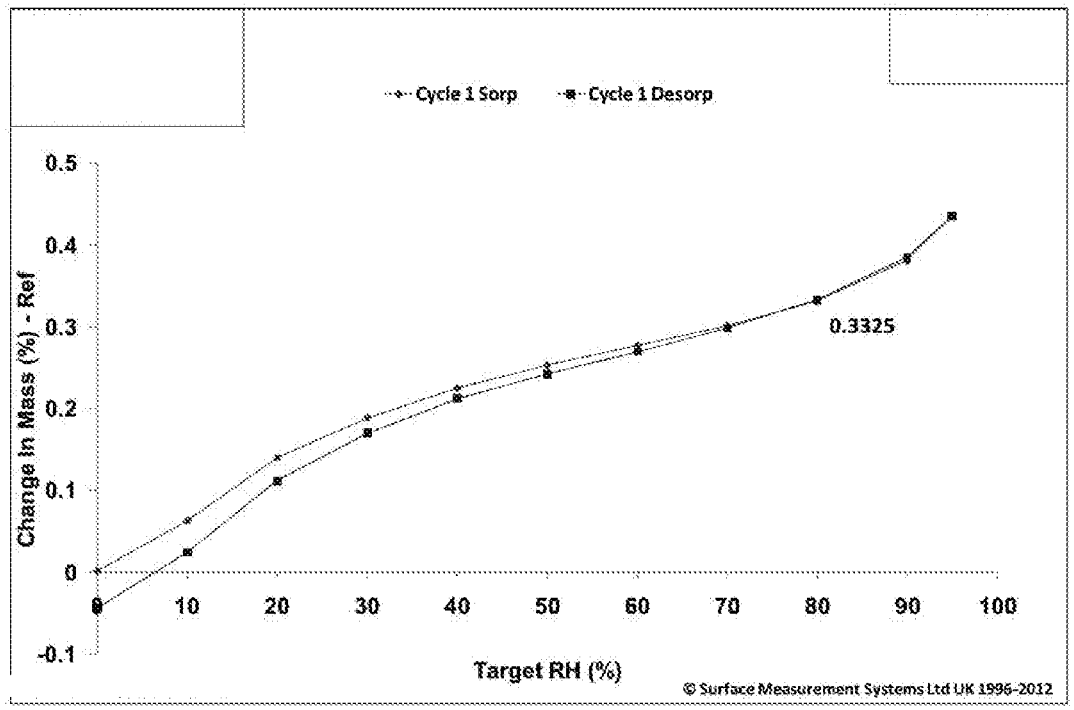
FIG. 27 shows the DVS pattern for crystal form C-1.
Figure 28:
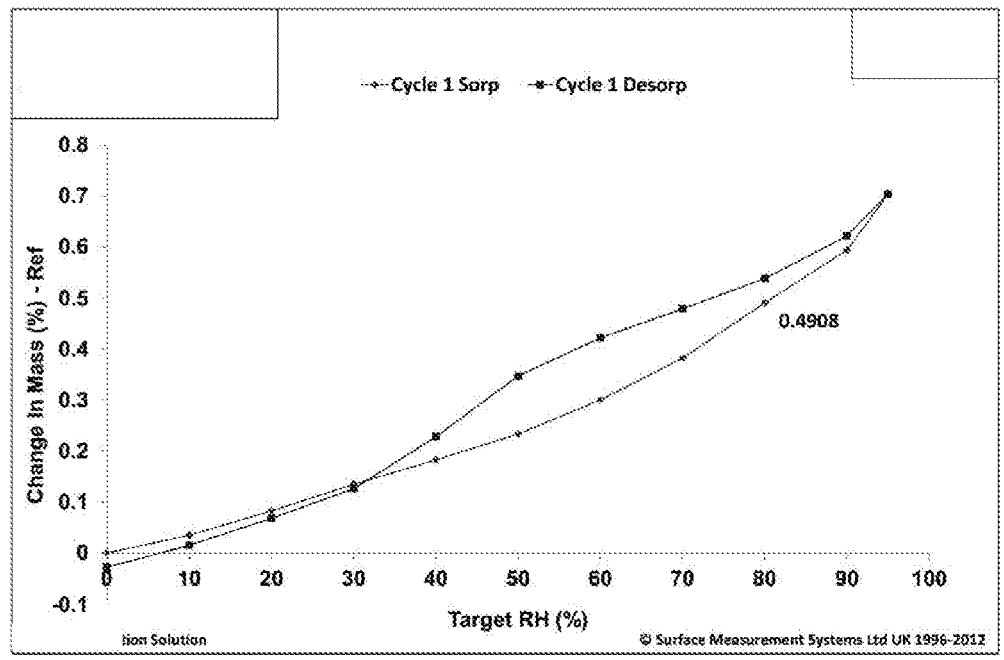
FIG. 28 shows the DVS pattern for crystal form E.

The DVS test results of crystal form C-1 and crystal form E were shown in FIG. 27 and FIG. 28 respectively. Crystal form C-1 and crystal form E absorbed 0.3% and 0.5% moisture respectively when the humidity increased to 80% RH at 25° C., indicating that both anhydrous crystal forms are slightly hygroscopic. The crystal form of two samples before and after the DVS test did not change.

Example 25 Solubility Experiment for Maleate

An appropriate amount of the maleate prepared according to Example 20 condition 2 was added to the volumetric flask at room temperature, and a single organic solvent or mixed solvent was added in small quantities and many times to the flask until the solution was clear or no solid particles were present to determine the crude solubility of maleate in different solvents, the results are shown in Table 6 below.

TABLE 6

| Solvent | Solubility S (mg/ml) | Solvent | Solubility S (mg/ml) |
|---|---|---|---|
| methanol | 7.0 < S < 10.5 | 1,4-dioxane | S < 1.0 |
| ethanol | S < 1.1 | acetonitrile | 1.4 < S < 1.5 |
| isopropanol | S < 0.9 | dichloromethane | 4.6 < S < 5.8 |
| acetone | S < 1.1 | acetic acid | 3.8 < S < 4.8 |
| methyl isobutyl ketone | S < 0.9 | n-hexane | S < 1.0 |
| ethyl acetate | S < 0.9 | toluene | S < 1.1 |
| isopropyl acetate | S < 1.0 | dimethyl sulfoxide | S > 22.0 |
| methyl tert-butyl ether | S < 1.0 | N,N-dimethylacetamide | S > 20.0 |
| tetrahydrofuran | S < 1.2 | N-methylpyrrolidone | S > 23.0 |
| 2-methyltetrahydrofuran | S < 0.9 | water | 10.0 < S < 20.0 |

Example 26 Stability Study of Crystal Form II

The DVS test was performed on crystal form II sample at a constant temperature of 25° C. The DVS results (FIG. 29) show that the sample has essentially no weight loss at humidity above 10% RH, indicating that crystal form II has good stability.

Example 27: Wild Type EGFR and Mutant EGFR Kinase Inhibition Test

All the following reagents used in z-lyte test are commercially available from Invitrogen.

The inhibitory effects of compounds to be tested on double mutant EGFR kinase (EGFR T790M/L858R Kinase) (Invitrogen, PV4879) and wild-type EGFR kinase (EGFR WT) (Invitrogen, PV3872) were measured by z-lyte methods.

The working concentration of each component in 10 μl T790M/L858R kinase reaction system was: 25 μM ATP, 0.08 (or 0.1) ng/μl EGFR T790M/L858R kinase, 2 μM Tyr04 substrate (Invitrogen, PV3193, similarly hereinafter). After the compounds (i.e., test compounds) prepared by the above-mentioned examples described herein were added, the concentration of DMSO was 2 vol %.

The working concentration of each component in 10 μl EGFR WT kinase reaction system was: 10 μM ATP, 0.8 ng/μl EGFR WT kinase, 2 μM Tyr04 substrate. After the test compounds were added, the concentration of DMSO was 2 vol %.

Test Methods:

10 mM stock solutions of the test compounds dissolved at room temperature were gradiently diluted by 4% DMSO in water to final concentrations of 10-0.005 μM. To each well were added 2.5 μl of solution of the test compounds and 5 μl mixture of the EGFR T790M/L858R kinase (or EGFR WT kinase) and Tyr04 substrate diluted by reaction buffer, and then 2.5 μl of ATP was added to initiate the reaction. Reaction buffer instead of ATP were added to C1 wells, no drugs were added to C2 wells, and the phosphorylated substrates were added to C3 wells according to the instruction.

The reaction was performed on a shaking table at room temperature for 60 min. Afterwards, 5 μl of Development Reagent B (Invitrogen) was added, and reacted on a shaking table at room temperature for 60 min. The plates were read on a VictorX5 Microplate Reader (PerkinElmer), for measuring the absorbance at excitation wavelength of 405 nm, and emission wavelength of 450 nm and 520 nm. (For example, $C3_{520}$ nm represents the reading at 520 nm of C3 well).

Inhibition ratio was calculated (according to the instructions of Invitrogen, PV3193) as follows:

$ER$=Coumarin Emission (450 nm)/Fluorescein Emission (520 nm)  1,

Phosphorylation ratio=$(1-((ER \times C3_{520\,nm} - C3_{450\,nm})/((C1_{450\,nm} - C3_{450\,nm}) + ER \times (C3_{520\,nm} - C1_{520\,nm}))) \times 100\%$  2, Inhibition ratio (IR)=(1−phosphorylation ratio of the test compound)/(phosphorylation ratio of $C2$))×100%  3, $IC_{50}$ was determined by fitting calculation with XLFIT 5.0 (IDBS company, UK).

The results of inhibitory activity and selective inhibitory activity against enzyme were shown in Table 7.

TABLE 7

| Compound | T790M/L858R ($IC_{50}$/nM) | EGFR WT ($IC_{50}$/nM) | selective inhibitory activity against enzyme [$IC_{50}$(EGFRWT)/$IC_{50}$(T790M/L858R)] |
|---|---|---|---|
| the free base of compound of formula X | 8 | 102 | 12.75 |
| BIBW2992 | 5 | 1 | 0.2 |
| comparative compound 1 | 2 | 3 | 1.5 |

It can be seen from Table 7 that the free base of compound of formula X of the invention showed strong inhibitory activities against EGFR mutant enzyme (T790M/L858R) but weak inhibitory activities against EGFR wild-type enzyme (T790M WT). The compounds of the present invention had significant selective inhibitory activities against EGFR mutant enzyme compared with the positive control BIBW2992 (afatinib). The selectivity was 8.5 times higher than that of the comparative compound 1 (specific structure was shown below, and can be found in WO2013014448A1).

comparative compound 1

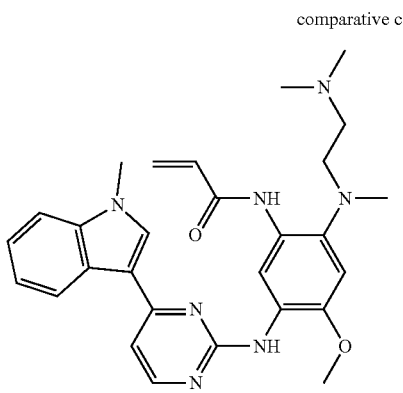

Example 28 Test of Cytostatic Activity by MTT (3-(4,5-dimethyl-thiazol-2)-2,5-diphenyl tetrazolium bromide) Method MTT assay used the method well known to those skilled in the art, and the reagents used in the method can be commercially obtained.

2.1 Test Method:

Firstly, the medium was removed and 1 ml of 0.25% trypsin/EDTA (Gibco, 25200-056) was added. After rinsed for one time, 1.5 ml trypsin/EDTA was added to digest the adherent cells until the cells detached, and then 3.5 ml of medium was added to terminate the trypsinization. The digested cell suspension was transferred to a 15 ml falcon tube, and spun at 1300 rpm for 3 min, the supernatant was discarded, and cells were suspended in fresh medium. The cells were then counted, and diluted to the following concentrations: $2.78 \times 10^4$ cells/ml (A431 and H1975), $3.33 \times 10^4$ cells/ml (NIH3T3). The cells were seeded in 96-well plates (BD 3072), 90 µl/well, and incubated overnight.

A431 cell culture medium: 10% FBS (Gibco, 10099-141) DMEM (Hyclone SH30243.01B);

NIH3T3 cell culture medium: 10% FBS (Gibco, 10099-141) DMEM (Hyclone SH30243.01B);

H1975 cell culture medium: 10% FBS (Gibco, 10099-141) RPMI-1640 (Hyclone SH30809.01B);

20 µl of 10 mM test compound was taken, and the test compound was diluted according to the following concentration gradient (2000, 666.67, 222.22, 74.07, 24.69, 8.23, 2.74, 0.91 µM), serum-free medium was then added (the final concentration: 10, 3.333, 1.111, 0.370, 0.123, 0.041, 0.014, 0.005 µM), and 10 µl of the test compound in each well was added into the cell culture plates, and the final concentration of DMSO was 0.5%.

The cells were added into the incubator after addition of the test compound, and incubated for 72 h, 10 µl of 5 mg/ml MTT (Sigma, M5655) solution was added to each well of the plate, and incubated the 96-well plates at 37° C. 5% $CO_2$ for 4 h in a incubator.

The plates were spun at 2000 rpm for 5 min. After the supernatant was removed, 150 µl DMSO was added to each well, and the plates was shaken on a shaker until the purple crystal completely dissolved (about 10-20 min). Finally, the absorbance at 492 nm was measured by using a microplate reader, and $IC_{50}$ was calculated with XLFIT 5.0 software (UK IDBS company).

The inhibitory activity and selective inhibitory activity of compound against the cell growth were shown in Table 8.

TABLE 8

| Compound No | H1975 cells ($IC_{50}$/nM) | A431 cells ($IC_{50}$/nM) | selective inhibitory activity against the cell growth [$IC_{50}$(A431 cells)/$IC_{50}$(H1975 cells)] |
|---|---|---|---|
| the free base of compound of formula X | 17 | 2391 | 140.6 |
| BIBW2992 | 88 | 29 | 0.33 |
| comparative compound 1 | 13 | 478 | 36.77 |
| comparative compound 2 | 277 | 6659 | 24 |
| comparative compound 3 | 437 | 2967 | 6.8 |

Results of cytotoxicity of the compound against NIH3T3 cells are shown in Table 9:

TABLE 9

| Compound No | NIH3T3 cells MTT assay ($IC_{50}$/nM) |
|---|---|
| the free base of compound of | >10000 |

TABLE 9-continued

| Compound No | NIH3T3 cells MTT assay (IC$_{50}$/nM) |
|---|---|
| formula X | |
| BIBW2992 | 2750 |
| comparative compound 1 | 3552 |

It can be seen from Table 8 that the free base showed strong inhibitory activities against EGFR mutant cells (H1975 cells) but weak inhibitory activities against EGFR wild-type cells (A431 cells), and the compounds of the present invention had significant selective inhibitory activities against EGFR mutant cell growth compared with the positive control BIBW2992 and comparative compound 1. The study found that the activities against H1975 cell and selective inhibitory activities against cell growth significantly reduced after the pyrazole was changed to pyridine or quinoline.

It can be seen from Table 9 that the free base of compound of formula X possessed higher IC$_{50}$ values against NIH3T3 cells, and showed less toxicity.

Example 29 Determination of Activities of EGFR T790M Inhibitor on Cells by ELISA Method The reagents, preparation methods of the solution, as well as the procedures of cell treatments and preparation of lysate, and the test steps of ELISA in the following method were conducted according to the instructions of R&D DYC3570, R&D DYC1095E and R&D DYC1095BE.

1. Reagents and Solutions

Cell lysis buffer: 1% NP-40, 20 mM Tris (pH 8.0), 137 mM NaCl, 10% glycerol, 1 mM NaVO$_3$, 2 mM EDTA.

Cell lysis liquid: cell lysis buffer+10 μg/ml Aprotinin (Sigma), 10 μg/ml Leupeptin (Sigma). All reagents were prepared when using.

1×PBS buffer: NaCl: 0.137 M, KCl: 0.0027 M, Na$_2$PO$_4$-12H$_2$O: 0.01M, KH$_2$PO$_4$: 0.0015M, pH7.4.

Wash buffer: 0.05% Tween-20 in PBS.

Diluent for detecting antibody: 20 mM Tris, 137 mM NaCl, 0.05% Tween-20, 0.1% BSA, pH 7.2-7.4.

Block Buffer: 1% BSA in PBS.

ELISA kits: R&D DYC3570, R&D DYC1095E and R&D DYC1095BE.

2. H1975 cells 2.1 Treatment of H1975 Cells and Preparation of Lysates (1) H1975 cells (Purchased from Cell Cultures Collection Committee, Chinese Academy of Sciences) were innoculated into 96-well plate at 1×10$^4$ cells/well with 90 ul of 10% (V/V) FBS, 1640 medium each well, and incubated at 37° C. with 5% CO$_2$ overnight.

(2) The compounds to be tested were diluted according to the method in MTT assay, and 10 μl of diluted compound or DMSO was added to the corresponding plate well, and incubated at 37° C. with 5% CO$_2$ for 1 h. The final concentration of DMSO was 0.5%. Cell culture system merely treated with DMSO was used as cell control.

(3) 100 μl cell lysate was added after aspirating the medium, sealed and placed in a refrigerator at −80° C. overnight. Cell lysis buffer used as blank control.

2.2 ELISA Assay Procedure

The assay was operated according to the instructions of R&D DYC1095E or R&D DYC1095BE.

(1) R&D capture antibody ((DYC1095BE or DYC1095E)) was diluted with PBS at 1:180, and ELISA plate (Corning costar 42592) was coated with 100l/well of the diluted antibody, and incubated at 25° C. overnight under shaking;

(2) 360 μl of wash buffer was used for washing for three times;

(3) 300 μl of block buffer was added, incubated at 25° C. for 2 hours under shaking;

(4) 360 μl of wash buffer was used for washing for three times;

(5) 40 μl of cell lysis buffer and 60 μl of cell lysates were added, and incubated at 25° C. for 2 h under shaking;

(6) 360 μl of wash buffer was used for washing for three times;

(7) Detection antibody was diluted according to a predetermined ratio as stipulated in kit instructions by using Diluent for detecting antibody, and 100 of the diluted Detection Antibody was added to each well, and incubated at 25° C. for 1 h under shaking in darkness;

(8) 360 μl of wash buffer was used for washing for three times;

(9) reagent A and reagent B of TMB substrate (R & D DY999) were mixed at 1:1, and 100 μl of substrate was added to each well, and incubated at 25° C. for 20 minutes under shaking in darkness;

(10) 50 μl of 2N H$_2$SO$_4$ was added to each well;

(11) The OD450 values and OD570 values of the cell control, blank control and compound treatment were measured respectively by using microplate reader (Thermo Multiskan K3), and the corresponding OD570 values were subtracted from OD450 values of the same wells to get the OD$_{cell}$, OD$_{blank}$ and OD$_{compound\ treatment}$ respectively.

2.3 Data Analysis

Inhibition ratio (%)=100%×(OD$_{cell}$−OD$_{compound\ treatment}$)/(OD$_{cell}$−OD$_{blank}$)

2.4 IC$_{50}$ values were calculated with XLFIT 5.0 software from the calculated inhibition ratio (shown in Table 10).

3. A431 Cells 3.1 Treatment of A431 Cells and Assay Procedure (1) The A431 cells (Purchased from Cell Cultures Collection Committee, Chinese Academy of Sciences) were innoculated into 96-well plate at 1×10$^4$ cells/well with 90 ul of 10% FBS, 1640 medium each well, and incubated at 37° C. with 5% CO$_2$ overnight.

(2) The medium of A431 cells was changed to 90 ul of DMEM FBS free medium, and incubated overnight.

(3) The compounds to be tested were diluted according to the method in MTT assay, 10 μl of diluted compound or DMSO was added to the corresponding plate well, and incubated at 37° C. with 5% CO$_2$ for 1 h. The final concentration of DMSO was 0.5%. 10 μl of 2 μg/L EGF (R&D, 236-EG-01M) was then added to each well except the cell control well, 10 μl of serum-free DMEM was added to the well, and incubated for 45 minutes; the EGF-free and compound treatment-free cells were used as cell control, and the compound treatment-free but only EGF-treated cells were used as EGF control.

(4) 100 μl cell lysate was added after aspirating the medium, sealed and placed in refrigerator at −80° C. overnight.

3.2 ELISA Assay Procedure

The assay was operated according to the instructions of R&D DYC3570E.

(1) R&D capture antibody (DYC3570E) was diluted with PBS by 1:180, and the diluted antibody was added into ELISA plate (Corning costar 42592) at 100 μl/well, and incubated at 25° C. overnight under shaking;

(2) 360 μl of wash buffer was used for washing for three times;

(3) 200 μl of block buffer was added, and incubated at 25° C. for 2 hours under shaking;

(4) 360 μl of wash buffer was used for washing for three times;

(5) 40 μl of cell lysis buffer and 60 μl of cell lysates were added, and incubated at 25° C. for 2 h under shaking;

(6) 360 μl of wash buffer was used for washing for three times;

(7) Detection antibody was diluted according to a predetermined ratio of kit instruction by using Diluent for detecting antibody, and 100 μl of the diluted Detection Antibody was added to each well, and incubated at 25° C. for 1 h under shaking in darkness;

(8) 360 μl of wash buffer was used for washing for three times;

(9) reagent A and reagent B of TMB substrate (R & D DY999) were mixed at 1:1, 100 μl of substrate was added to each well, and incubated at 25° C. for 20 minutes under shaking in darkness;

(10) 50 μl of 2N $H_2SO_4$ was added to each well;

(11) The OD450 values and OD570 values of the cell control, blank control and compound treatment were measured respectively by using microplate reader (Thermo Multiskan K3), and the corresponding OD570 values were subtracted from OD450 values of the same wells to get the OD EGF, $OD_{compound}$ and $OD_{cell}$ respectively.

3.3 Data Analysis

Inhibition ratio (%)=100%×($OD_{EGF}$−$OD_{compound}$)/($OD_{EGF}$−$OD_{cell}$)

3.4 $IC_{50}$ values were calculated with XLFIT 5.0 software from the calculated inhibition ratio (shown in Table 10).

Results of cell activities measured by ELISA Assay are shown in Table 10:

TABLE 10

| Compound No. | H1975 cells ($IC_{50}$/nM) | A431 cells ($IC_{50}$/nM) | Selective inhibitory activities of target on cellular level [$IC_{50}$(A431 cells)/$IC_{50}$(H1975 cells)] |
|---|---|---|---|
| the free base of compound of formula X | 34 | 1693 | 50 |
| BIBW2992 | 21 | 5 | 0.24 |
| comparative compound 1 | 29 | 114 | 3.9 |
| comparative compound 2 | 241 | 199 | 0.83 |
| comparative compound 3 | 1139 | 3113 | 2.7 |

It can be seen from results of cell activities measured by ELISA Assay that the compound of formula X of the invention exhibit obvious selective inhibitory activities against target on cellular level compared with the positive control BIBW2992 and comparative compound 1. The study found that the activities against H1975 cell and selective inhibitory activities against target on cellular level significantly reduced or even disappeared after the pyrazole was changed to pyridine or quinoline.

Example 30 In Vivo Test of Rats

LC/MS/MS method was applied for the determination of the drug concentration in plasma at different times after the example compounds were administered via oral gavage to rats in order to study the pharmacokinetic behavior of the compound of the invention in vivo in rats and evaluate their pharmacokinetic characteristics.

Protocol:

Test Animals: healthy Adult male SD rats (weight 200-300 g, 6, fasted) provided by SLAC company;

Administration and Dosage: (5 mg/kg, 5 mL/kg, 0.5% CMC-Na solution) was administered via oral gavage to SD rats.

Blood collection: firstly, the animals which were selected to meet the test requirements prior to administration were weighed. The rats were bound before the blood collection, blood from each administered rat was taken at predetermined time points (gavage: blood was collected at 0.083, 0.25, 0.5, 1, 2, 4, 8, 24 h before and after administration respectively, for 9 time points in total), about 150 μl of blood was collected via tail vein or heart (blood terminal). About 150 μl of blood was collected via orbital or heart (blood terminal). Blood was transferred to a 1.5 ml tube to which $K_2EDTA$ was added previously. The collected blood sample was put on ice, and centrifuged to obtain plasma sample (2000 g, 5 min under 4° C.) within 15 minutes. All the plasma samples were stored at approximately −70° C. until analysis.

LC/MS/MS method was applied to determine the concentrations of the drug. At the same dose and administration, pharmacokinetic parameters of some example compounds of the invention in rats were shown in Table 11:

TABLE 11

| | rat | | | | |
|---|---|---|---|---|---|
| | crystal form A | crystal form B | crystal form C-1 | crystal form D | crystal form E |
| Half-life $T_{1/2}$ (hr) | 7.44 | 7.04 | 7.92 | 6.63 | 7.46 |
| Oral relative bioavailability F | 85.7% | 77.5% | 77.5% | 72.4% | 103% |
| Maximum plasma concentration $C_{max}$(ng/ml) | 93.3 | 93.2 | 86.3 | 84.4 | 117 |
| Area under the curve AUC (hr*ng/mL) | 1379 | 1265 | 1233 | 1202 | 1660 |

It can be seen from pharmacokinetic parameters of compound in rats in vivo that the salts of the present invention were well absorbed, and has obvious absorption effect while exhibiting excellent bioavailability.

Example 31 Pharmaceutical Compositions

Tablets of adipate of the compound of formula X are prepared from the components shown in Table 12 below:

TABLE 12

| | |
|---|---|
| adipate of the compound of formula X (Example 20, condition 2) | 20 g |
| starch | 40 g |
| lactose | 32 g |
| PVP | 3 g |
| sodium carboxymethyl starch | 3 g |
| sodium dodecyl sulfate | 1 g |
| magnesium stearate | 1 g |

Adipate of the compound of formula X and starch are mixed and sieved, and then well mixed with the above other components, and tablets were compressed directly according to a conventional method.

Example 32 Pharmaceutical Compositions

Tablets of crystal form C-1 were prepared from the components shown in Table 13 below:

TABLE 13

| | |
|---|---|
| crystal form C-1 | 15 g |
| starch | 40 g |
| lactose | 37 g |
| PVP | 3 g |
| sodium carboxymethyl starch | 3 g |
| sodium dodecyl sulfate | 1 g |
| magnesium stearate | 1 g |

Crystal form C-1 and the starch are mixed and sieved, and then well mixed with the above other components, and tablets were compressed directly according to a conventional method.

Example 33 Pharmaceutical Compositions

Capsules of crystal form II were prepared from the components shown in Table 14 below:

TABLE 14

| | |
|---|---|
| crystal form II | 20 g |
| starch | 40 g |
| lactose | 32 g |
| PVP | 3 g |
| sodium carboxymethyl starch | 3 g |
| sodium dodecyl sulfate | 1 g |
| magnesium stearate | 1 g |

The form II and starch are mixed and sieved, and then well mixed with the above other components, and filled into ordinary gelatin capsules according to a conventional method.

Example 34 Stability Relationship Study Between Maleate Crystal Form C-1 and Crystal Form C-2

Figure 30:
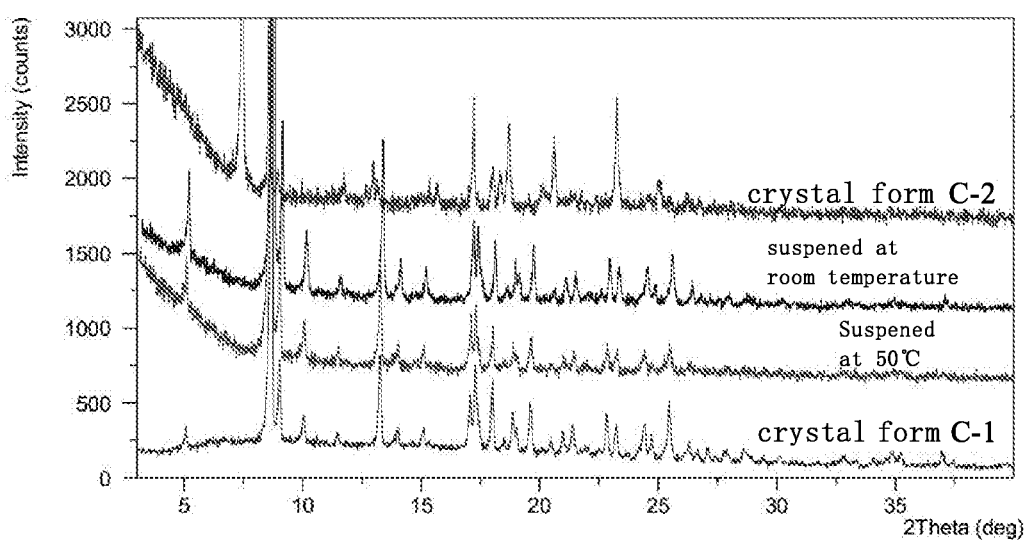
FIG. 30 shows the XRPD overlay for suspension competition between crystal form C-1 and crystal form C-2.

In order to verify the interconversion relationship between crystal form C-1 and crystal form C-2 of maleate in the presence of solvent, a suspension competition test was set up at room temperature and 50° C. respectively. Firstly, the suspension of maleate crystal form C-1 in acetone was prepared at two temperature respectively, and filtered after balancing for about one hour. An equal quantity of crystal form C-1 and crystal form C-2 of maleate (about 5 mg each) was weighed and added to the filtrate and stirred magnetically. The mixture was converted to crystal form C-1 after stirring for 5 minutes at room temperature and 50° C. as shown in FIG. 30, indicating that the maleate crystal form C-1 has a higher thermodynamic stability than crystal form C-2 in the range of room temperature to 50° C.

Figure 31:
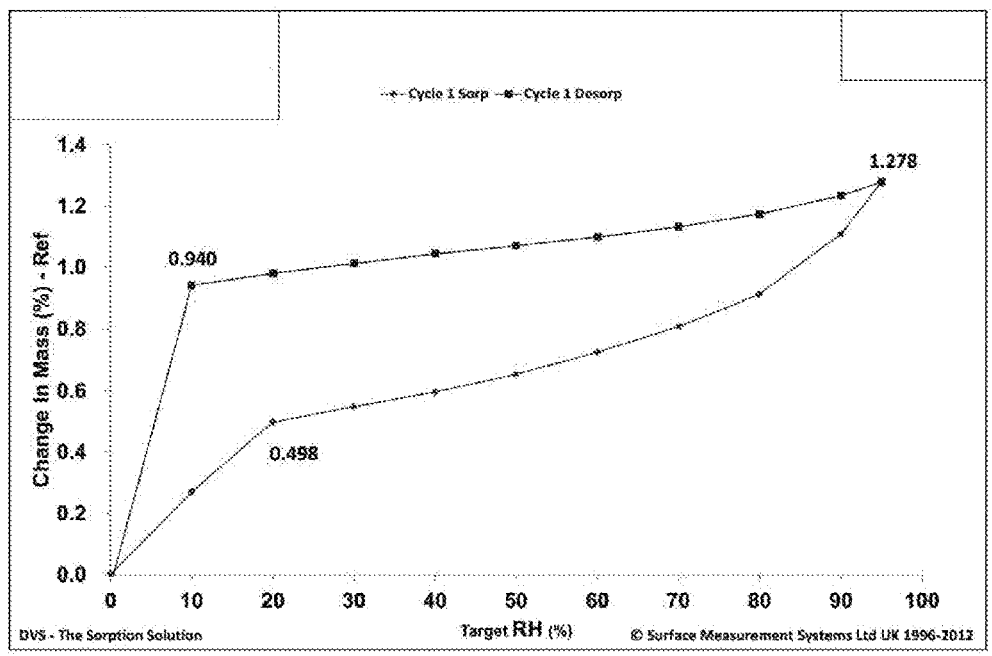
FIG. 31 shows the DVS pattern of crystal form I.

Example 35 Stability Relationship Study of Crystal Form I and Crystal Form II 1) DVS Characterization:

In order to assess the stability of anhydrous crystal form I and hydrate crystal form II under different humidity conditions, DVS assay was performed on samples of anhydrous crystal form I and hydrate crystal form II at constant 25° C. The DVS results of crystal form I samples (FIG. 31) show that the sample continues to absorb moisture as humidity increases.

Figure 29:
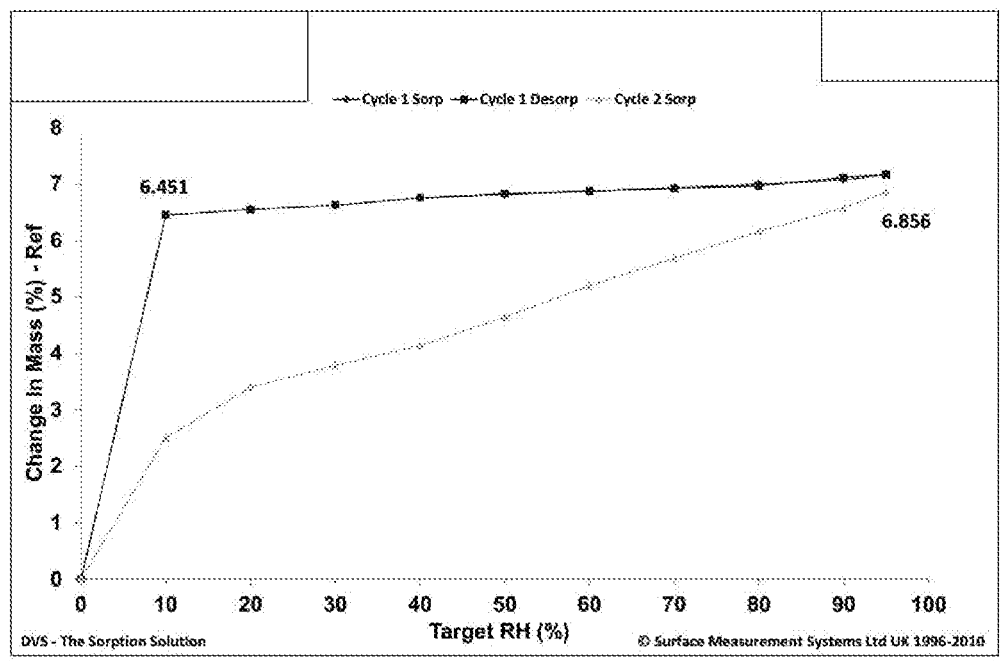
FIG. 29 shows the DVS pattern for crystal form II.
Figure 32:
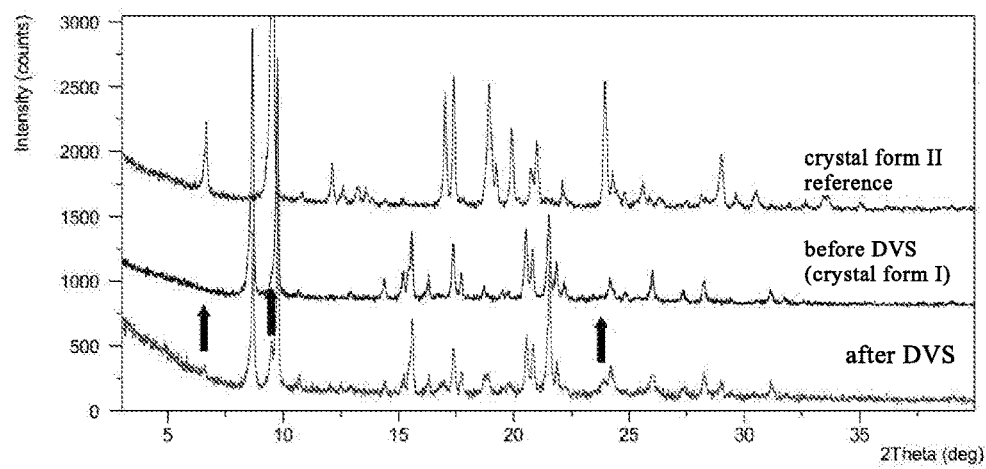
FIG. 32 shows the XRPD comparison of crystal form I before and after DVS test.
Figure 33:
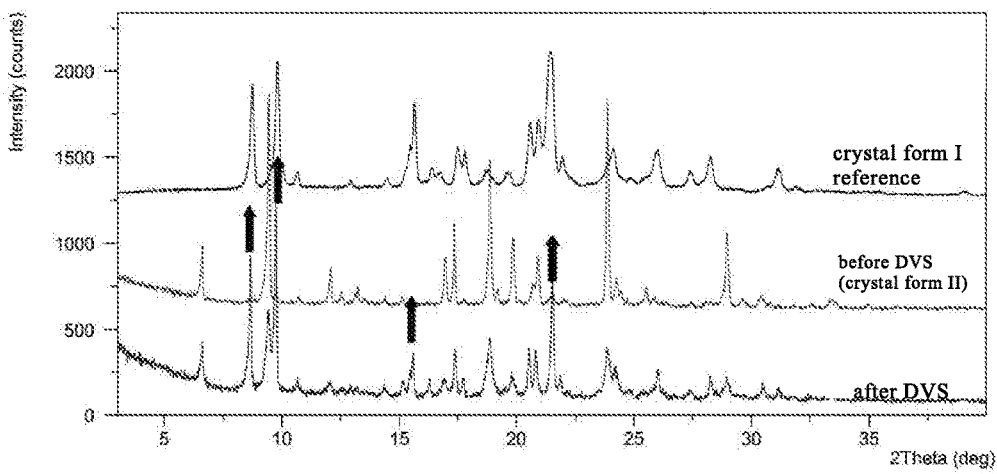
FIG. 33 shows the XRPD comparison of crystal form II before and after DVS test.

When the humidity reaches 20% RH, a turning point appears in the isothermal map of DVS, which is caused by the transition from anhydrous crystal form I to hydrate form II according to the XRPD comparison of the samples before and after the DVS assay shown in FIG. 32. The actual moisture absorbed is less than the moisture content of crystal form II sample due to the slow solid phase transition rate. The isothermal DVS curve of hydrate crystal form II in FIG. 29 shows that the sample has almost no weight loss when humidity is above 10% RH, the sample rapidly dewatered when the humidity is below 10% RH, and the sample gradually reabsorbed moisture as the humidity increased again, and a total of 6.9% of water is absorbed at 95% RH. The comparison of the XRPD characterization results of crystal form II sample before and after DVS assay is shown in FIG. 33, where the characteristic diffraction peaks of crystal form I are also likely caused by the lower solid phase transition rate.

2) Suspension Competition Test

Figure 34:
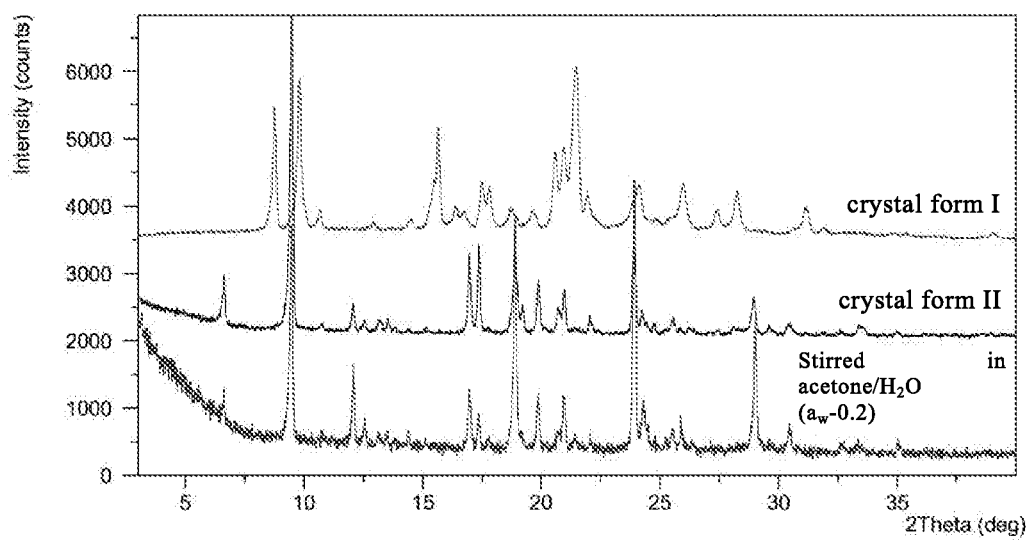
FIG. 34 shows the XRPD comparison of crystal form I and II before and after the suspension competition test.

In order to further confirm the stability relationship between anhydrous crystal form I and hydrate crystal form II under different water activity conditions at room temperature, the mixture of crystal form I and crystal form II was suspended and stirred in acetone/$H_2O$ solvent system with different water activities (aw—0.2/0.4/0.6/0.8). It can be seen from the experimental results in FIG. 34 that the mixture was converted to the hydrate form II after stirring in the selected solvent system for three days at room temperature, indicating that the hydrate form II is more stable at a water activity (aw) equal to or greater than 0.2 at room temperature.

Example 36 Stability Relationship Study of Crystal Form II and Crystal Form IV In order to study the stability relationship between different hydrate crystal form II and IV at room temperature to 50° C., a suspension competition test was set up in aqueous system at room temperature and 50° C. respectively. Firstly, the free base suspension in acetone/$H_2O$ (aw—0.6) was prepared at room temperature and 50° C. respectively. After balancing at the corresponding temperature for about 1 hour, the suspension was filtered to obtain the near saturated solution at the corresponding temperature. An equal quantity of crystal form II and IV samples (about 6 mg each) was added to 0.8 ml of saturated solution to form a suspension which was magnetically stirred (~800 rpm) at room temperature and 50° C. for about 5 minutes, and sampled for XRPD test.

Figure 35:
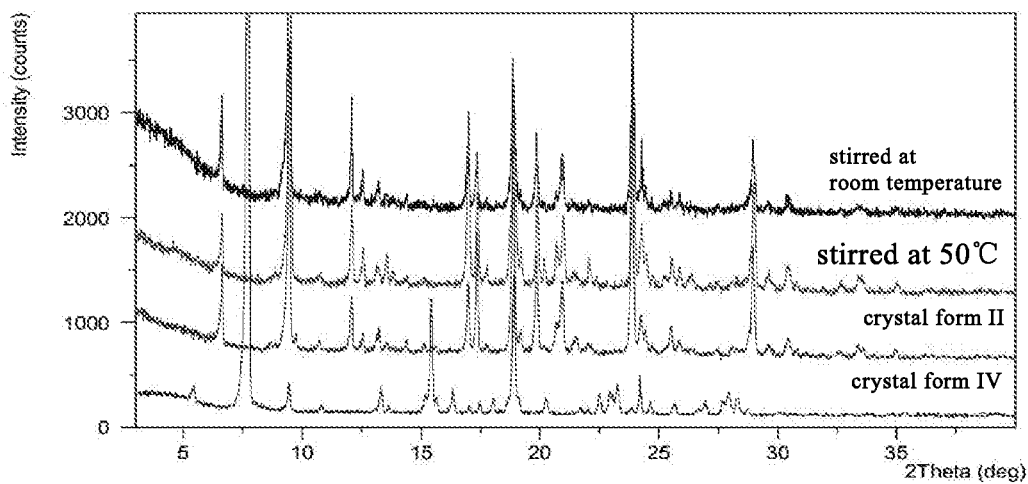
FIG. 35 shows the XRPD comparison of crystal form II and IV before and after the suspension competition test.

It can be seen from the comparative results in FIG. 35 that crystal form IV was quickly converted to hydrate crystal form II at room temperature and 50° C., indicating that hydrate crystal form II is more stable than hydrate crystal form IV at room temperature to 50° C. under aqueous conditions.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

What we claim:

1. A crystalline form of a compound of formula X:

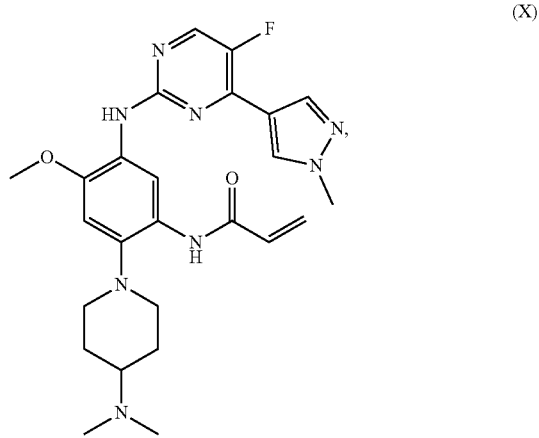 [SMILES: C=CC(=O)Nc1cc(Nc2ncc(F)c(-c3cnn(C)c3)n2)c(OC)cc1N1CCC(N(C)C)CC1]

(X)

wherein the crystalline form is selected from the group consisting of:

1) crystalline form A of a hydrochloride salt of the compound of formula X, wherein the crystalline form A has an X-ray powder diffraction pattern with diffraction angle 2θ(°) values of the following group A1: 8.47±0.10, 20.32±0.10, 23.31±0.10 (the highest peak) and 25.98±0.10;

2) crystalline form B of a phosphate salt of the compound of formula X, wherein the crystalline form B has an X-ray powder diffraction pattern with diffraction angle 2θ(°) values of the following group B1: 11.94±0.10, 19.92±0.10 (the highest peak), 22.27±0.10, 23.93±0.10;

3) crystalline form C-1 of a maleate salt of the compound of formula X, wherein the crystalline form C-1 has an X-ray powder diffraction pattern with diffraction angle 2θ(°) values of the following group C-1-1: 8.73±0.10, 13.37±0.10, 18.08±0.10 and 25.55±0.10 (the highest peak);

4) crystalline form C-2 of the maleate salt of the compound of formula X, wherein the crystalline form C-2 has an X-ray powder diffraction pattern with diffraction angle 2θ(°) values of the following group C-2-1: 7.48±0.10 (the highest peak), 8.60±0.10, 20.63±0.10 and 23.27±0.10;

5) crystalline form D of a L-malate salt of the compound of formula X, wherein the crystalline form D has an X-ray powder diffraction pattern with diffraction angle 2θ(°) values of the following group D1:7.47±0.10, 18.75±0.10, 22.69±0.10 (the highest peak) and 24.39±0.10;

6) crystalline form E of an adipate salt of the compound of formula X, wherein the crystalline form E has an X-ray powder diffraction pattern with diffraction angle 2θ(°) values of the following group E1: 7.43±0.10, 18.45±0.10, 21.64±0.10 (the highest peak) and 24.22±0.10;

7) crystalline form I of the compound of formula X, wherein the crystalline form I has an X-ray powder diffraction pattern with diffraction angle 2θ(°) values of the group I-1: 8.74±0.10, 9.80±0.10, 15.63±0.10, and 21.38±0.10 (the highest peak);

8) crystalline form II of the compound of formula X, wherein the crystalline form II has an X-ray powder diffraction pattern with diffraction angle 2θ(°) values of the group II-1: 9.47±0.10 (the highest peak), 17.34±0.10, 18.87±0.10, and 23.89±0.10;

9) crystalline form III of the compound of formula X, wherein the crystalline form III has an X-ray powder diffraction pattern with diffraction angle 2θ(°) values of the group III-1: 9.72±0.10, 18.41±0.10, 23.89±0.10 (the highest peak) and 28.02±0.10;

10) crystalline form IV of the compound of formula X, wherein the crystalline form IV has an X-ray powder diffraction pattern with diffraction angle 2θ(°) values of the group IV-1: 7.69±0.10 (the highest peak), 18.90±0.10; and 11) crystalline form V of the compound of formula X, wherein the crystalline form V has an X-ray powder diffraction pattern with diffraction angle 2θ(°) values of the group V-1: 8.28±0.10, 8.89±0.10 (the highest peak), 9.44±0.10, 17.76±0.10.

2. The crystalline form of claim 1, wherein the X-ray powder diffraction pattern of the crystalline form A is substantially characterized as in FIG. 1;

the X-ray powder diffraction pattern of the crystalline form B is substantially characterized as in FIG. 3;

the X-ray powder diffraction pattern of the crystalline form C-1 is substantially characterized as in FIG. 5;

the X-ray powder diffraction pattern of the crystalline form C-2 is substantially characterized as in FIG. 7;

the X-ray powder diffraction pattern of the crystalline form D is substantially characterized as in FIG. 9; and/or the X-ray powder diffraction pattern of the crystalline form E is substantially characterized as in FIG. 11.

3. A process for preparing a crystalline form of a salt of a compound of formula X:

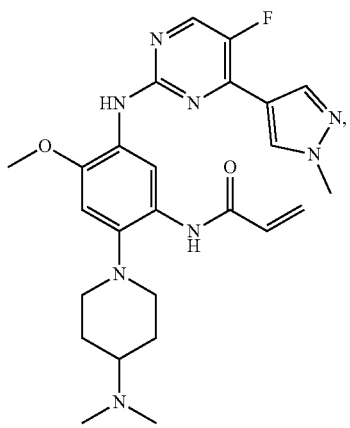

comprising:
1a) contacting the compound of formula X in a free base form with a solution comprising an organic solvent and an acid to form a turbid solution;
2a) stirring the turbid solution for a period of 1-72 hours;
3a) isolating a solid from the turbid solution; and
4a) drying the solid to provide a crystalline form,
wherein the acid is selected from the group consisting of hydrochloric acid, phosphoric acid, maleic acid, L-malic acid, and adipate acid;
the organic solvent is selected from the group consisting of methanol, ethanol, propanol, isopropanol, butanol, acetone, acetonitrile, tetrahydrofuran, propylene glycol, and mixtures thereof;
the molar ratio of the acid to the compound of formula X is (1-2):1;
steps 1a) and 2a) are conducted at a temperature of 5-30° C.; and
the crystalline form is selected from the group consisting of crystalline form A of a hydrochloride salt of the compound of formula X, crystalline form B of a phosphate salt of the compound of formula X, crystalline form C-1 of a maleate salt of the compound of formula X, crystalline form D of a L-malate salt of the compound of formula X, and crystalline form E of an adipate salt of the compound of formula X
or
1b) contacting a solution comprising the compound of formula X in a free base form and an organic solvent with maleic acid at a reflux temperature to form a mixture comprising a precipitate;
2b) cooling the mixture to a temperature of 5-15° C. over a period of 1-10 hours;
3b) isolating the precipitate; and
4b) drying the precipitate to provide crystalline form C-1 of a maleate salt of the compound of formula X,
wherein the organic solvent is selected from the group consisting of methanol, ethanol, propanol, isopropanol, butanol, acetone, acetonitrile, tetrahydrofuran, propylene glycol, and mixtures thereof; and
the molar ratio of the maleic acid to the compound of formula X is (1-3):1.
4. A pharmaceutical composition, comprising:
(a) the crystalline form of claim 1; and (b) a pharmaceutically acceptable carrier.

5. A method for treating EGFR-related diseases comprising administering the crystalline form of claim 1 to a subject in need thereof, the EGFR-related disease is non-small cell lung cancer.
6. The crystalline form of claim 1, wherein
the X-ray powder diffraction pattern of the crystalline form I is substantially characterized as in FIG. 13;
the X-ray powder diffraction pattern of the crystalline form II is substantially characterized as in FIG. 15;
the X-ray powder diffraction pattern of the crystalline form III is substantially characterized as in FIG. 17;
the X-ray powder diffraction pattern of the crystalline form IV is substantially characterized as in FIG. 19; and/or
the X-ray powder diffraction pattern of the crystalline form V is substantially characterized as in FIG. 21.
7. The process of claim 3, wherein the organic solvent in step 1a) is acetonitrile.
8. The process of claim 3, wherein the organic solvent in step 1b) is methanol, ethanol, acetone, or acetonitrile.
9. The process of claim 3, wherein step 2a) is conducted for a period of 10-50 hours.
10. The process of claim 3, wherein steps 1a) and 2a) are conducted at a temperature of 10-20° C.
11. The process of claim 3, wherein, in step 1a), the molar ratio of the acid to the compound of formula X is (1-1.2):1.
12. The process of claim 3, wherein, in step 1b), the molar ratio of the maleic acid to the compound of formula X is (1-1.5):1.
13. A process for preparing crystalline form C-2 of a maleate salt of a compound of formula X:

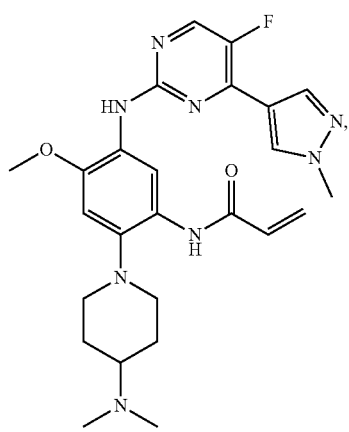

comprising:
1) dissolving crystalline form C-1 of a maleate salt of the compound of formula X with dichloromethane in a reaction vessel, which is then sealed and punctured with small holes; and
2) placing the reaction vessel under ventilation to allow slow natural volatilization to provide the crystalline form C-2 of the maleate salt of the compound of formula X.
14. The process of claim 13, wherein step 2) is conducted for a period of 10 days.
15. The process of claim 13, wherein step 2) is conducted at a temperature of 15° C.

* * * * *